(12) United States Patent
Fusi, II et al.

(10) Patent No.: US 9,668,839 B2
(45) Date of Patent: Jun. 6, 2017

(54) ORAL CARE SYSTEMS

(71) Applicant: JOHNSON & JOHNSON CONSUMER INC., Skillman, NJ (US)

(72) Inventors: Robert W. Fusi, II, Flemington, NJ (US); Richard J. Fougere, Washington Crossing, PA (US); Harold D. Ochs, Flemington, NJ (US); Justin McDonough, Flemington, NJ (US); Megha Reddy, Princeton, NJ (US); Curt Binner, Furlong, PA (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 0 days.

(21) Appl. No.: 14/669,894

(22) Filed: Mar. 26, 2015

(65) Prior Publication Data

US 2015/0196374 A1 Jul. 16, 2015

Related U.S. Application Data

(62) Division of application No. 12/844,883, filed on Jul. 28, 2010, now Pat. No. 9,022,959.

(60) Provisional application No. 61/229,839, filed on Jul. 30, 2009.

(51) Int. Cl.
*A61C 17/02* (2006.01)
*A61C 19/06* (2006.01)
*A61C 17/028* (2006.01)

(52) U.S. Cl.
CPC ...... *A61C 17/0211* (2013.01); *A61C 17/0202* (2013.01); *A61C 17/028* (2013.01); *A61C 19/063* (2013.01); *A61C 17/0217* (2013.01); *A61C 19/066* (2013.01)

(58) Field of Classification Search
CPC ............ A61C 17/0211; A61C 17/0214; A61C 17/0217; A61C 17/0288; A61C 17/0208; A61C 17/16; A61C 17/22; A61C 17/228; A61C 17/28; A61C 17/32; A61C 17/34; A61C 17/36; A61C 19/063; A61C 19/066
USPC .... 601/160–165; 433/71, 80, 81, 85, 87–88, 433/91, 216
See application file for complete search history.

(56) References Cited

U.S. PATENT DOCUMENTS

| | | | |
|---|---|---|---|
| 1,500,107 | A | 7/1924 | Chandler |
| 3,489,141 | A | 1/1970 | Warren, Jr. |
| 3,516,402 | A | 6/1970 | Toth |
| 3,566,869 | A | 3/1971 | Crowson |
| 3,731,675 | A | 5/1973 | Kelly |
| 3,840,992 | A | 10/1974 | English |

(Continued)

FOREIGN PATENT DOCUMENTS

| | | |
|---|---|---|
| CN | 2356653 | 1/2000 |
| CN | 1476314 A | 2/2004 |

(Continued)

*Primary Examiner* — Kari Rodriquez

(57) ABSTRACT

An oral care system that provides a beneficial effect to an oral cavity of a mammal by using a liquid effective for providing the beneficial effect, where the system includes means for directing the liquid onto a plurality of surfaces of the oral cavity, means for providing the liquid to the means for directing the liquid onto the surfaces of the oral cavity, means for providing reciprocation of the liquid over the plurality of surfaces under conditions effective to provide the beneficial effect; and a reservoir for containing the liquid.

9 Claims, 29 Drawing Sheets

(56) References Cited

U.S. PATENT DOCUMENTS

| | | | |
|---|---|---|---|
| 4,017,373 A | 4/1977 | Shaw | |
| 4,071,956 A | 2/1978 | Andress | |
| 4,106,501 A | 8/1978 | Ozbey et al. | |
| 4,148,309 A | 4/1979 | Reibel | |
| 4,164,940 A * | 8/1979 | Quinby | A61H 13/00 433/216 |
| 4,170,230 A | 10/1979 | Nelson | |
| 4,237,574 A | 12/1980 | Kelly et al. | |
| 4,291,017 A | 9/1981 | Beierle et al. | |
| 5,029,576 A | 7/1991 | Evans, Sr. | |
| 5,030,098 A | 7/1991 | Branford | |
| 5,046,491 A | 9/1991 | Derrick | |
| 5,104,315 A | 4/1992 | McKinley | |
| 5,137,039 A | 8/1992 | Klinkhammer | |
| 5,177,827 A | 1/1993 | Ellison | |
| 5,355,893 A | 10/1994 | Mick | |
| 5,365,624 A | 11/1994 | Berns | |
| 5,443,386 A | 8/1995 | Viskup | |
| 5,458,487 A | 10/1995 | Komatsu | |
| 5,509,801 A * | 4/1996 | Nicholson | 433/80 |
| 5,570,709 A | 11/1996 | Haddad et al. | |
| 5,616,028 A | 4/1997 | Hafele et al. | |
| 5,950,624 A | 9/1999 | Hart | |
| 5,980,498 A | 11/1999 | Brown | |
| 6,022,326 A | 2/2000 | Tatum | |
| 6,126,444 A | 10/2000 | Horiguchi | |
| 6,152,733 A | 11/2000 | Hegemann et al. | |
| 6,155,824 A | 12/2000 | Kamen et al. | |
| 6,174,164 B1 | 1/2001 | Masjedi | |
| 6,203,320 B1 | 3/2001 | Williams et al. | |
| 6,224,376 B1 | 5/2001 | Cloonan | |
| 6,353,956 B1 | 3/2002 | Berge | |
| 6,375,459 B1 * | 4/2002 | Kamen | A61C 3/025 433/80 |
| 6,602,071 B1 * | 8/2003 | Ellion | A46B 11/063 132/322 |
| 6,893,259 B1 * | 5/2005 | Reizenson | A61C 17/0211 433/29 |
| 6,935,857 B1 | 8/2005 | Farrell | |
| 7,118,377 B2 | 10/2006 | Inoue et al. | |
| 7,364,551 B2 | 4/2008 | Allen | |
| 7,935,065 B2 | 5/2011 | Martin | |
| 7,972,277 B2 | 7/2011 | Oki | |
| 9,022,959 B2 * | 5/2015 | Fusi et al. | 601/162 |
| 2002/0082544 A1 | 6/2002 | Thrash et al. | |
| 2003/0143511 A1 | 7/2003 | Trichas | |
| 2003/0153844 A1 | 8/2003 | Smith | |
| 2003/0233086 A1 | 12/2003 | Burns | |
| 2004/0045107 A1 | 3/2004 | Egeresi | |
| 2004/0082878 A1 | 4/2004 | Baldwin | |
| 2004/0087874 A1 | 5/2004 | Schneider | |
| 2004/0106081 A1 | 6/2004 | Karazivan et al. | |
| 2004/0146836 A1 | 7/2004 | Andersen | |
| 2004/0193235 A1 | 9/2004 | Altshuler et al. | |
| 2005/0037315 A1 | 2/2005 | Inoue et al. | |
| 2005/0096563 A1 | 5/2005 | Liang | |
| 2005/0136376 A1 | 6/2005 | Yeh | |
| 2005/0196725 A1 | 9/2005 | Fu | |
| 2005/0272002 A1 | 12/2005 | Chenvainu et al. | |
| 2006/0078844 A1 | 4/2006 | Goldman et al. | |
| 2006/0188841 A1 | 8/2006 | Edel et al. | |
| 2006/0292521 A1 | 12/2006 | Hegemann | |
| 2007/0039614 A1 | 2/2007 | Djupesland | |
| 2007/0106138 A1 | 5/2007 | Beiski | |
| 2007/0140777 A1 | 6/2007 | Brunson | |
| 2007/0184404 A1 | 8/2007 | Johnki | |
| 2007/0254260 A1 | 11/2007 | Alden | |
| 2008/0131844 A1 | 6/2008 | Taylor | |
| 2008/0182218 A1 | 7/2008 | Chen | |
| 2008/0199831 A1 | 8/2008 | Teichert et al. | |
| 2008/0216843 A1 | 9/2008 | Jiang | |
| 2008/0280251 A1 | 11/2008 | Gallagher | |
| 2009/0024058 A1 | 1/2009 | Blowick et al. | |
| 2009/0123886 A1 | 5/2009 | Vaska | |
| 2009/0136893 A1 | 5/2009 | Zegarelli | |
| 2009/0208898 A1 | 8/2009 | Kaplan | |
| 2010/0004555 A1 | 1/2010 | Bazemore | |
| 2010/0016908 A1 | 1/2010 | Martin | |
| 2010/0081954 A1 | 4/2010 | Hyde | |
| 2010/0242193 A1 | 9/2010 | Harrison et al. | |
| 2010/0311007 A1 | 12/2010 | Eliyahov | |
| 2010/0312133 A1 | 12/2010 | Bazemore | |
| 2010/0330538 A1 | 12/2010 | Salazar et al. | |
| 2011/0015543 A1 | 1/2011 | Butlin | |
| 2011/0021942 A1 | 1/2011 | Choe | |
| 2011/0027746 A1 | 2/2011 | McDonough et al. | |
| 2011/0027747 A1 | 2/2011 | Fougere et al. | |
| 2011/0027748 A1 | 2/2011 | Fusi, II | |
| 2011/0027758 A1 | 2/2011 | Ochs | |
| 2011/0213228 A1 | 9/2011 | Martin | |
| 2011/0294096 A1 | 12/2011 | DeCastro et al. | |
| 2011/0318705 A1 | 12/2011 | Sullivan | |
| 2012/0021375 A1 | 1/2012 | Binner | |
| 2012/0021376 A1 | 1/2012 | Iwamoto | |
| 2012/0123225 A1 | 5/2012 | Al-Tawil | |
| 2012/0219926 A1 | 8/2012 | Sullivan et al. | |
| 2013/0023797 A1 | 1/2013 | Hanewinkel | |
| 2013/0211270 A1 | 8/2013 | St. Laurent | |

FOREIGN PATENT DOCUMENTS

| | | |
|---|---|---|
| CN | 101035485 A | 9/2007 |
| CN | 101076298 A | 11/2007 |
| EP | 101618 A | 2/1984 |
| EP | 688542 A | 12/1995 |
| EP | 761181 A | 3/1997 |
| EP | 1525857 A | 4/2005 |
| FR | 2455456 A | 11/1980 |
| JP | 59125556 A | 7/1984 |
| JP | 2299651 A | 12/1990 |
| JP | 6217996 A | 8/1994 |
| JP | 7047088 A | 2/1995 |
| JP | 7-15004 | 3/1995 |
| JP | 11035435 A | 2/1999 |
| JP | 11309160 A | 11/1999 |
| JP | 2001-008736 A | 1/2001 |
| JP | 2001-120579 A | 5/2001 |
| JP | 2001-120627 A | 5/2001 |
| JP | 2002-045378 A | 2/2002 |
| JP | 2004-057315 A | 2/2004 |
| JP | 2004-230118 A | 8/2004 |
| JP | 2005-319254 A | 11/2005 |
| JP | 2005-334104 A | 12/2005 |
| JP | 2006020887 A | 1/2006 |
| JP | 2006-101941 A | 4/2006 |
| JP | 2006-239368 A | 9/2006 |
| JP | 2008-501412 A | 1/2008 |
| KR | 20100138680 A | 12/2010 |
| SU | 1024079 A | 6/1983 |
| WO | WO 96/07906 A1 | 3/1996 |
| WO | WO 01/97709 A | 12/2001 |
| WO | WO 03/039392 A | 5/2003 |
| WO | WO 2004/064666 A | 8/2004 |
| WO | WO 2004/108008 A | 12/2004 |
| WO | WO 2005/087133 A | 9/2005 |
| WO | WO 2005/107636 A | 11/2005 |
| WO | WO 2005/120387 A | 12/2005 |
| WO | WO 2006/040018 A | 4/2006 |
| WO | WO 2006/100452 A | 9/2006 |
| WO | WO 2006/119855 A | 11/2006 |
| WO | WO 2006/128021 A | 11/2006 |
| WO | WO 2007/071031 A | 6/2007 |
| WO | WO 2007/121760 A | 11/2007 |
| WO | WO 2008/016342 A | 2/2008 |

* cited by examiner

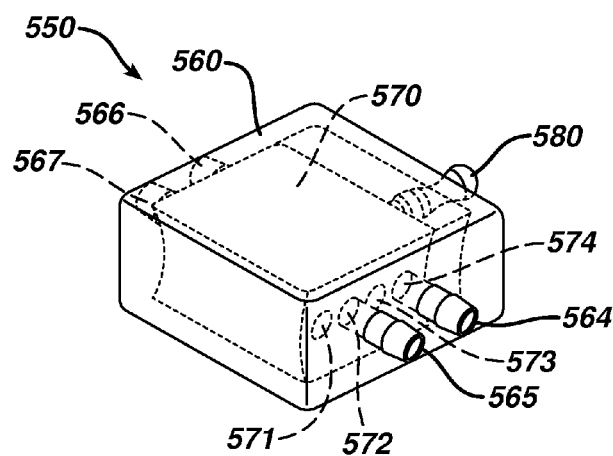
FIG. 7a
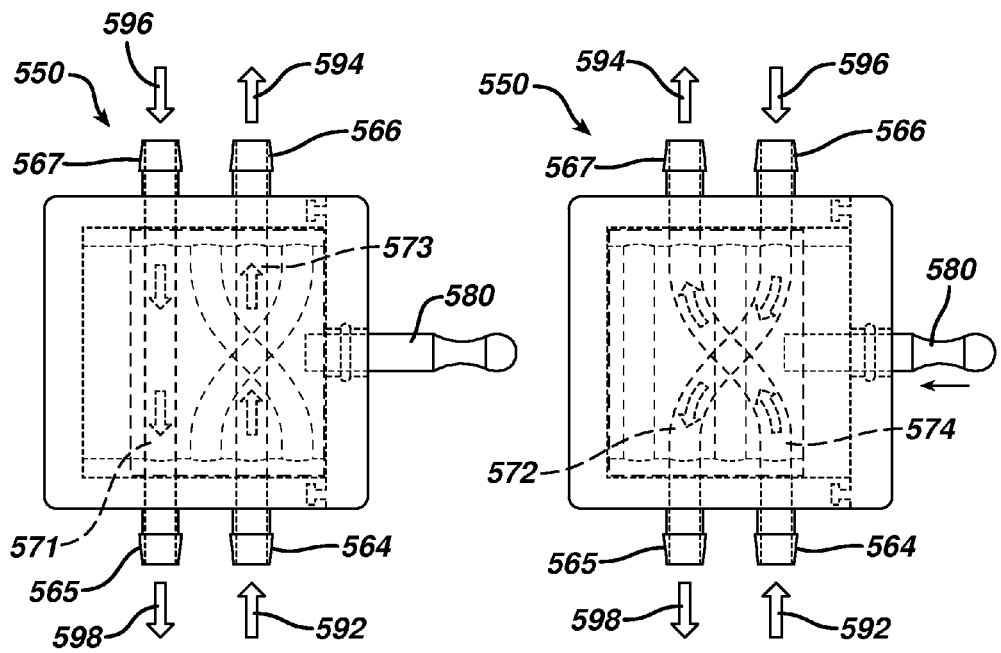
FIG. 7b　　　FIG. 7c

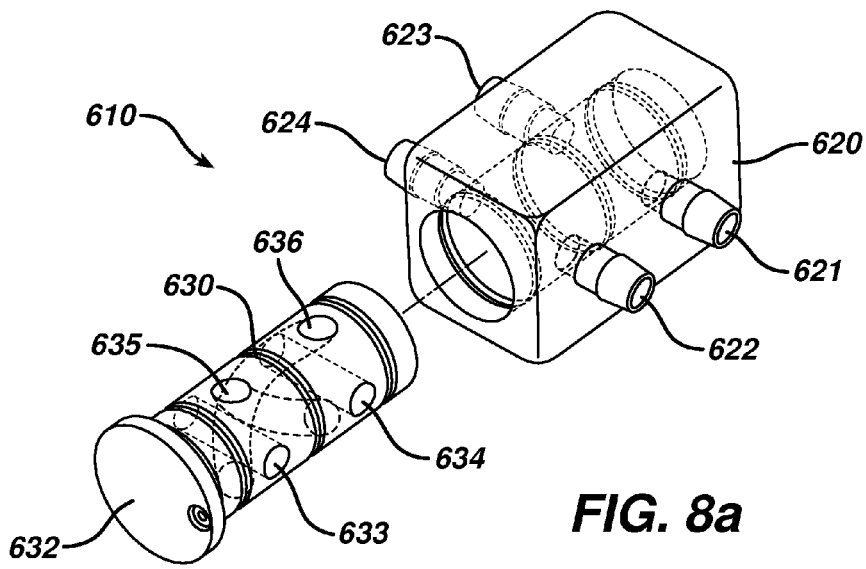
FIG. 8a
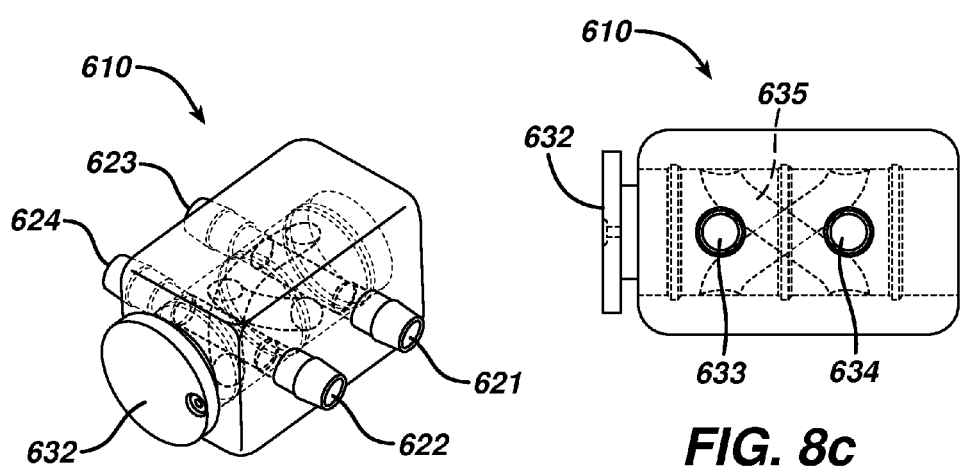
FIG. 8b
FIG. 8c

ORAL CARE SYSTEMS

CROSS-REFERENCE TO RELATED APPLICATION

This application is a divisional of U.S. non provisional application Ser. No. 12/844,883 filed Jul. 28, 2010 which claims the benefit U.S. provisional application 61/229,839 filed Jul. 30, 2009, the complete disclosures of which are hereby incorporated herein by reference for all purposes.

FIELD OF THE INVENTION

The present invention relates to oral care systems suitable for in-home use to provide a beneficial effect to the oral cavity of a mammal.

BACKGROUND OF THE INVENTION

In addition to regular professional dental checkups, daily oral hygiene is generally recognized as an effective preventative measure against the onset, development, and/or exacerbation of periodontal disease, gingivitis and/or tooth decay. Unfortunately, however, even the most meticulous individuals dedicated to thorough brushing and flossing practices often fail to reach, loosen and remove deep-gum and/or deep inter-dental food particulate, plaque or biofilm. Most individuals have professional dental cleanings biannually to remove tarter deposits.

For many years products have been devised to facilitate the simple home cleaning of teeth, although as yet a single device which is simple to use and cleans all surfaces of a tooth and/or the gingival or sub-gingival areas simultaneously is not available. The conventional toothbrush is widely utilized, although it requires a significant input of energy to be effective and, furthermore, a conventional toothbrush cannot adequately clean the inter-proximal areas of the teeth. Cleaning of the areas between teeth currently requires the use of floss, pick, or some such other additional device apart from a toothbrush.

Electric toothbrushes have achieved significant popularity and, although these reduce the energy input required to utilize a toothbrush, they are still inadequate to ensure proper inter-proximal tooth cleaning. Oral irrigators are known to clean the inter-proximal area between teeth. However, such devices have a single jet which must be directed at the precise inter-proximal area involved in order to remove debris. These water pump type cleaners are therefore typically only of significant value in connection with teeth having braces thereupon which often trap large particles of food. It will be appreciated that if both debris and plaque are to be removed from teeth, at present a combination of a number of devices must be used, which is extremely time consuming and inconvenient.

In addition, in order for such practices and devices to be effective, a high level of consumer compliance with techniques and/or instructions is required. The user-to-user variation in time, cleaning/treating formula, technique, etc., will affect the cleaning of the teeth.

The present invention ameliorates one or more of the above mentioned disadvantages with existing oral hygiene apparatus and methods, or at least provides the market with an alternative technology that is advantageous over known technology, and also may be used to ameliorate a detrimental condition or to improve cosmetic appearance of the oral cavity.

SUMMARY OF THE INVENTION

The present invention is an oral care system that provides a beneficial effect to the oral cavity of a mammal by using a liquid effective for providing the beneficial effect. The system includes means for directing the liquid onto a plurality of surfaces of the oral cavity, means for providing the liquid to the means for directing the liquid onto the surfaces of the oral cavity, means for providing reciprocation of the liquid over the plurality of surfaces under conditions effective to provide the beneficial effect; and a reservoir for containing the liquid.

BRIEF DESCRIPTION OF THE DRAWINGS

FIG. 6b is an exploded view of the reciprocating flow controller of FIG. 6a;

FIG. 7a is a perspective drawing of a first alternative embodiment of a reciprocating flow controller according to the present invention;

FIG. 7b is a top view of the reciprocating flow controller of FIG. 7a in its first position;

FIG. 7c is a top view of the reciprocating flow controller of FIG. 7a in its second position;

FIG. 8a is an exploded view of a second alternative embodiment of a reciprocating flow controller according to the present invention;

FIG. 8b is a perspective drawing of the reciprocating flow controller of FIG. 8a;

FIG. 8c is a side view of the reciprocating flow controller of FIG. 8a in its first position;

FIG. 9b is an exploded view of the reciprocating flow controller of FIG. 9a;

FIG. 10b is a side view of the reciprocating flow controller of FIG. 10a;

FIG. 24b is an exploded view of the pumping section of the hand piece of FIG. 24a;

FIG. 24c is an exploded view of the vacuum section of the hand piece of FIG. 24a;

FIG. 24d is a side view of the drive system of the pumping and driving sections of the hand piece of FIG. 24a;

FIG. 24e is a cut-away view of the hand piece of FIG. 24a;

FIG. 25b is a front, top perspective view of the system of FIG. 25a;

DETAILED DESCRIPTION OF THE INVENTION

Figure 1:
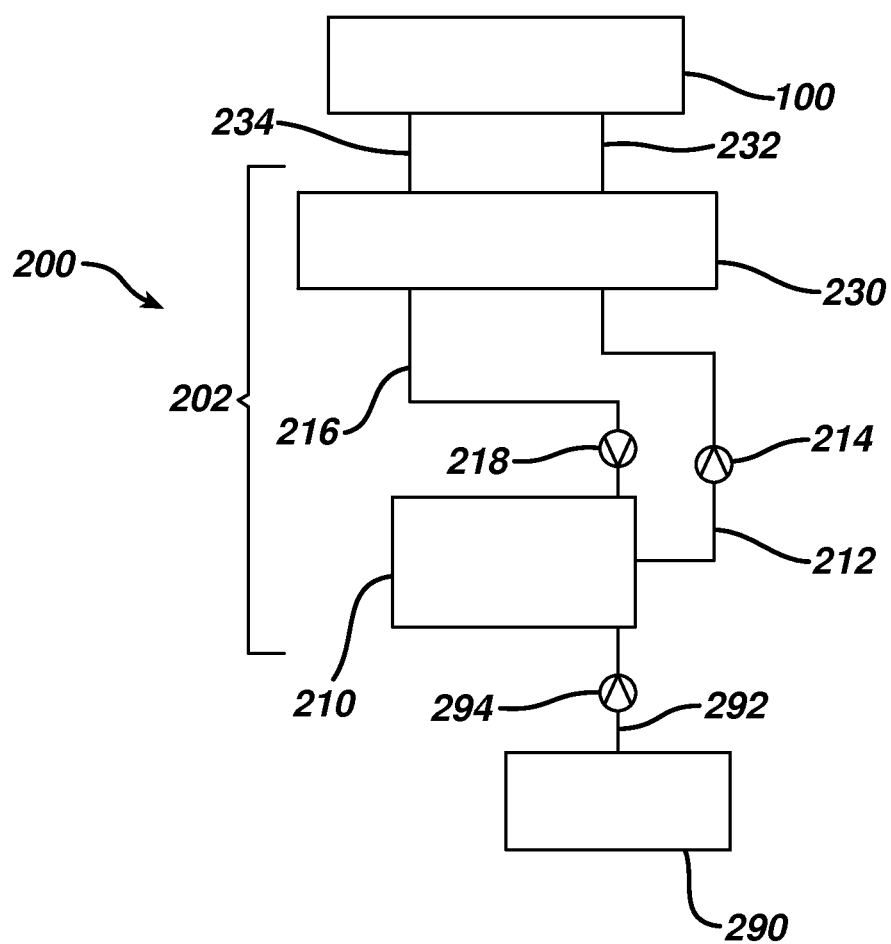
FIG. 1 is a schematic drawing of one embodiment of a system according to the present invention.

The terms "reciprocating movement of liquid(s)" and "reciprocation of liquid(s)" are used interchangeably herein. As used herein, both terms mean alternating the direction of flow of the liquid(s) back and forth over surfaces of the oral cavity of a mammal from a first flow direction to a second flow direction that is opposite the first flow direction.

By "effective fit or seal", it is meant that the level of sealing between the means for directing liquid onto and about the plurality of surfaces in the oral cavity, e.g. an application tray, is such that the amount of leakage of liquid from the tray into the oral cavity during use is sufficiently low so as to reduce or minimize the amount of liquid used and to maintain comfort of the user, e.g. to avoid choking or gagging. Without intending to be limited, gagging is understood to be a reflex (i.e. not an intentional movement) muscular contraction of the back of the throat caused by stimulation of the back of the soft palate, the pharyngeal wall, the tonsillar area or base of tongue, meant to be a protective movement that prevents foreign objects from entering the pharynx and into the airway. There is variability in the gag reflex among individuals, e.g. what areas of the mouth stimulate it. In addition to the physical causes of gagging, there may be a psychological element to gagging, e.g. people who have a fear of choking may easily gag when something is placed in the mouth.

As used herein, "means for conveying liquid" includes structures through which liquid may travel or be transported throughout the systems according to the invention and includes, without limitation passages, conduits, tubes, ports, portals, channels, lumens, pipes and manifolds. Such means for conveying liquids may be utilized in devices for providing reciprocation of liquids and means for directing liquids onto and about surfaces of the oral cavity. Such conveying means also provide liquid to the directing means and provides liquid to the reciprocation means from a reservoir for containing liquid, whether the reservoir is contained within a hand-held device containing the reciprocation means or a base unit. The conveying means also provides liquid from a base unit to a liquid reservoir contained within the hand-held device. Described herein are methods, devices and systems useful in providing a beneficial effect to an oral cavity of a mammal, e.g. a human.

Methods entail contacting a plurality of surfaces of the oral cavity with a liquid that is effective for providing the desired beneficial effect to the oral cavity. In such methods, reciprocation of the liquid(s) over the plurality of surfaces of the oral cavity is provided under conditions effective to provide the desired beneficial effect to the oral cavity. Contact of the plurality of surfaces by the liquid may be conducted substantially simultaneous. By substantially simultaneous, it is meant that, while not all of the plurality of surfaces of the oral cavity are necessarily contacted by the fluid at the same time, the majority of the surfaces are contacted simultaneously, or within a short period of time to provide an overall effect similar to that as if all surfaces are contacted at the same time.

The conditions for providing the desired beneficial effect in the oral cavity may vary depending on the particular environment, circumstances and effect being sought. The different variables are interdependent in that they create a specific velocity of the liquid. The velocity requirement may be a function of the formulation in some embodiments. For example, with change in the viscosity, additives, e.g. abrasives, shear thinning agents, etc., and general flow properties of the formulation, velocity requirements of the jets may change to produce the same level of efficacy. Factors which may be considered in order to provide the appropriate conditions for achieving the particular beneficial effect sought include, without limitation, the velocity and/or flow rate and/or pressure of the liquid stream, pulsation of the liquid, the spray geometry or spray pattern of the liquid, the temperature of the liquid and the frequency of the reciprocating cycle of the liquid.

The liquid pressures, i.e. manifold pressure just prior to exit through the jets, may be from about 0.5 psi to about 30 psi, or from about 3 to about 15 psi, or about 5 psi. Flow rate of liquid may be from about 10 ml/s to about 60 ml/s, or about 20 ml/s to about 40 ml/s. It should be noted that the larger and higher quantity of the jets, the greater flow rate required at a given pressure/velocity. Pulse frequency (linked to pulse length and delivery (ml/pulse), may be from about 0.5 Hz to about 50 Hz, or from about 5 Hz to about 25 Hz. Delivery pulse duty cycle may be from about 10% to 100%, or from about 40% to about 60%. It is noted that at 100% there is no pulse, but instead a continuous flow of liquid. Delivery pulse volume (total volume through all jets/nozzles) may be from about 0.2 ml to about 120 ml, or from about 0.5 ml to about 15 ml. Velocity of jetted pulse may be from about 4 cm/s to about 400 cm/s, or from about 20 cm/s to about 160 in/s. Vacuum duty cycle may be from about 10% to 100%, or from about 50% to 100%. It is noted that vacuum is always on at 100%. Volumetric delivery to vacuum ratio may be from about 2:1 to about 1:20, or from about 1:1 to 1:10.

Once having the benefit of this disclosure, one skilled in the art will recognize that the various factors may be controlled and selected, depending on the particular circumstances and desired benefit sought.

The liquid(s) will include at least one ingredient, or agent, effective for providing the beneficial effect sought, in an amount effective to provide the beneficial effect when contacted with the surfaces of the oral cavity. For example, the liquid may include, without limitation, an ingredient selected from the group consisting of a cleaning agent, an antimicrobial agent, a mineralization agent, a desensitizing agent and a whitening agent. In certain embodiments, more than one liquid may be used in a single session. For example, a cleaning solution may be applied to the oral cavity, followed by a second solution containing, for example, a whitening agent or an antimicrobial agent. Solutions also may include a plurality of agents to accomplish more than one benefit with a single application. For example, the solution may include both a cleansing agent and an agent for ameliorating a detrimental condition, as further discussed below. In addition, a single solution may be effective to provide more than one beneficial effect to the oral cavity. For example, the solution may include a single agent that both cleans the oral cavity and acts as an antimicrobial, or that both cleans the oral cavity and whitens teeth.

Liquids useful for improving the cosmetic appearance of the oral cavity may include a whitening agent to whiten teeth in the cavity. Such whitening agents may include, without limitation, hydrogen peroxide and carbamide peroxide, or other agents capable of generating hydrogen peroxide when applied to the teeth. Such agents are well known within the art related to oral care whitening products such as rinses, toothpastes and whitening strips. Other whitening agents may include abrasives such as silica, sodium bicarbonate, alumina, apatites and bioglass.

It is noted that, while abrasives may serve to clean and/or whiten the teeth, certain of the abrasives also may serve to ameliorate hypersensitivity of the teeth caused by loss of enamel and exposure of the tubules in the teeth. For example, the particle size, e.g. diameter, of certain of the materials, e.g. bioglass, may be effective to block exposed tubules, thus reducing sensitivity of the teeth.

In some embodiments, the liquid may comprise an antimicrobial composition containing an alcohol having 3 to 6 carbon atoms. The liquid may be an antimicrobial mouthwash composition, particularly one having reduced ethanol content or being substantially free of ethanol, providing a high level of efficacy in the prevention of plaque, gum disease and bad breath. Noted alcohols having 3 to 6 carbon atoms are aliphatic alcohols. A particularly aliphatic alcohol having 3 carbons is 1-propanol.

In one embodiment the liquid may comprise an antimicrobial composition comprising (a) an antimicrobial effective amount of thymol and one or more other essential oils, (b) from about 0.01% to about 70.0% v/v, or about 0.1% to about 30% v/v, or about 0.1% to about 10% v/v, or about 0.2% to about 8% v/v, of an alcohol having 3 to 6 carbon atoms and (c) a vehicle. The alcohol may be 1-propanol. The liquid vehicle can be aqueous or non-aqueous, and may include thickening agents or gelling agents to provide the compositions with a particular consistency. Water and water/ethanol mixtures are the preferred vehicle.

Another embodiment of the liquid is an antimicrobial composition comprising (a) an antimicrobial effective amount of an antimicrobial agent, (b) from about 0.01% to about 70% v/v, or about 0.1% to about 30% v/v, or about 0.2% to about 8% v/v, of propanol and (c) a vehicle. The antimicrobial composition of this embodiment exhibits unexpectedly superior delivery system kinetics compared to prior art ethanolic systems. Exemplary antimicrobial agents which may be employed include, without limitation, essential oils, cetyl pyridium chloride (CPC), chlorhexidine, hexetidine, chitosan, triclosan, domiphen bromide, stannous fluoride, soluble pyrophosphates, metal oxides including but not limited to zinc oxide, peppermint oil, sage oil, sanguinaria, dicalcium dihydrate, aloe vera, polyols, protease, lipase, amylase, and metal salts including but not limited to zinc citrate, and the like. A particularly preferred aspect of this embodiment is directed to an antimicrobial oral composition, e.g. a mouthwash having about 30% v/v or less, or about 10% v/v or less, or about 3% v/v or less, of 1-propanol.

Yet another embodiment of the liquid is a reduced ethanol, antimicrobial mouthwash composition which comprises (a) an antimicrobial effective amount of thymol and one or more other essential oils; (b) from about 0.01 to about 30.0% v/v, or about 0.1% to about 10% v/v, or about 0.2% to about 8% v/v, of an alcohol having 3 to 6 carbon atoms; (c) ethanol in an amount of about 25% v/v or less; (d) at least one surfactant; and (e) water. Preferably the total concentration of ethanol and alcohol having 3 to 6 carbon atoms is no greater than 30% v/v, or no greater than 25% v/v, or no greater than 22% v/v.

In still another embodiment, the liquid is an ethanol-free antimicrobial mouthwash composition which comprises (a) an antimicrobial effective amount of thymol and one or more other essential oils; (b) from about 0.01% to about 30.0% v/v, or about 0.1% to about 10% v/v, or about 0.2% to about 8%, of an alcohol having 3 to 6 carbon atoms; (c) at least one surfactant; and (d) water.

The alcohol having 3 to 6 carbon atoms is preferably selected from the group consisting of 1-propanol, 2-propanol, 1-butanol, 2-butanol, tert-butanol and corresponding diols. 1-Propanol and 2-propanol are preferred, with 1-propanol being most preferred.

In addition to generally improving the oral hygiene of the oral cavity by cleaning, for example, removal or disruption of plaque build-up, food particles, biofilm, etc., the inventions are useful to ameliorate detrimental conditions within the oral cavity and to improve the cosmetic appearance of the oral cavity, for example whitening of the teeth. Detrimental conditions may include, without limitation, caries, gingivitis, inflammation, symptoms associated with periodontal disease, halitosis, sensitivity of the teeth and fungal infection. The liquids themselves may be in various forms, provided that they have the flow characteristics suitable for use in devices and methods of the present invention. For example, the liquids may be selected from the group consisting of solutions, emulsions and dispersions. In certain embodiments, the liquid may comprise a particulate, e.g. an abrasive, dispersed in a liquid phase, e.g. an aqueous phase. In such cases, the abrasive would be substantially homogeneously dispersed in the aqueous phase in order to be applied to the surfaces of the oral cavity. In other embodiments, an oil-in-water or water-in-oil emulsion may be used. In such cases, the liquid will comprise a discontinuous oil phase substantially homogeneously dispersed within a continuous aqueous phase, or a discontinuous aqueous phase substantially homogenously dispersed in a continuous oil phase, as the case may be. In still other embodiments, the liquid may be a solution whereby the agent is dissolved in a carrier, or where the carrier itself may be considered as the agent for providing the desired beneficial effect, e.g., an alcohol or alcohol/water mixture, usually having other agents dissolved therein.

Disclosed herein are systems, e.g. systems comprising oral care devices, for example a dental cleaning apparatus, suitable for in-home use and adapted to direct liquid onto a plurality of surfaces of a tooth and/or the gingival area, as well as methods utilizing such systems. In certain embodiments the surfaces of the oral cavity are contacted by the liquid substantially simultaneously. As used herein, reference to the gingival area includes, without limitation, reference to the sub-gingival pocket. The appropriate liquid is directed onto a plurality of surfaces of teeth and/or gingival area substantially simultaneously in a reciprocating action under conditions effective to provide cleaning, and/or general improvement of the cosmetic appearance of the oral cavity and/or amelioration of a detrimental condition of the teeth and/or gingival area, thereby providing generally improved oral hygiene of teeth and/or gingival area. For example, one such device cleans teeth and/or the gingival area and removes plaque using an appropriate cleaning liquid by reciprocating the liquid back and forth over the front and back surfaces and inter-proximal areas of the teeth, thereby creating a cleaning cycle while minimizing the amount of cleaning liquid used.

Systems of the invention comprise devices that provide reciprocation of the liquid, which devices comprise a means for controlling reciprocation of the liquid. The controlling means includes means for conveying the liquid to and from a means for directing the liquid onto the plurality of surfaces of the oral cavity. In certain embodiments, the means for providing reciprocation of the liquid comprises a plurality of portals for receiving and discharging the liquid, a plurality of passages, or conduits, through which the liquid is conveyed, and means for changing the direction of flow of the liquid to provide reciprocation of the liquid, as described in more detail herein below. The controlling means may be controlled by a logic circuit and/or a mechanically controlled circuit.

In certain embodiments, devices for providing reciprocation may include a means for attaching or connecting the device to a reservoir for containing the liquid. The reservoir may be removably attached to the device. In this case, the reservoir and the device may comprise means for attaching one to the other. After completion of the process, the reservoir may be discarded and replaced with a different reservoir, or may be refilled and used again. In other embodiments, the reciprocating device will include a reservoir integral with the device. In embodiments where the device may be attached to a base unit, as described herein, the reservoir, whether integral with the device or removably attached to the device, may be refilled from a supply reservoir which forms a part of the base unit. Where a base unit is utilized, the device and the base unit will comprise means for attaching one to the other.

The device will comprise a power source for driving the means for reciprocating liquids. The power source may be contained within the device, e.g. in the handle of the device, for example, batteries, whether rechargeable or disposable. Where a base unit is employed, the base may include means for providing power to the device. In other embodiments, the base unit may include means for recharging the rechargeable batteries contained within the device.

Devices for providing reciprocation of liquids will include means for attaching the device to means for directing the liquid onto the plurality of surfaces of the oral cavity, e.g. an application tray or mouthpiece. In certain embodiments, the directing means provides substantially simultaneous contact of the plurality of surfaces of the oral cavity by the liquid. The attachment means may provide removable attachment of the mouthpiece to the device. In such embodiments, multiple users may use their own mouthpiece with the single device comprising the reciprocating means. In other embodiments, the attachment means may provide a non-removable attachment to the mouthpiece, whereby the mouthpiece is an integral part of the device. Devices for providing reciprocation as described above may be contained within a housing also containing other device components so as to provide a hand-held device suitable for providing liquid to the directing means, as described herein below.

The means for directing the liquid onto the surfaces of the oral cavity, e.g. an application tray or mouthpiece, is comprised of multiple components. The directing means comprises a chamber for maintaining the liquid proximate the plurality of surfaces, i.e. liquid-contacting-chamber (LCC). By "proximate", it is meant that the liquid is maintained in contact with the surfaces. The LCC is defined by the space bounded by the front inner wall and rear inner wall of the mouthpiece, and a wall, or membrane, extending between and integral with the front and rear inner walls of the mouthpiece, and in certain embodiments, a rear gum-sealing membrane. Together, the front and rear inner walls, the wall extending there between and rear gum-sealing membrane form the LCC membrane (LCCM). The general shape of the LCCM is that of a "U" or an "n", depending on the orientation of the mouthpiece, which follows the teeth to provide uniform and optimized contact by the liquid. The LCCM may be flexible or rigid depending on the particular directing means. The membrane may be located as a base membrane of the LCCM. The front and rear inner walls of the LCCM each include a plurality of openings, or slots, through which the liquid is directed to contact the plurality of surfaces of the oral cavity.

The LCCM design may be optimized for maximum effectiveness as it relates to the size, shape, thickness, materials, volume created around the teeth/gingiva, nozzle design and placement as it relates to the oral cavity and the teeth in conjunction with the manifold and gingival margin seal to provide comfort and minimize the gagging reflex of the user. The combination of the above provides effective contact of the teeth and gingival area by the liquid.

The LCCM provides a controlled and isolated environment with known volume, i.e. the LCC, to contact teeth and/or gingival area with liquids, and then to remove spent liquids, as well as debris, plaque, etc., from the LCC without exposing the whole oral cavity to liquid, debris, etc. This decreases the potential for ingestion of the liquids. The LCCM also allows increased flow rates and pressure of liquids without drowning the individual nozzles when significant flow rates are required to provide adequate cleaning, for example. The LCCM also allows reduced liquid quantities and flow rates when required, as only the area within the LCC is being contacted with liquid, not the entire oral cavity. The LCCM also allows controlled delivery and duration of contact of liquid on, through and around teeth and the gingival area, allowing increased concentrations of liquids on the area being contacted by the liquid, thereby providing more effective control and delivery of liquid.

The thickness of the walls of the LCCM may be within a range of 0.2 mm to 1.5 mm, to provide necessary physical performance properties, while minimizing material content, and optimizing performance. The distance between the inner walls of the LCCM to the teeth may be from about 0.1 mm to about 5 mm, and more typically an average distance of about 2.5 mm to provide maximum comfort, while minimizing customization and LCC volume requirements.

The size and shape of the mouthpiece preferably utilizes three basic universal sizes (small, medium and large) for both the top and bottom teeth, but the design provides mechanisms to allow different levels of customization as required to ensure comfort and functionality to the individual user. The device may incorporate a switching mechanism, which would allow it to be operable only when in the correct position in the mouth. The mouthpiece may include both upper and lower sections to provide substantially simultaneous contact of the plurality of surfaces of the oral cavity by liquid. In an alternate embodiment the upper and lower sections may be cleaned utilizing a single bridge that could be used on the upper or lower teeth and gums of the user (first placed on one portion for cleaning, then subsequently placed over the other portion for cleaning).

The number and location of openings, also referred to herein as slots, jets or nozzles, contained within the inner walls of the mouthpiece through which the liquid is directed will vary and be determined based upon the circumstances and environment of use, the particular user and the beneficial effect being sought. The cross-sectional geometry of the openings may be circular, elliptical, trapezoidal, or any other geometry that provides effective contact of the surfaces of the oral cavity by the liquid. The location and number of openings may be designed to direct jets of liquid in a variety of spray patterns effective for providing the desired beneficial effect. Opening diameters may be from about 0.1 to about 3 mm, or from about 0.2 mm to about 0.8 mm, or about 0.5 mm, to provide effective cleaning and average jet velocities and coverage.

Optimal opening placement and direction/angles allows coverage of substantially all teeth surfaces in the area if the oral cavity to be contacted by liquid, including but not limited to interdental, top, side, back, and gingival pocket surfaces. In alternate embodiments, the openings could be of different sizes and different shapes to provide different cleaning, coverage and spray patterns, to adjust velocities, density and fan patterns (full cone, fan, partial, cone, jet), or due to formulation consideration. Nozzles could also be designed to be tubular and or extend from the LCC membrane to provide directed spray, or act as sprinkler like mechanism to provide extended coverage across the teeth, similar to a hose sprinkler system. The nozzles are preferably integral to the inner walls of the LCC membrane and can be incorporated into the inner walls through any number of assembly or forming techniques known in the art (insert molded, formed in membrane through machining, injection molding, etc.).

The LCCM may be an elastomeric material such as ethylene vinyl acetate (EVA), thermoplastic elastomer (TPE), or silicone, to allow motion of the inner walls and provide a greater jet coverage area with minimal mechanics, reducing the volumetric flow requirements to achieve optimized performance, while providing a softer and more flexible material to protect the teeth if direct contact with the teeth is made. A flexible membrane may also provide acceptable fitment over a large range of users, due to its ability to conform to the teeth. Alternatively, the LCCM could be made of a rigid or semi-rigid material, such as but not limited to a thermoplastic.

In an alternate embodiment, the LCCM could also include abrasive elements such as filaments, textures, polishing elements, additives (silica, etc.), and other geometric elements that could be used for other cleaning and/or treatment requirements as well as ensuring minimal distance between the teeth and LCCM for, but not limited to, treatment, cleaning, and positioning.

The LCCM could be created via a variety of methods such as, but not limited to, machining, injection molding, blow molding, extrusion, compression molding, and/or vacuum forming. It can also be created in conjunction with the manifold, but incorporating the manifold circuitry within the LCC, and/or over-molded onto the manifold to provide a unitary construction with minimal assembly.

In one embodiment, the LCCM may be fabricated separately and then assembled to the manifolds, utilizing any number of assembling and sealing techniques, including adhesives, epoxies, silicones, heat sealing, ultrasonic welding, and hot glue. The LCCM is designed in a way that, when assembled with the manifold, it effectively and efficiently creates the preferred dual manifold design without any additional components.

In certain embodiments, the LCCM can also be designed or used to create the gingival sealing area. In certain embodiments, a vacuum is applied within the LCC, which improves the engagement of the mouthpiece to form a positive seal with the gingival in the oral cavity. In other embodiments, a pressure is applied outside the LCCM, within the oral cavity, which improves the engagement of the mouthpiece to form a positive seal with the gingival in the oral cavity. In yet other embodiments, a denture-like adhesive may be applied around the mouthpiece during the initial use to provide a custom reusable resilient seal when inserted into the oral cavity for a particular user. It would then become resiliently rigid to both conform and provide a positive seal with the guns and on subsequent applications. In another embodiment, the seal could be applied and/or replaced or disposed of after each use.

The directing means also comprise a first manifold for containing the liquid and for providing the liquid to the LCC through the openings of the front inner wall, and a second manifold for containing the liquid and for providing the liquid to the chamber through the openings of the rear inner wall. This design provides a number of different options, depending on what operation is being conducted. For instance, in a cleaning operation, it may be preferable to deliver jets of liquid into the LCC directly onto the teeth from one side of the LCC from the first manifold and then evacuate/pull the liquid around the teeth from the other side of the LCC into the second manifold to provide controlled interdental, gumline and surface cleaning. This flow from the one side of the LCC could be repeated a number of times in a pulsing action before reversing the flow to deliver jets of liquid from the second manifold and evacuating/pulling the liquid through the back side of the teeth into the first manifold for a period of time and/or number of cycles. Such liquid action creates a turbulent, repeatable and reversible flow, thus providing reciprocation of the liquid about the surfaces of the oral cavity.

In alternate embodiments, the manifold can be of single manifold design providing pushing and pulling of the liquid through the same sets of jets simultaneously, or can be any number of manifold divisions to provide even greater control of the liquid delivery and removal of the cleaning and liquid treatment. In the multi-manifold also can be designed to have dedicated delivery and removal manifolds. The manifolds can also be designed to be integral to and/or within the LCCM.

The material for the manifold would be a semi-rigid thermoplastic, which would provide the rigidity necessary not to collapse or burst during the controlled flow of the liquids, but to provide some flexibility when fitting within the user's mouth for mouthpiece insertion, sealing/position and removal. To minimize fabrication complexity, number of components and tooling cost, the dual manifold is created when assembled with the LCCM. The manifold could also be multi-component to provide a softer external "feel" to the teeth/gums utilizing a lower durometer elastomeric material, such as, but not limited to, a compatible thermoplastic elastomer (TPE). The manifold could be created via a variety of methods such as, but not limited to machining, injection molding, blow molding, compression molding, or vacuum forming.

The directing means also comprises a first port for conveying the liquid to and from the first manifold and a second port for conveying the liquid to and from the second manifold, and means for providing an effective seal of the directing means within the oral cavity, i.e. a gingival seal. In certain embodiments, the first and second ports may serve both to convey liquid to and from the first and second manifolds and to attach the mouthpiece to the means for providing liquid to the mouthpiece. In other embodiments, the directing means may further include means for attaching the directing means to means for providing liquid to the directing means.

FIG. 1 is a schematic drawing of an embodiment of a system according to the present invention. The figure shows system 200, with components including: means for providing reciprocation of liquid in the oral cavity 202, means for directing the liquid onto the plurality of surfaces of the oral cavity, in this instance shown as application tray 100, and liquid supply reservoir 290. Means for providing reciprocation of liquids may include, in this embodiment, delivery/collection device 210, reciprocating flow controller 230, tubes 212, 216, and 292 for conveying the liquid throughout the system, and liquid one-way flow valves 214, 218 and 294. Tubes 232 and 234 provide for conveyance of the liquid from reciprocating flow controller 230 to application tray 100.

In some embodiments, delivery/collection device 210 may be a piston pump. Liquid supply reservoir 290 may be made of glass, plastic or metal. Liquid supply reservoir 290 may be integral to system 200 and refillable. In some embodiments, liquid supply reservoir 290 may be a replaceable liquid supply, such as a single or multi-use cartridge, detachably connected to system 200.

In some embodiments, liquid supply reservoir 290 and/or tubes 212, 292, may include a heat source to pre-warm the liquid prior to direction into application tray 100 for application to the surfaces of the oral cavity. The temperature should be maintained within a range effective to provide efficacy and comfort to the user during use.

Application tray 100, discussed in detail herein below, could be integral with, or detachably connected to reciprocating means 202 by way of tubes 232, 234 and further attachment means (not shown). It could be one or two sided with internally, easily cleanable filters for trapping food particles. When positioned within the oral cavity, e.g. about the teeth and gums, tray 100 forms an effective fit or seal against the gums, and includes means to direct liquid against surfaces of the oral cavity, e.g. surfaces of the teeth.

Liquid in liquid supply reservoir 290 flows through tube 292 to delivery/collection device 210. Liquid flow through tube 292 is controlled by one-way flow valve 294. From delivery/collection device 210, liquid flows through tube 212 to reciprocating flow controller 230. One-way flow valve 214 controls the liquid flow through tube 212. Liquid flows from reciprocating flow controller 230 to application tray 100 either through tube 232 or 234, depending on the flow direction setting of flow controller 230. Liquid flows from application tray 100, through either tube 234 or 232 back to reciprocating flow controller 230, and from reciprocating flow controller 230 to delivery/collection device 210, through tube 216. One-way flow valve 218 controls the liquid flow through tube 216.

The actions of delivery/collection device 210 may be controlled by a logic circuit, which may include a program to start the reciprocation cycle, a program to execute the reciprocation cycle, i.e. to cause liquid to be reciprocated about the teeth, thereby providing the beneficial effect to the oral cavity, e.g. cleaning the teeth, a program to empty application tray 100 at the end of the reciprocation cycle, and a self-cleaning cycle to clean the system between uses, or at pre-set or automatic cleaning times.

Though not shown, a face panel with a series of switches and indicator lights may also be incorporated into system 200. Switches may include, but are not limited to, on/off, fill application tray 100, run the reciprocation program, empty system 200, and clean system 200. Indicator, or display, lights include, but are not limited to, power on, charging, reciprocation program running, system emptying, cleaning results or feedback, and self-cleaning cycle in operation. In embodiments where liquid is pre-warmed prior to direction into application tray 100, a display light could be used to indicate that the liquid is at the proper temperature for use.

One method of using system 200 to clean teeth is as follows. In the first step, the user positions application tray 100 in the oral cavity about the teeth and gingival area. The user closes down on tray 100, thereby achieving an effective fit or seal between gums, teeth and tray 100. In use of the system according to the invention, the user pushes a start button initiating the cleaning process. The cleaning process is as follows:

1. Delivery/collection device 210 is activated to begin drawing cleaning liquid from liquid supply reservoir 290 through tube 292 and one-way valve 294.
2. Once delivery/collection device 210 is sufficiently filled, delivery/collection device 210 is activated to begin dispensing cleaning liquid to application tray 100 via tube 212, one-way valve 214, reciprocating flow controller 230, and tube 232. Cleaning liquid will be prevented from flowing through tubes 216 and 292 by one-way flow valves 218 and 294, respectively.
3. Delivery/collection device 210 is activated to begin drawing cleaning liquid from application tray 100 through tube 234, then through reciprocation flow controller 230, then through tube 216 and one-way valve 218. Cleaning liquid will be prevented from flowing through tube 212 by one-way flow valve 214. If there is insufficient cleaning liquid to adequately fill delivery/collection device 210, additional cleaning liquid may be drawn from liquid supply reservoir 290 through tube 292 and one-way valve 294.

4. The direction of the liquid flow is then reversed.
5. To reciprocate the cleaning liquid, steps 2 and 3 are repeated after the flow direction is reversed, cycling cleaning liquid between delivery/collection device 210 and application tray 100, using tubes 234 and 232, respectively.
6. The reciprocation cycle described continues until the time required for cleaning has expired, or the desired numbers of cycles are complete.

It is noted that there may be a delay between steps 2 and 3 (in either or both, directions), allowing a dwell time where the liquid is allowed to contact the teeth without flow.

Figure 2:
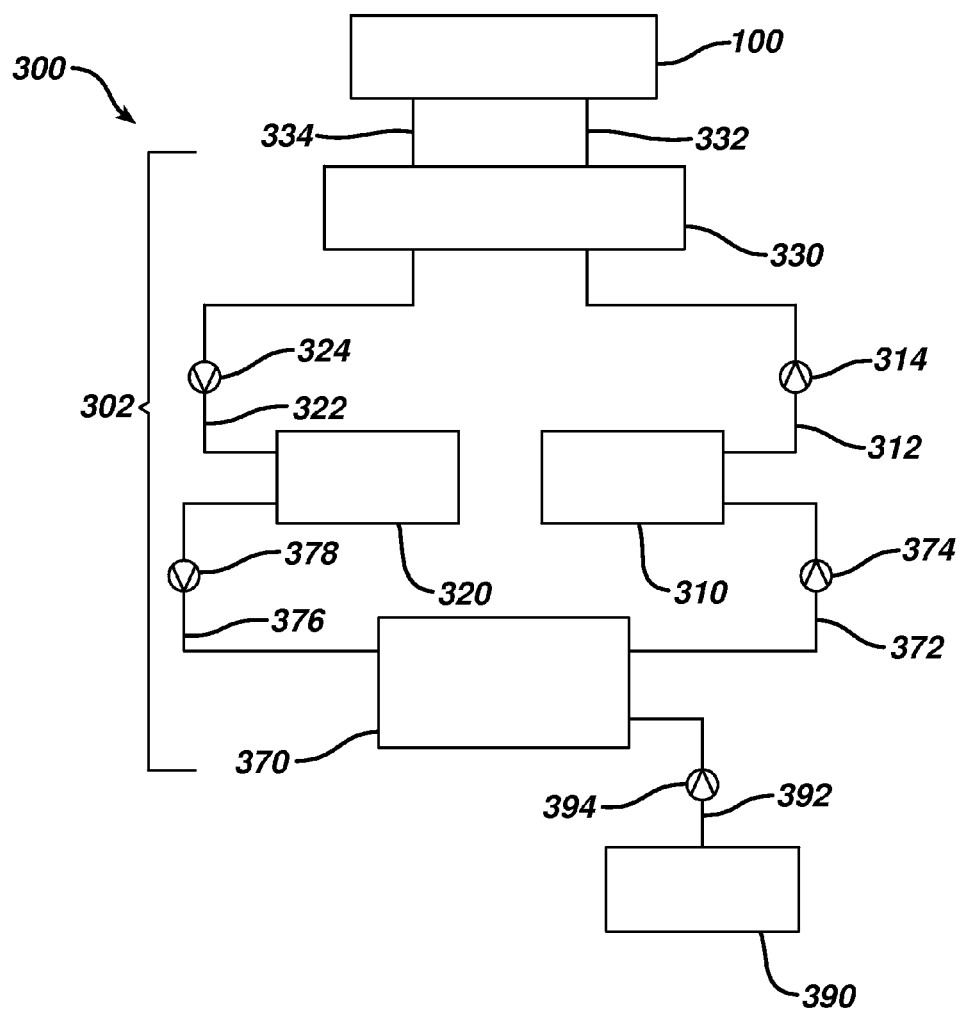
FIG. 2 is a schematic drawing of an alternative embodiment of a system according to the present invention.

FIG. 2 is a schematic drawing of a first alternative embodiment of a system according to the present invention. The figure shows system 300, with components including: means for providing reciprocation of liquid in the oral cavity 302, liquid reservoir 370, liquid supply reservoir 390, and means for directing liquid onto and about the plurality of surfaces in the oral cavity, in this instance shown as application tray 100. Means for providing reciprocation of fluids may include delivery device 310, collection device 320, reciprocating flow controller 330, tubes 312, 322, 372, 376, and 392, and solution one-way flow valves 314, 324, 374, 378, and 394. Tubes 332 and 334 provide for conveyance of the liquid from reciprocating flow controller 330 to application tray 100.

In some embodiments, delivery device 310 and collection device 320 may be individual, single action piston pump. In other embodiments, delivery device 310 and collection device 320 may be housed together as a dual action piston pump. Liquid supply reservoir 390 and liquid reservoir 370 may be made of glass, plastic or metal. Liquid supply reservoir 390 may be integral to system 300 and refillable. In some embodiments, liquid supply reservoir 390 may be a replaceable liquid supply, detachably connected to system 300.

In some embodiments, any of liquid supply reservoir 390, liquid reservoir 370, or tubes 312, 372, 392, may include a heat source to pre-warm liquid prior to direction into application tray 100 for application to the plurality of surfaces in the oral cavity. The temperature should be maintained within a range effective to provide comfort to the user during use.

Application tray 100, could be integral with, or detachably connected to cleaning reciprocating means 302 by way of tubes 332, 334, and other attachment means (not shown).

Liquid in liquid supply reservoir 390 flows through tube 392 to liquid reservoir 370. Liquid in reservoir 370 flows through tube 372 to delivery device 310. Liquid flow through tube 372 may be controlled by one-way flow valve 374. From delivery device 310, liquid flows through tube 312 to reciprocating flow controller 330. One-way flow valve 314 controls the liquid flow through tube 312. Liquid flows from reciprocating flow controller 330 to application tray 100 through tube 332 or 334, depending on the flow direction setting of flow controller 330. Liquid flows from application tray 100, through tube 334 or 332 back to reciprocating flow controller 330, and from reciprocating flow controller 330 to collection device 320, through tube 322. One-way flow valve 324 controls the liquid flow through tube 322. Finally, cleaning liquid flows from collection device 320 to liquid reservoir 370 through tube 376. One-way flow valve 378 controls the liquid flow through tube 376.

The actions of delivery device 310 and collection device 320 are controlled by a logic circuit, which may include a program to the start of the reciprocation cycle, a program to execute the reciprocation cycle, i.e. to cause solution to be reciprocated about the plurality of surfaces of the oral cavity, thereby providing the beneficial effect, a program to empty application tray 100 at the end of the reciprocation cycle, and a self-cleaning cycle to clean the system between uses, or at pre-set or automatic cleaning times.

System 300 may also include switches such as on/off, fill application tray 100, run the cleaning program, empty system 300, and clean system 300, and indicator, or display, lights including, but are not limited to, power on, charging, cycle program running, device emptying, results or feedback, and self-cleaning cycle in operation. In embodiments where liquid is pre-warmed prior to direction into application tray 100, a display light could be used to indicate that the liquid is at the proper temperature for use.

One method of using system 300 to clean teeth is as follows. Prior to use, cleaning liquid in liquid supply chamber 390 flows through tube 392 and one-way valve 394 to cleaning liquid reservoir 370. In some embodiments, liquid supply reservoir 390 is now disconnected from system 300.

In the first step, the user positions application tray 100 in the oral cavity about the teeth and gingival area. The user closes down on tray 100, thereby achieving an effective fit or seal between gums, teeth and tray 100. The user pushes a start button initiating the cleaning process. The cleaning process is as follows:

1. Delivery device 310 is activated to begin drawing cleaning liquid from cleaning liquid reservoir 370 through tube 372 and one-way flow valve 374.
2. Once delivery device 310 is sufficiently filled, delivery device 310 is activated to begin dispensing cleaning liquid to application tray 100 via tube 312, one-way valve 314, reciprocating flow controller 330, and tube 332.
3. Collection device 320 is activated sequentially to, or simultaneously with, activation of delivery device 310 to begin drawing cleaning liquid from application tray 100 via tube 334, reciprocating flow controller 330, tube 322, and one-way valve 324. Cleaning solution will be prevented from flowing through tube 372 by one-way flow valve 374. In some embodiments, delivery device 310 and collection device 320 are controlled by a logic circuit to work in concert so that an equal volumetric flow of cleaning liquid is dispensed from delivery device 310 and drawn into collection device 320.
4. Collection device 320 is activated to begin dispensing cleaning solution to cleaning liquid reservoir 370 via tube 376 and one-way valve 378. Cleaning liquid will be prevented from flowing through tube 322 by one-way flow valve 324. Delivery device 310 is also activated to begin drawing cleaning liquid from cleaning liquid reservoir 370 through tube 372 and one-way flow valve 374.
5. To reciprocate the cleaning liquid, steps 2 and 3 are repeated after the flow direction is reversed, cycling cleaning liquid between delivery/collection device 320 and application tray 100, using tubes 334 and 332, respectively.
6. To cycle cleaning liquid, steps 2 through 4 are repeated, cycling cleaning liquid between cleaning liquid reservoir 370 and application tray 100
7. The process continues to run until the time required for cleaning has expired, or the desired numbers of cycles are complete.

Figure 3:
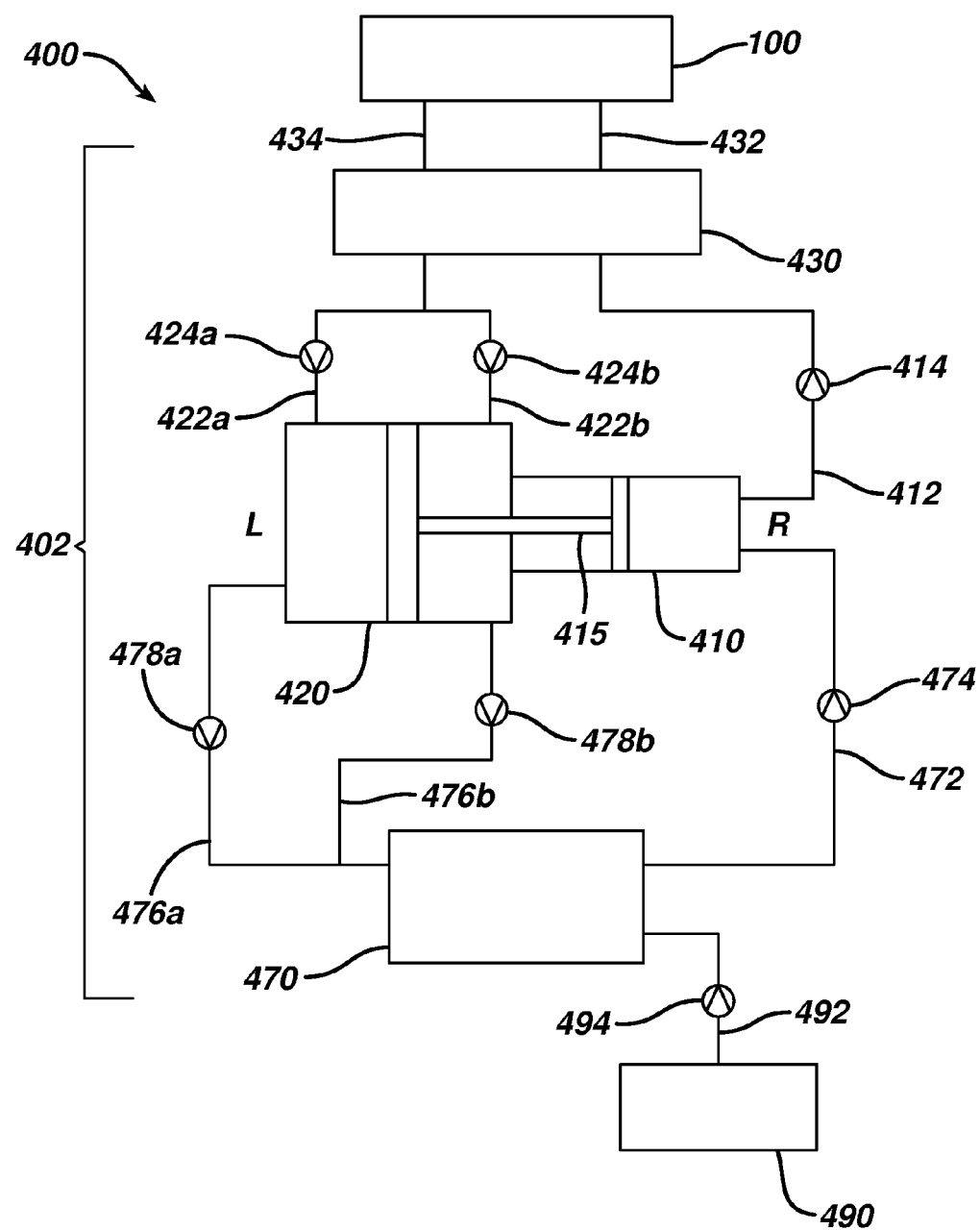
FIG. 3 is a schematic drawing of another alternative embodiment of a system according to the present invention.

FIG. 3 is a schematic drawing of a second alternative embodiment of a system according to the present invention.

The figure shows system 400, with components including: means for providing reciprocation of liquids in the oral cavity 402, liquid reservoir 470, liquid supply reservoir 490, and means for directing the liquid onto the plurality of surfaces of the oral cavity, in this instance shown as application tray 100. Means for providing reciprocation 402 may include delivery device 410, collection device 420, reciprocating flow controller 430, tubes 412, 422a, 422b, 472, 476, and 492, and solution one-way flow valves 414, 424a, 424b, 474, 478a, 478b, and 494. Tubes 432 and 434 provide for conveyance of the liquid from reciprocating flow controller 430 to application tray 100.

In the present embodiment, delivery device 410 and collection device 420 are housed together as a dual action piston pump, with common piston 415. Liquid supply reservoir 490 and liquid reservoir 470 may be made of glass, plastic, or metal. Liquid supply reservoir 490 may be integral to system 400 and refillable. In some embodiments, liquid supply chamber 490 may be a replaceable liquid supply, detachably connected to system 400.

In some embodiments, any of liquid supply chamber 490, liquid reservoir 470, or tubes 412, 472, 492, may include a heat source to pre-warm cleaning solution prior to direction into application tray 100 for application to the teeth. The temperature should be maintained within a range effective to provide comfort to the user during use.

Application tray 100 could be integral with, or detachably connected to reciprocating means 402 by way of tubes 432, 434 and other attachment means (not shown).

Liquid in liquid supply chamber 490 flows through tube 492 to liquid reservoir 470. Liquid in reservoir 470 flows through tube 472 to delivery device 410. Liquid flow through tube 472 is controlled by one-way flow valve 474. From delivery device 410, liquid flows through tube 412 to reciprocating flow controller 430. One-way flow valve 414 controls the liquid flow through tube 412. Liquid flows from reciprocating flow controller 430 to application tray 100 through tube 432 or tube 434, depending on the flow direction. Liquid flows from application tray 100, through tube 434 or tube 432, again depending on the flow direction, back to reciprocating flow controller 430, and from reciprocating flow controller 430 to collection device 420, through tubes 422a and 422b. One-way flow valves 424a and 424b control the liquid flow through the tubes. Finally, liquid flows from collection device 420 to liquid reservoir 470 through tubes 476a and 476b. One-way flow valves 478a and 478b control the liquid flow through the tubes.

The actions of delivery device 410 and collection device 420 are controlled by a logic circuit, which may include a program to the start reciprocation cycle, a program to execute the reciprocation cycle, i.e. to cause solution to be reciprocated about the plurality of the surfaces of the oral cavity, thereby providing the beneficial effect, a program to empty application tray 100 at the end of the cycle, and a self-cleaning cycle to clean the system between uses, or at pre-set or automatic cleaning times.

System 400 may also include switches such as on/off, fill application tray 100, execute cleaning process, empty system 400, and clean system 400, and indicator, or display, lights including, but are not limited to, power on, charging, reciprocation program running, device emptying, and self-cleaning cycle in operation. In embodiments where liquid is pre-warmed prior to direction into application tray 100, a display light could be used to indicate that the liquid is at the proper temperature for use.

One method of using system 400 to clean teeth is as follows. Prior to use, cleaning liquid in liquid supply reservoir 490 flows through tube 492 and one-way valve 494 to cleaning liquid reservoir 470. In some embodiments, liquid supply reservoir 490 is now disconnected from system 400.

In the first step, the user positions application tray 100 in the oral cavity about the teeth and gingival area. The user closes down on tray 100, thereby achieving an effective fit or seal between gums, teeth and tray 100. The user pushes a start button initiating the cleaning process. The cleaning process is as follows:

1. Piston 415 is activated to begin drawing cleaning liquid to delivery device 410 from cleaning liquid reservoir 470 through tube 472 and one-way flow valve 474. To accomplish this, piston 415 translates from right to left ("R" to "L" on FIG. 3).

2. Once delivery device 410 is sufficiently filled, delivery device 410 is activated to begin dispensing cleaning liquid to application tray 100 via tube 412, one-way valve 414, reciprocating flow controller 430, and tube 432. To accomplish this, piston 415 translates from left to right ("L" to "R" on FIG. 3). The "L" to "R" motion of piston 415 causes collection device 420 to begin drawing cleaning liquid from application tray 100 via tube 434, reciprocating flow controller 430, tube 422a, and one-way valve 424a. Cleaning liquid will be prevented from flowing through tubes 472 and 422a, by one-way flow valves 474 and 424b. Any excess cleaning liquid in collection device 420 will begin dispensing to cleaning liquid reservoir 470 via tube 476b and one-way valve 478b. Cleaning liquid will be prevented from flowing through tube 422b by one-way flow valve 424b.

3. To cycle cleaning solution, steps 1 and 2 are repeated, cycling cleaning liquid between cleaning solution reservoir 470 and application tray 100

4. The process continues to run until the time required for cleaning has expired, or the desired numbers of cycles are complete.

Figure 6A:
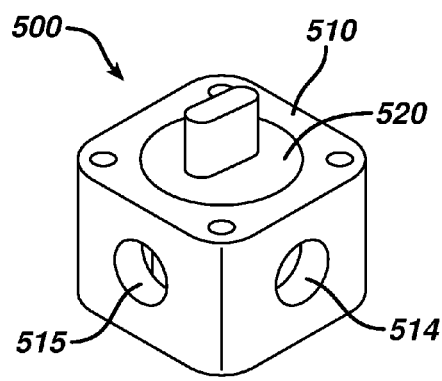
FIG. 6a is a perspective drawing of an embodiment of a reciprocating flow controller according to the present invention.
Figure 6B:
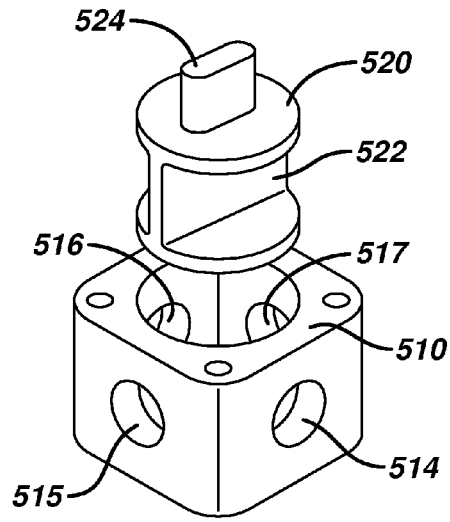

Each embodiment described in FIG. 1, FIG. 2, and FIG. 3 includes reciprocating flow controller (230, 330, 430 in FIG. 1, FIG. 2, FIG. 3, respectively). A perspective drawing and an exploded view of an embodiment of a reciprocating flow controller according to the present invention is shown in FIG. 6a and FIG. 6b, respectively. The figures show reciprocating flow controller 500 with housing 510 and flow diverter 520. Housing 510 has ports 514, 515, 516, and 517. Flow diverter 520 occupies the space defined by the inner walls of housing 510, and has panel 522 for diverting liquid flow, and position adjuster 524.

Figure 6C:
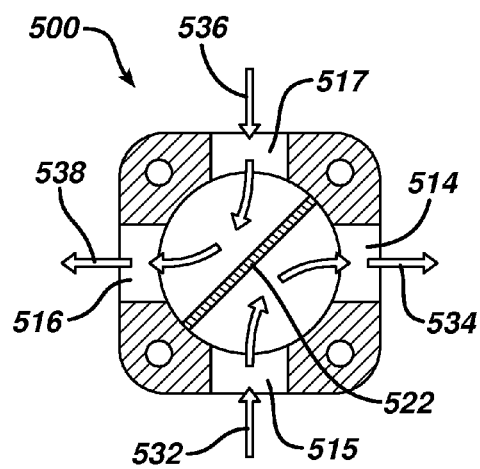
FIG. 6c is a cross-sectional view of the reciprocating flow controller of FIG. 6a in its first position.

FIG. 6c is a cross-sectional view of reciprocating flow controller 500 in its first position. In this position, incoming liquid flow 532, such as liquid in tube 212 of FIG. 1, enters reciprocating flow controller 500 through port 515. The liquid exits reciprocating flow controller 500 through port 514 as outgoing liquid flow 534, or as liquid in tube 232 of FIG. 1. Returning liquid flow 536, such as liquid in tube 234 of FIG. 1, reenters reciprocating flow controller 500 through port 517. The liquid exits reciprocating flow controller 500 through port 516 as outgoing liquid flow 538, or as liquid in tube 216 of FIG. 1.

Figure 6D:
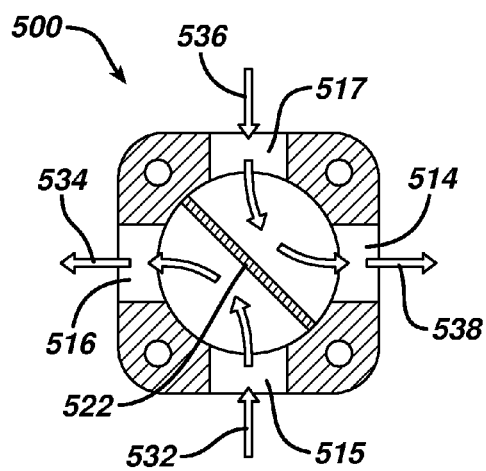
FIG. 6d is a cross-sectional view of the reciprocating flow controller of FIG. 6a in its second position.

FIG. 6d is a cross-sectional view of the reciprocating flow controller 500 in its second position. In this position, incoming liquid flow 532, such as liquid in tube 212 of FIG. 1, enters reciprocating flow controller 500 through port 515. The liquid exits reciprocating flow controller 500 through port 516 as outgoing liquid flow 534, or as liquid in tube 234 of FIG. 1. Returning liquid flow 536, such as liquid in tube 232 of FIG. 1, reenters reciprocating flow controller 500 through port 517. The liquid exits reciprocating flow controller 500 through port 514 as outgoing liquid flow 538, or as liquid in tube 216 of FIG. 1.

Reciprocation of liquid in application tray 100 of FIG. 1 is achieved by switching reciprocating flow controller 500 between its first and second positions.

A perspective drawing of a first alternative embodiment of a reciprocating flow controller according to the present invention is shown in FIG. 7a. The figure shows reciprocating flow controller 550 with housing 560, flow control block 570, and set pin 580. Housing 560 has ports 564, 565, 566, and 567. Flow control block 570 occupies the space defined by the inner walls of housing 560, and has passages, or conduits, 571, 572, 573, and 574 for diverting liquid flow.

FIG. 7b is a top view of reciprocating flow controller 550 in its first position (set pin 580 in "out" position). In first position, incoming liquid flow 592, such as liquid in tube 212 of FIG. 1, enters reciprocating flow controller 550 through port 564. The liquid flows through passage 573 of control block 570, and exits reciprocating flow controller 550 through port 566 as outgoing liquid flow 594, or as liquid in tube 232 of FIG. 1. Returning liquid flow 596, such as cleaning liquid in tube 234 of FIG. 1, reenters reciprocating flow controller 550 through port 567. The liquid flows through passage 571 of control block 570, and exits reciprocating flow controller 550 through port 565 as outgoing liquid flow 598, or as liquid in tube 216 of FIG. 1.

FIG. 7c is a top view of reciprocating flow controller 550 in its second position (set pin 580 in "in" position). In second position, incoming liquid flow 592, such as liquid in tube 212 of FIG. 1, enters reciprocating flow controller 550 through port 564. The liquid flows through passage 574 of control block 570, and exits reciprocating flow controller 550 through port 567 as outgoing liquid flow 594, or as liquid in tube 234 of FIG. 1. Returning liquid flow 596, such as liquid in tube 232 of FIG. 1, reenters reciprocating flow controller 550 through port 566. The liquid flows through passage 572 of control block 570, and exits reciprocating flow controller 550 through port 565 as outgoing liquid flow 598, or as liquid in tube 212 of FIG. 1.

Reciprocation of liquid in application tray 100 of FIG. 1 is achieved by switching reciprocating flow controller 550 between its first and second positions.

An exploded view, as well as a perspective view of a second alternative embodiment of a reciprocating flow controller according to the present invention is shown in FIG. 8a and FIG. 8b, respectively. The figures show reciprocating flow controller 610 with housing 620 and flow control barrel 630. Housing 620 has ports 621, 622, 623, and 624. Flow control barrel 630 occupies the space defined by the inner walls of housing 620, has passages 633, 634, 635, and 636 for diverting liquid flow, and position adjuster 632.

FIG. 8c is a side view of reciprocating flow controller 610 in its first position. In the first position, incoming liquid enters reciprocating flow controller 610 through port 621. The liquid flows through passage 634 of control barrel 630, and exits reciprocating flow controller 610 through port 623. Returning liquid reenters reciprocating flow controller 610 through port 624. The liquid flows through passage 633 of control barrel 630, and exits reciprocating flow controller 610 through port 622.

Though not shown, reciprocating flow controller 610 may be placed in its second position by rotating position adjuster 632 by 90°. In second position, incoming liquid enters reciprocating flow controller 610 through port 621. The liquid flows through passage 636 of control barrel 630, and exits reciprocating flow controller 610 through port 624. Returning liquid reenters reciprocating flow controller 610 through port 623. The liquid flows through passage 636 of control barrel 630, and exits reciprocating flow controller 610 through port 622.

Reciprocation of liquid in application tray 100 of FIG. 1, 2 or 3 is achieved by switching reciprocating flow controller 610 between its first and second positions.

Figure 9A:
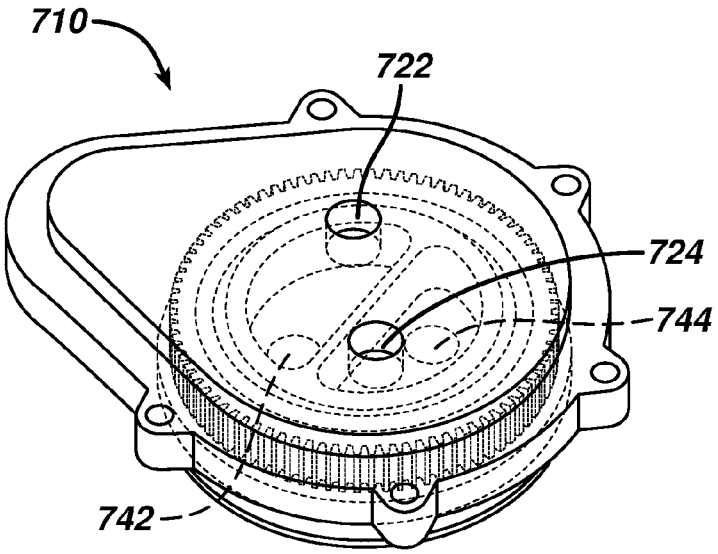
FIG. 9a is a perspective drawing of a third alternative embodiment of a reciprocating flow controller according to the present invention.
Figure 9B:
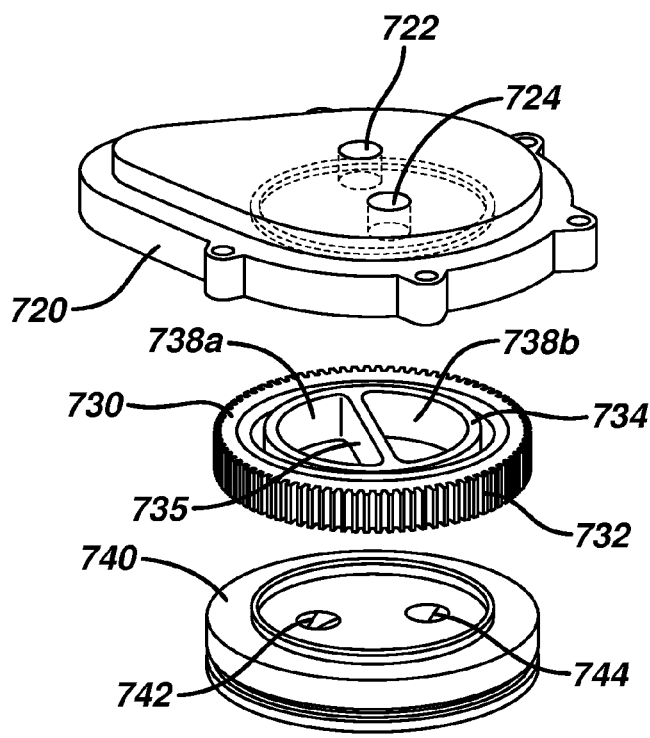

A perspective drawing and an exploded view of a third alternate embodiment of a reciprocating flow controller according to the present invention is shown in FIG. 9a and FIG. 9b, respectively. The figures show reciprocating flow controller 710 with cap 720, flow diverter disk 730, and base 740. Cap 720 has cap ports 722 and 724. Base 740 has base ports 742 and 744. Flow diverter disk 730 is disposed between cap 720 and base 740, and has panel 735 for diverting liquid flow, and position adjuster 732 in the form of a gear.

Figure 9C:
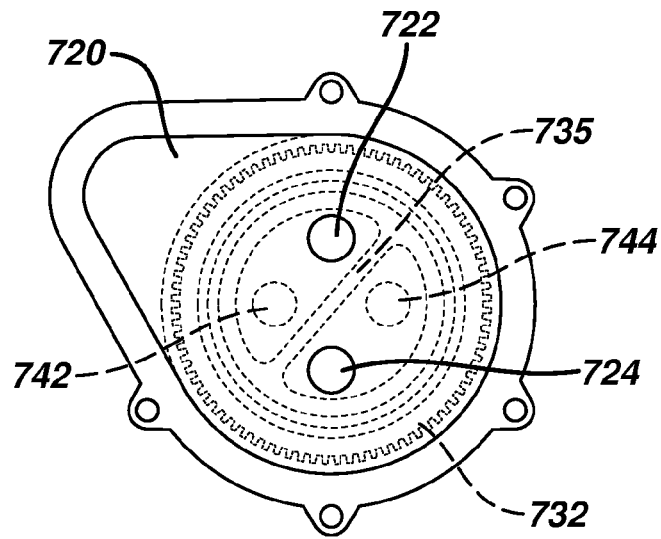
FIG. 9c is a top view of the reciprocating flow controller of FIG. 9a in its first position.

FIG. 9c is a top view of reciprocating flow controller 710 in its first position. In this position, incoming liquid, such as liquid in tube 212 of FIG. 1, enters reciprocating flow controller 710 through base port 742. The liquid exits reciprocating flow controller 710 through cap port 722, such as liquid in tube 232 of FIG. 1. Returning liquid, such as liquid in tube 234 of FIG. 1, reenters reciprocating flow controller 710 through cap port 724. The liquid exits reciprocating flow controller 710 through base port 744, such as liquid in tube 216 of FIG. 1.

Figure 9D:
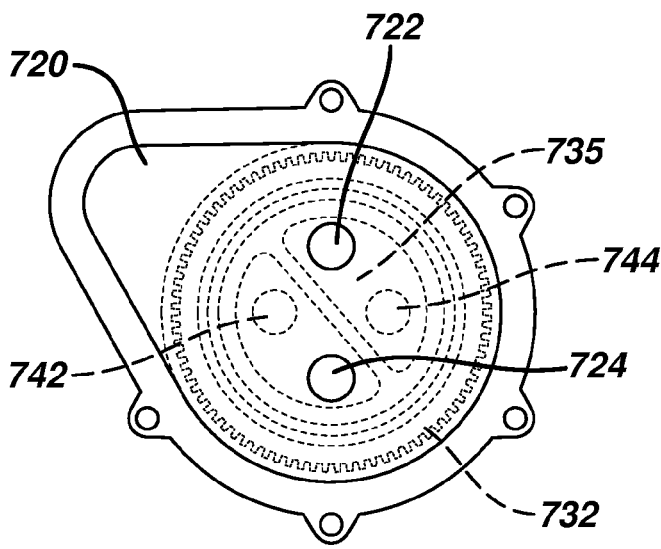
FIG. 9d is a top view of the reciprocating flow controller of FIG. 9a in its second position.

FIG. 9d is a top view of the reciprocating flow controller 710 in its second position. In this position, incoming liquid, such as liquid in tube 212 of FIG. 1, enters reciprocating flow controller 710 through base port 742. The liquid exits reciprocating flow controller 710 through cap port 724 such as liquid in tube 234 of FIG. 1. Returning liquid, such as liquid in tube 232 of FIG. 1, reenters reciprocating flow controller 710 through cap port 722. The liquid exits reciprocating flow controller 710 through base port 744, such as liquid in tube 216 of FIG. 1.

Reciprocation of liquid in application tray 100 of FIG. 1 is achieved by switching reciprocating flow controller 710 between its first and second positions. It has been found that the width of panel 735 relative to the diameters of cap ports 722 and 724 and base ports 742 and 744 is critical to the performance of reciprocating flow controller 710. If the width of panel 735 is equal to or greater than any of the diameters, then one or more of cap ports 722 and 724 or base ports 742 and 744 may be blocked, or isolated, during part of the reciprocation, resulting in suboptimal performance or device failure. A channel may be located in panel 735 to avoid this condition.

Figure 10A:
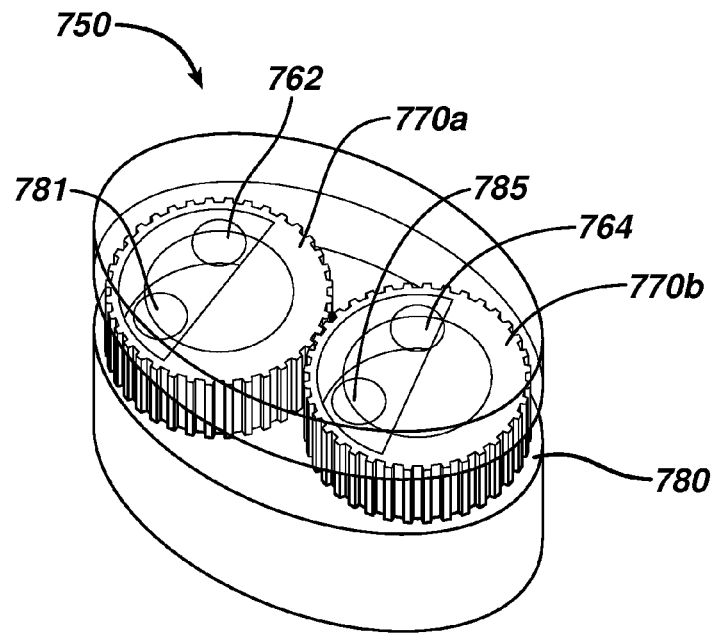
FIG. 10a is a perspective drawing of a fourth alternative embodiment of a reciprocating flow controller according to the present invention.
Figure 10B:
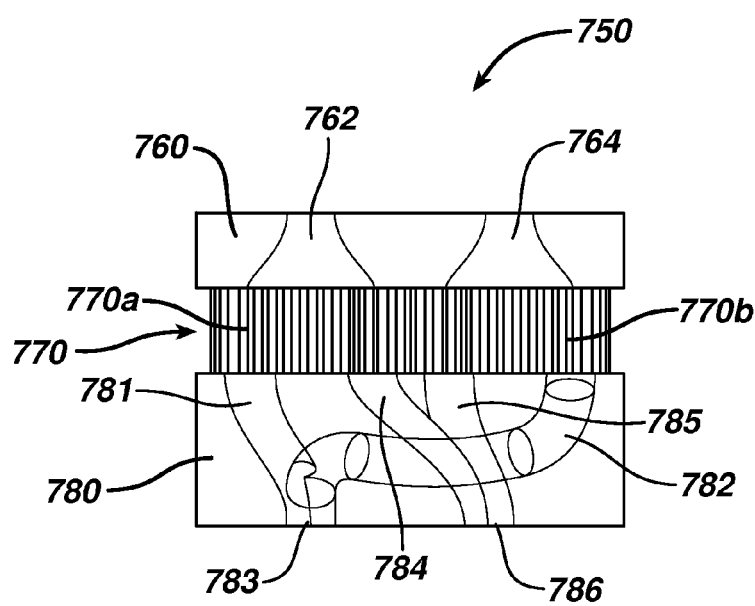

A perspective drawing and a side view of a fourth alternate embodiment of a reciprocating flow controller according to the present invention is shown in FIG. 10a and FIG. 10b, respectively. The figures show reciprocating flow controller 750 with cap 760, flow diverter 770, and base 780. Cap 760 has cap ports 762 and 764. Base 780 has base top ports 781, 782, 784, and 785, as well as base bottom ports 783 and 786. Base top ports 781 and 782 merge to form base bottom port 783, while base top ports 784 and 785 merge to form base bottom port 786. Flow diverter 770 is disposed between cap 760 and base 780, and has twin gears 770a and 770b for diverting liquid flow.

Figure 10C:
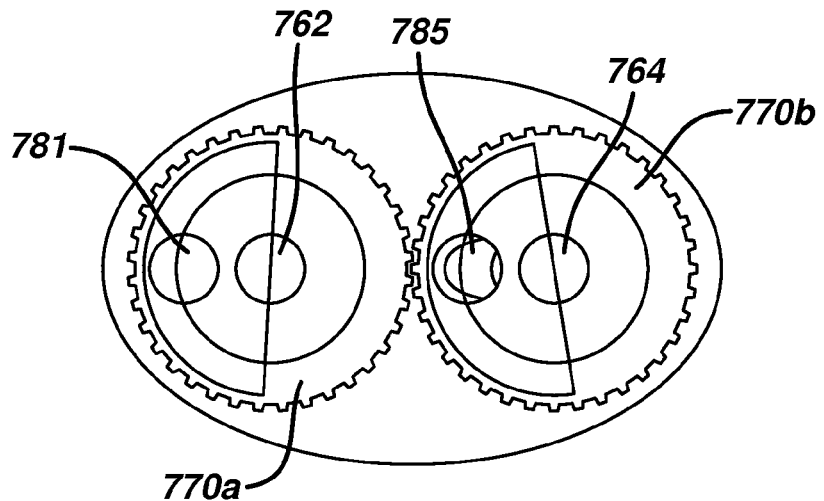
FIG. 10c is a top view of the reciprocating flow controller of FIG. 10a in its first position.

FIG. 10c is a top view of reciprocating flow controller 750 in its first position. In this position, incoming liquid, such as liquid in tube 212 of FIG. 1, enters reciprocating flow controller 750 through base bottom port 783, while base top port 784 is blocked. Gear 770a is set so that the liquid exits base 780 through base top port 781. The liquid exits reciprocating flow controller 750 through cap port 762, such as liquid in tube 232 of FIG. 1. Returning liquid, such as liquid in tube 234 of FIG. 1, reenters reciprocating flow controller 750 through cap port 764. Gear 770b is set so that the liquid enters base 780 through base top port 785. The liquid exits reciprocating flow controller 750 through base port 786, such as liquid in tube 216 of FIG. 1.

Figure 10D:
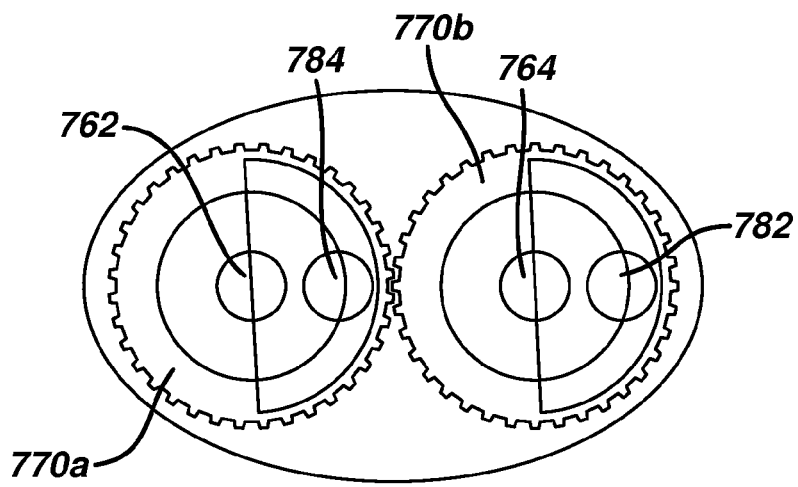
FIG. 10d is a top view of the reciprocating flow controller of FIG. 10a in its second position.

FIG. 10d is a top view the reciprocating flow controller 750 in its second position. In this position, incoming liquid, such as liquid in tube 212 of FIG. 1, enters reciprocating flow controller 750 through base port 783. Gear 770b is set so that the liquid exits base 780 through base top port 782, while base top port 785 is blocked. The liquid exits reciprocating flow controller 710 through cap port 764 such as liquid in tube 234 of FIG. 1. Returning liquid, such as liquid in tube 232 of FIG. 1, reenters reciprocating flow controller 750 through cap port 762. Gear 770a is set so that the liquid enters base 780 through base top port 784, while base top port 781 is blocked. The liquid exits reciprocating flow controller 750 through base port 786, such as liquid in tube 216 of FIG. 1.

Reciprocation of liquid in application tray 100 of FIG. 1 is achieved by switching reciprocating flow controller 750 between its first and second positions. When between the first and second positions, flow cross-over is allowed to eliminate blocked flow, which could result in sub-optimal operation or device failure.

Figure 11A:
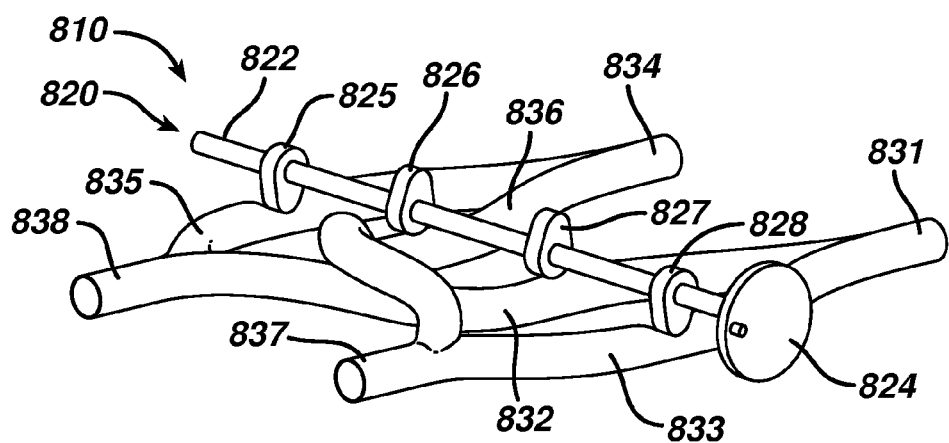
FIG. 11a is a perspective drawing of a fifth alternative embodiment of a reciprocating flow controller according to the present invention.

A perspective drawing of a fifth alternate embodiment of a reciprocating flow controller according to the present invention is shown in FIG. 11a. The figure shows reciprocating flow controller 810 with flow channels 831, 832, 833, 834, 835, 836, 837, and 838, and flow diverter 820. Flow channel 831 splits to form flow channels 832 and 833. Flow channel 834 splits to form flow channels 835 and 836. Flow channels 833 and 836 merge to form flow channel 837, flow channels 832 and 835 merge to form flow channel 838. Flow diverter 820 is disposed adjacent to flow channels 831, 832, 833, 834, 835, 836, 837, and 838, and has rod 822, driver 824, and flow control elements 825, 826, 827, and 828 for diverting liquid flow.

Figure 11B:
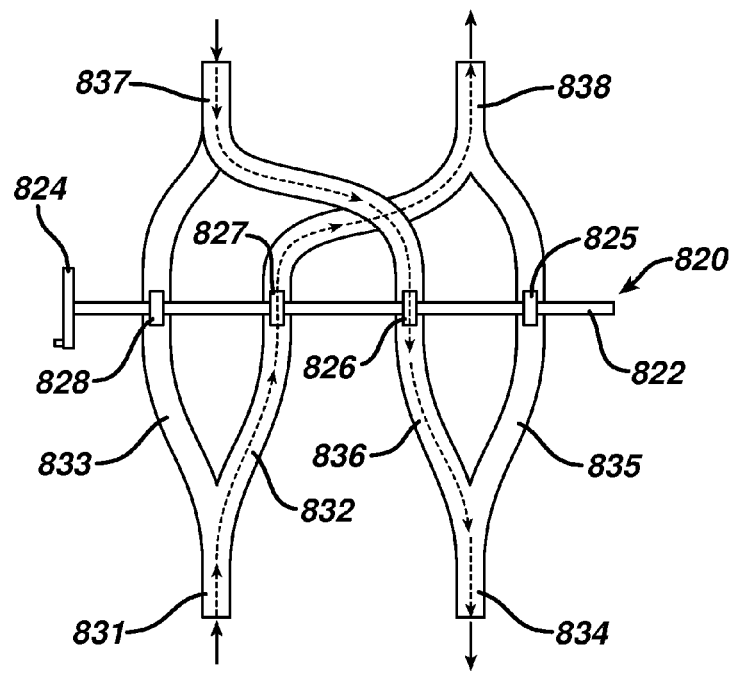
FIG. 11b is a top view of the reciprocating flow controller of FIG. 11a in its first position.

FIG. 11b is a top view of reciprocating flow controller 810 in its first position. Driver 824 is set so that flow control elements 825 and 828 prevent flow of liquid through channels 833 and 835, respectively, while flow control elements 826 and 827 allow flow through channels 836 and 832, respectively. In this position, incoming liquid, such as liquid in tube 212 of FIG. 1, enters reciprocating flow controller 810 through flow channel 831. Liquid flows through flow channel 832, and into flow channel 838. The liquid exits reciprocating flow controller 810 through flow channel 838, such as liquid in tube 232 of FIG. 1. Returning liquid, such as liquid in tube 234 of FIG. 1, reenters reciprocating flow controller 810 through liquid channel 837. Liquid flows through flow channel 836, and into flow channel 834, exiting reciprocating flow controller 810 through flow channel 834, such as liquid in tube 216 of FIG. 1.

Figure 11C:
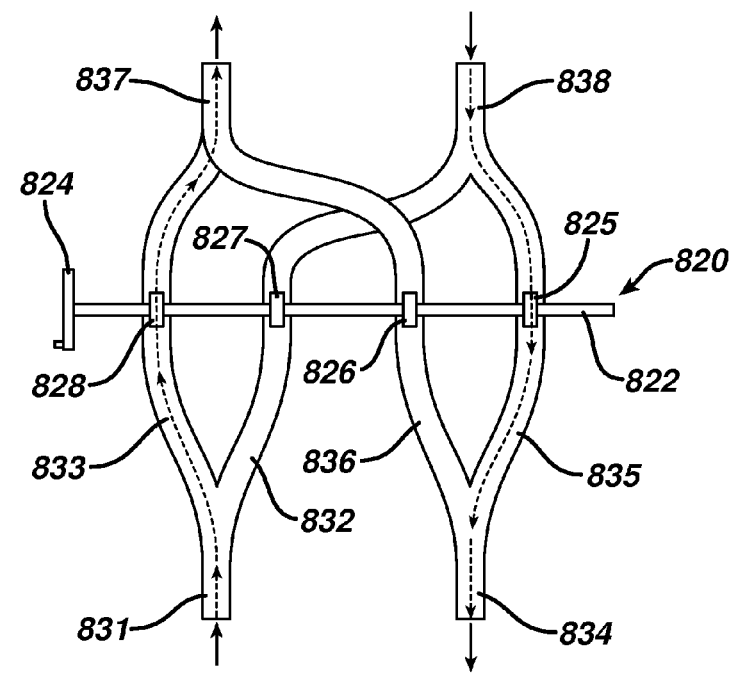
FIG. 11c is a top view of the reciprocating flow controller of FIG. 11a in its second position.

FIG. 11c is a top view of reciprocating flow controller 810 in its second position. Driver 824 is set so that flow control elements 826 and 827 prevent flow of liquid through channels 836 and 832, respectively, while flow control elements 828 and 825 allow flow through channels 833 and 835, respectively. In this position, incoming liquid, such as liquid in tube 212 of FIG. 1, enters reciprocating flow controller 810 through flow channel 831. Liquid flows through flow channel 833, and into flow channel 837. The liquid exits reciprocating flow controller 810 through flow channel 837, such as liquid in tube 234 of FIG. 1. Returning liquid, such as liquid in tube 232 of FIG. 1, reenters reciprocating flow controller 810 through liquid channel 838. Liquid flows through flow channel 835, and into flow channel 834, exiting reciprocating flow controller 810 through flow channel 834, such as liquid in tube 216 of FIG. 1.

Reciprocation of cleaning liquid in application tray 100 of FIG. 1 is achieved by switching reciprocating flow controller 810 between its first and second positions.

Figure 4:
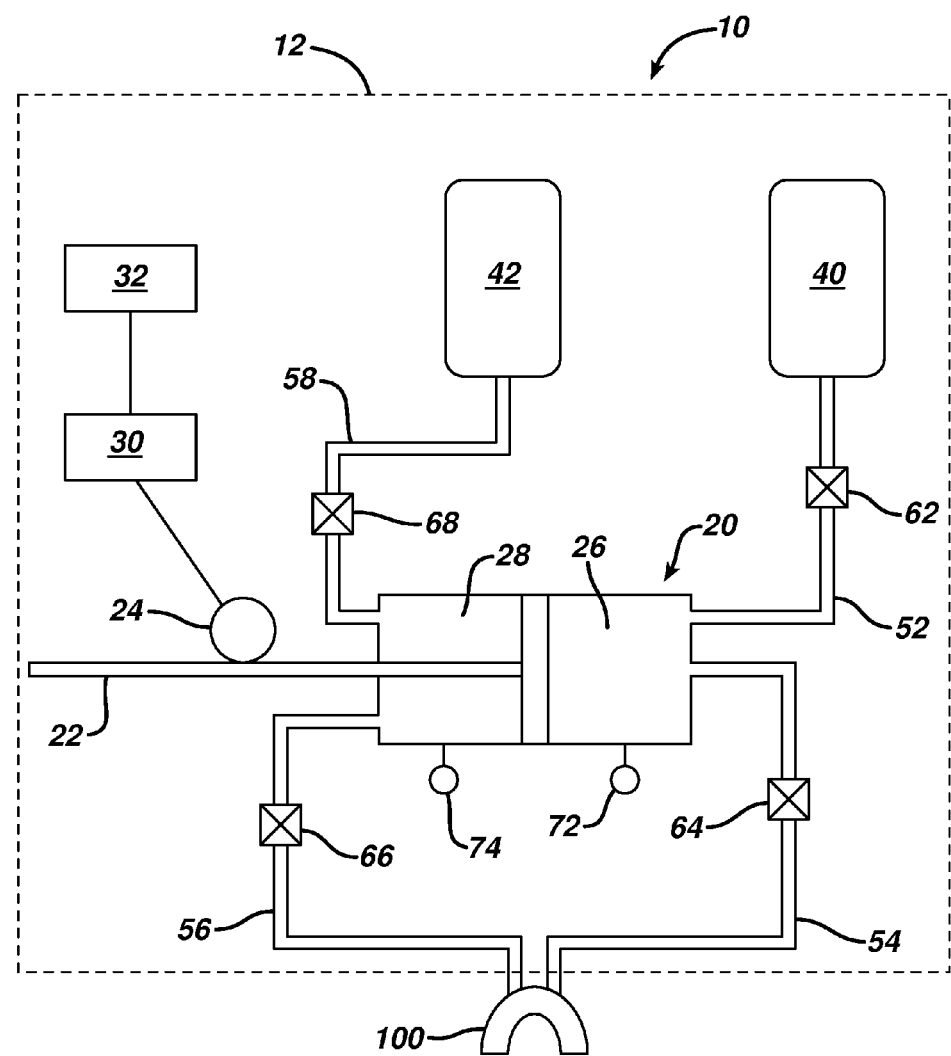
FIG. 4 is a schematic drawing of yet another alternative embodiment of a system according to the present invention.

FIG. 4 is a schematic drawing of another alternative embodiment of a system according to the present invention. As shown, system 10 includes means for directing fluid onto a plurality of surfaces of an oral cavity, in this case shown as application tray 100, and contained within housing 12, piston pump 20 with piston 22 engaged with a location sensor 24, logic circuit 30, energy supply 32, liquid supply reservoir 40, liquid retention reservoir 42, tubes 52, 54, 56, 58, liquid flow valves 62, 64, 66, 68, and pressure transducers 72, 74.

Housing 12 is capable of holding necessary components and is a means for holding necessary connectors. In embodiments where system 10 is sized to be hand-held, housing 12 mates with an electrical charging base station, both mechanically and electrically.

In the embodiment shown, pump 20 is shown in the form of a double acting piston pump, though it is conceived that a pair of single acting pumps, or other pump equivalents can be used. When the pump is a double acting piston pump, the pump includes piston 22, first chamber 26, and second chamber 28. Piston 22 is engaged with a location sensor 24. Pressure transducers 72, 74 measure the pressure in first chamber 26 and second chamber 28, respectively.

Liquid supply reservoir 40 and liquid retention reservoir 42 may be made of glass, plastic, or metal. Supply reservoir 40 may be integral to housing 12 and refillable. In some embodiments, supply chamber 40 may be a replaceable solution supply, detachably connected to housing 12. Retention reservoir 42 is used to store spent solution at the end of the cycle, e.g. cleaning cycle. Retention reservoir 42 also may include a port or other means, not shown, for discharging spent solution.

As will be discussed below, tubes 52, 54, 56, 58, and liquid flow valves 62, 64, 66, 68 connect pump 20, liquid supply chamber 40, liquid retention reservoir 42, and application tray 100.

In some embodiments, supply reservoir 40 and/or tubes 52, 54, may include a heat source to pre-warm liquid prior to direction into application tray 100 for application to plurality of surfaces in the oral cavity. The temperature should be maintained within a range effective to provide comfort to the user during use.

Energy supply 32 could be electrical, or in the form of replaceable or rechargeable batteries.

Application tray 100 could be integral with, or detachably connected to housing 12 by way of tubes 54, 56 and other attachment means (not shown). It could be one or two sided with internally, easily cleanable filters for trapping food particles. Furthermore, when applied to teeth, tray 100 will form an effective fit or seal against the gums, and includes means to direct liquid against surfaces of the oral cavity.

In use, liquid in supply reservoir 40 flows through first tube 52 to first chamber 26 of pump 20. Liquid flow through first tube 52 is controlled by first valve 62. From first chamber 26 of pump 20, liquid flows through second tube 54 to application tray 100. Second valve 64 controls the liquid flow through second tube 54. Liquid flows from application tray 100, through third tube 56, to second chamber 28 of pump 20, and is controlled by third valve 66. Second chamber 28 of pump 20 is connected to retention reservoir 42 by fourth tube 58. The flow of liquid through fourth tube 58 is controlled by fourth valve 68.

Logic circuit 30 may include a program to cause application tray 100 to be filled with liquid at the start of the cycle, a program to execute the cycle, i.e. to cause liquid to be reciprocated about the plurality of surfaces of the oral cavity, e.g. teeth and gingival area, thereby providing the beneficial effect, e.g. cleaning the teeth, a program to empty application tray 100 at the end of the cycle, and a self-cleaning cycle to clean the system between uses, or at pre-set or automatic cleaning times. Logic circuit 30 includes means to detect liquid leakage, as well as means to make-up for leakage so as to maintain a relatively constant volume of liquid during the cycle. In the embodiment shown in FIG. 4, the means to detect liquid leakage uses pressure transducers 72, 74 located in first chamber 26 and second chamber 28, respectively.

Though not shown, a face panel with a series of switches and indicator lights may also be incorporated into system 10. Switches may include, but are not limited to, on/off, fill application tray 100, run the reciprocation program, empty system 10, and clean system 10. Indicator, or display, lights include, but are not limited to power on, charging, reciprocation program running, system emptying, cleaning results or feedback and self-cleaning cycle in operation. In embodiments where cleaning solution is pre-warmed prior to direction into application tray 100, a display light could be used to indicate that the liquid is at the proper temperature for use.

One method of using system 10 to clean teeth is as follows. In the first step, the user positions application tray 100 in the oral cavity about the teeth and gingival area. The user applies pressure by closing down on tray 100, thereby achieving an effective seal between gums, teeth and tray 100. The user pushes a start button initiating loading of cleaning solution into the space between the surface of tray 100 and the teeth to be cleaned. Logic circuit 30 controls the cleaning process as follows:

1. First valve 62 opens, second valve 64 closes, piston 22 moves to its left most position drawing liquid from supply reservoir 40 through first tube 52 into first chamber 26 of pump 20.
2. First valve 62 closes, while second 64, third 66, and fourth 68 valves open. Piston 22 moves to its right most position, forcing liquid through second tube 54 to application tray 100.
3. To appropriately charge the system, steps 1 and 2 are repeated, pumping liquid as above until a pre-determined pressure is detected in both pressure transducers 72, 74, indicating that an appropriate amount of liquid is contained within chambers 26 and 28. Chambers 26 and 28 may be completely or partially filled, so long as the amount is effective to maintain reciprocating movement of the liquid through the application tray and about the plurality of surfaces of the oral cavity during use.
4. First valve 62 and fourth valve 68 close, while second valve 64 and third valve 66 remain open.
5. Piston 22 cycles from its left to right positions and back, forcing liquid to be cycled back and forth across the surfaces, e.g. teeth, in application tray 100.
6. If a loss of pressure is detected by either pressure transducer 72, or 74, steps 1 to 3 are repeated to maintain the appropriate volume of liquid in first chamber 26 and second chamber 28 of pump 20.
7. The process continues to run until the time required for achieving the beneficial effect, e.g. cleaning, has expired, the cycles are complete, or the system has cycled a number of times without pressure building-up, indicating that the liquid supply has been exhausted.

In embodiments where liquid is pre-warmed prior to entry into application tray 100, a temperature sensor is incorporated in the circuit to warn the user that the solution is too cold to use, and a method of heating the solution is provided.

Figure 5:
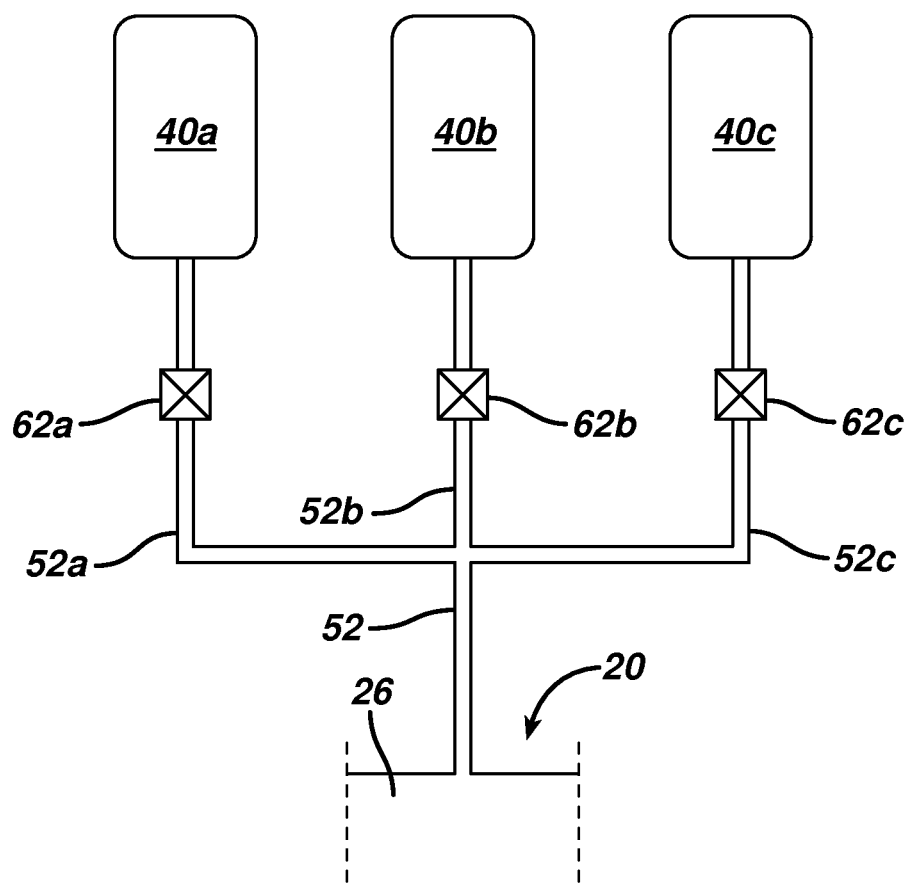
FIG. 5 is a schematic drawing of a multiple cleaning solution embodiment of a system according to the present invention.

In some embodiments, multiple liquid supplies may be utilized as shown in FIG. 5. The figure shows only the liquid supply portion of system 10 (FIG. 4). Logic circuit 30 controls the process as follows:

1. First valve 62a opens, valves 62b, 62c, and second valve 64 close, piston 22 moves to its left most position drawing liquid from supply reservoir 40a through tubes 52a and 52 into first chamber 26 of pump 20.
2. First valve 62a closes, while second 64, third 66, and fourth 68 valves open. Piston 22 moves to its right most position forcing liquid through second tube 54 to application tray 100.
3. To fully charge the system, steps 1 and 2 are repeated, pumping liquid until pressure is detected in both pressure transducers 72, 74.
4. First valve 62 and fourth valve 68 close, while second valve 64 and third valve 66 remain open.
5. Piston 22 cycles from its left to right most positions, forcing liquid to be cycled back and forth across the surfaces of the oral cavity in application tray 100.
6. If pressure is lost in either pressure transducer 72, 74, steps 1 to 3 are repeated, recharging the system when pressure is built back up in first chamber 26 and second chamber 28 of pump 20.
7. The process runs until the time is up, the cycles are complete, or the system has cycled a number of times without pressure building up indicating that the liquid has been used up.
8. First valve 62a closes, valve 62b opens, valve 62c remains closed, and steps 1 to 7 are repeated with liquid in supply reservoir 40b.
9. First valve 62a remains closed, valve 62b closes, valve 62c opens, and steps 1 to 7 are repeated with cleaning solution in liquid supply reservoir 40c.

It is important to note that this sequence can be repeated indefinitely with additional supplies of liquid in the respective supply reservoirs. In addition, the final liquid supply reservoir may contain water or other cleaning liquids and the system may be purged for cleaning.

The oral hygiene system may be comprised of several major components including, but not limited to, a base station, a hand piece for containing means for providing reciprocation of liquid about the plurality of surfaces within the oral cavity, and the application tray, or mouthpiece. The system is suitable for in-home use and adapted to direct liquid onto a plurality of surfaces of a tooth simultaneously. The device cleans teeth and removes plaque using cleaning solution that is reciprocated back and forth creating a cleaning cycle and minimizing cleaning solution used. The device could be hand held, or may be in the form of a table or counter-top device.

The base station will charge a rechargeable battery in the hand piece, hold liquid reservoirs, house diagnostic components, provide feedback to the user, and potentially clean the mouthpiece.

The hand piece will have a powered pump that will deliver liquid from the reservoir to the mouthpiece. The direction of flow may be reciprocated with liquid control valving, by a specialized pump (reversing its direction, etc), reversible check valves, or other similar means. The cycle time and flow velocity for each stage of the cycle will be variable and in some embodiments, be customized to each individual user. The hand piece will perform a filling process, and a cleaning and/or purging process. The hand piece and/or base station may provide feedback to the user for each stage of the process and potentially report diagnostic information.

The hand piece will be aesthetically pleasing and have a grip/feel comfortable for the user's hand. The weight and balance will be well suited to comfortable and efficient use while giving a high quality feel. Finger grips and/or touch points will be appropriately located for comfort, grip, feel, and assistance in proper orientation and grip location of the hand piece. The base station will also be aesthetically pleasing and allow the hand piece to easily and securely dock into position. The base station may or may not lock the hand piece into position once it's docked.

The third major component of the apparatus is the application tray, or mouthpiece.

Figure 12:
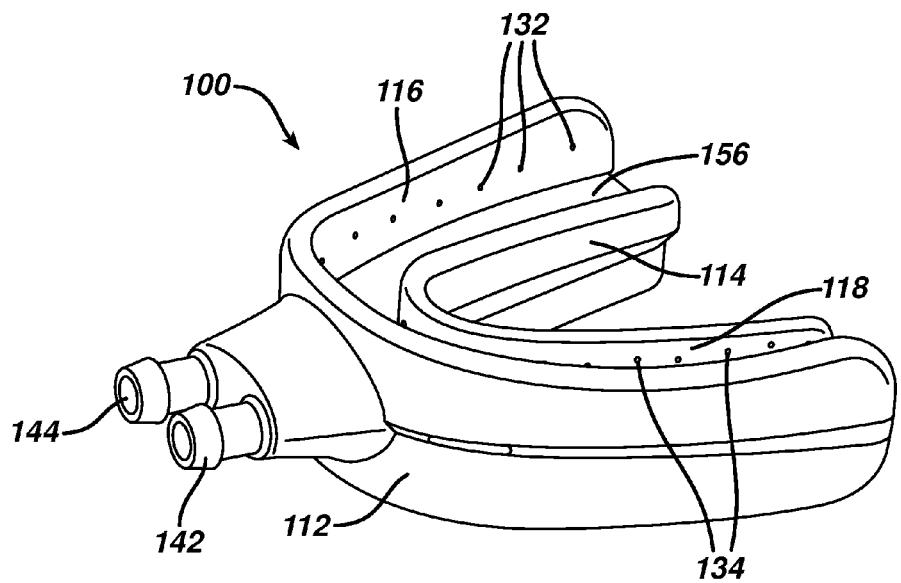
FIG. 12 is a top front perspective view of a first embodiment of an application tray for use with the present invention.
Figure 13:
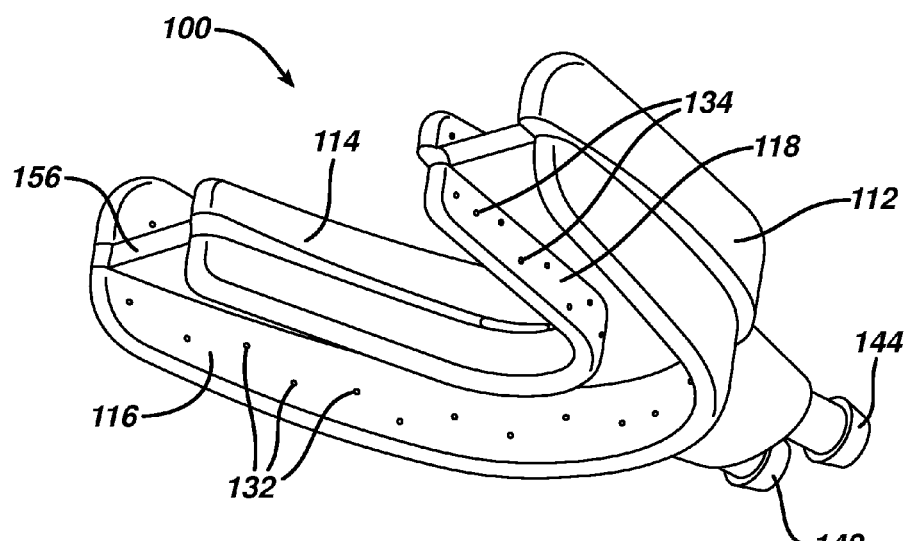
FIG. 13 is a bottom rear perspective view of the embodiment of the application tray of FIG. 12.

FIG. 12 is a top perspective view of a first embodiment of means for directing liquid onto a plurality of surfaces in the oral cavity, e.g. an application tray 100, according to the present invention. FIG. 13 is a bottom perspective view of the application tray 100 of FIG. 12. The figures show application tray 100 with outer front wall 112, outer back wall 114, inner front wall 116, inner back wall 118, and base membrane, e.g. bite plate, 156. Inner front wall jet slots 132 are located on inner front wall 116, while inner back wall jet slots 134 are located on inner back wall 118. The inner front wall jet slots 132 and inner back wall jet slots 134 shown in FIGS. 12 and 13 are only one embodiment of jet slot configuration. First port 142 and second port 144 enter application tray 100 through outer front wall 112.

FIGS. 12 and 13 depict an embodiment of an application tray 100 in which the user's top and bottom teeth and/or gingival area are substantially simultaneously contacted with liquid to provide the desired beneficial effect. It should be understood that in other embodiments, application tray 100 may be designed to clean and/or treat only the top or bottom teeth and/or gingival area of the user.

Figure 14:
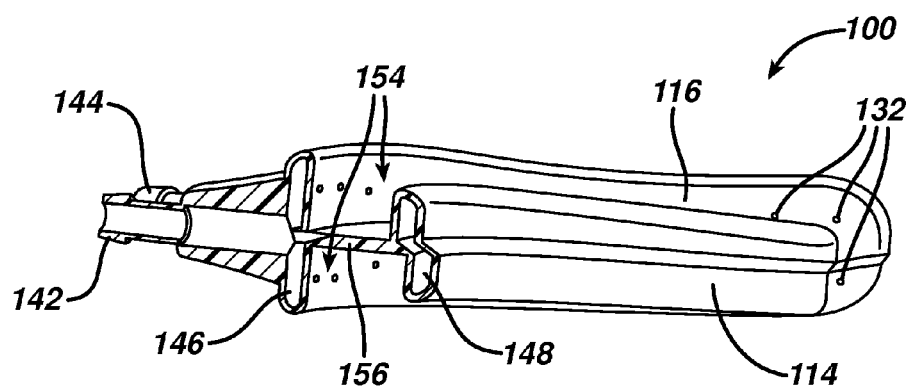
FIG. 14 is a vertical sectional view of the application tray of FIG. 12.
Figure 15:
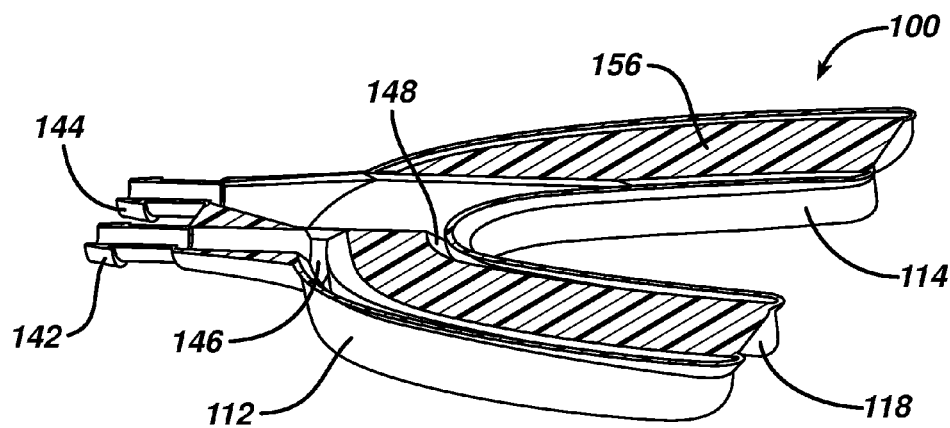
FIG. 15 is a horizontal sectional view of the application tray of FIG. 12.

FIGS. 14 and 15 are vertical and horizontal, respectively, sectional views of the application tray 100 of FIG. 12. The figures show first manifold 146, defined as the space bordered by outer front wall 112 and inner front wall 116. Second manifold 148 is defined as the space bordered by outer back wall 114 and inner back wall 118. The liquid-contacting chamber (LCC) 154 is defined by inner front wall 116, inner back wall 118, and base membrane 156.

In one embodiment of an operation, liquid enters first manifold 146 through first port 142 by pressure and then enters LCC 154 through inner front wall jet slots 132. A vacuum is pulled on second port 144 to pull the liquid through inner back wall jet slots 134, into second manifold 148 and finally into second port 144. In this embodiment, jets of liquid are first directed onto the front surfaces of the teeth and/or gingival area from one side of the LCC 154, directed through, between, and around the surfaces of the teeth and/or gingival area from the other side of LCC 154 into the second manifold to provide controlled interdental, gumline, surface and/or gingival area cleaning or treatment. Next, the flow in the manifolds is reversed. Cleaning liquid enters second manifold 148 through second port 144 by pressure and then enters LCC 154 through inner back wall jet slots 134. A vacuum is pulled on first port 142 to pull the liquid through inner front wall jet slots 132, into first manifold 146 and finally into first port 142. In the second portion of this embodiment, jets of liquid are directed onto the back surfaces of the teeth and/or gingival area, and directed through, between, and around the surfaces of the teeth and/or gingival area. The alternating of pressure/vacuum through a number of cycles creates a turbulent, repeatable and reversible flow to provide reciprocation of liquid about the plurality of surfaces of the oral cavity to substantially simultaneously contact the surfaces of the oral cavity with liquid, thereby providing the desired beneficial effect.

In another embodiment it may be preferable to deliver the liquid through one or both manifolds simultaneously, flooding LCC 154, submerging the teeth for a period of time and then evacuating the LCC after a set period of time through one or both manifolds. Here, cleaning or treating liquid simultaneously enters first manifold 146 through first port 142, and second manifold 148 through second port 144 by pressure and then enters LCC 154 simultaneously through inner front wall jet slots 132 and inner back wall jet slots 134. To evacuate LCC 154, a vacuum is simultaneously pulled on first manifold 146 through first port 142, and second manifold 148 through second port 144. Cleaning or treatment liquid is pulled through inner front wall jet slots 132 and inner back wall jet slots 134, into first manifold 146 and second manifold 148.

It is also possible to deliver different liquid compositions to first manifold 146 and second manifold 148. The different liquid compositions could then combine in the LCC for improved cleaning efficacy or treatment effects.

Figure 16:
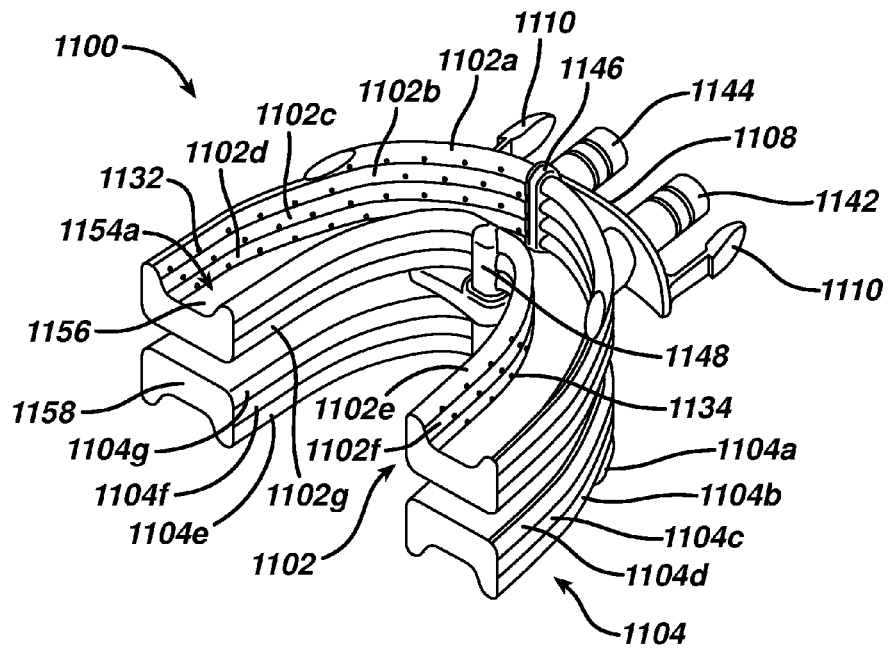
FIG. 16 is a top back perspective view of a second embodiment of an application tray for use with the present invention.
Figure 17:
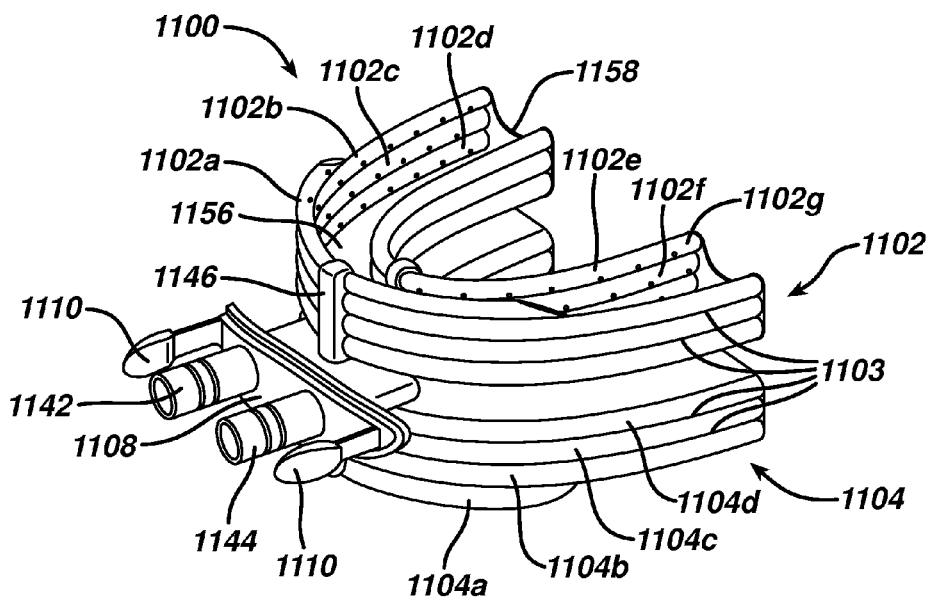
FIG. 17 is a top front perspective view of the embodiment of the application tray of FIG. 16.
Figure 18:
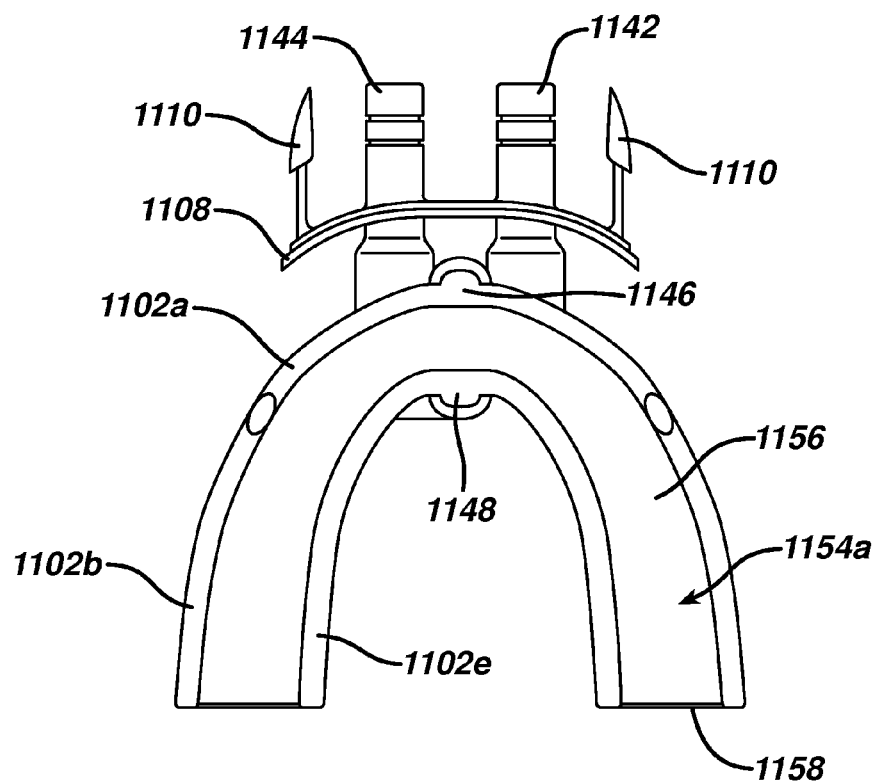
FIG. 18 is a top view of the application tray of FIG. 16.

FIG. 16 is a top, rear perspective view of a second embodiment of an application tray 1100 according to the present invention. FIG. 17 is a top, front perspective view of the application tray 1100 of FIG. 16, while FIG. 18 is a top view of the application tray of FIG. 16. The figures show application tray 1100 with top piece 1102, bottom piece 1104, first port 1142, second port 1144, and support plate 1108 fixedly attached to the front of said application tray. First port 1142 and second port 1144 enter application tray 1100 and extend through support plate 1108.

Optional quick disconnect structures, e.g. barbs, 1110 are attached to support plate 1108, allowing application tray 1100 to be quickly and easily attached to and then disconnected from means for providing liquid to the application tray, such as may be contained in housing 12 of device 10, as shown in FIG. 4. The housing would include structure effective to receive such quick disconnect barbs, or similar quick disconnect structure, in attachable engagement, to detachably connect the application tray to the housing. The quick disconnect option could be used to replace used or worn application trays, or to change application trays for different users. In some embodiments, a single user may change application trays to change the flow characteristics for different options, such as number of cleaning nozzles, nozzle velocity, spray pattern, and locations, coverage area, etc.

FIGS. 16 to 19 depict an embodiment of an application tray 1100 in which the user's top and bottom teeth and/or gingival area are substantially simultaneously contacted with liquid. It should be understood that in other embodiments, application tray 1100 may be designed to contact only the top or bottom teeth or gingival area of the user with liquid.

Top piece 1102 has front liquid lumens 1102a, 1102b, 1102c, and 1102d, back liquid lumens 1102e, 1102f, and 1102g, first manifold 1146, second manifold 1148, base membrane 1156, and back gum-sealing membrane 1158. Front liquid lumens 1102a, 1102b, 1102c, and 1102d are all connected by first manifold 1146, and optionally (as shown on FIGS. 16 to 19), connected to each other along all, or part of, their length. Likewise, back liquid lumens 1102e, 1102f, and 1102g, are all connected by second manifold 1148, and optionally, connected to each other along all, or part of, their length.

Bottom piece 1104, may be a mirror image of top piece 1102, and has front liquid lumens 1104a, 1104b, 1104c, and 1104d, back liquid lumens 1104e, 1104f, and 1104g, first manifold 1146, second manifold 1148, base membrane 1156, and back gum-sealing membrane 1158. Front liquid lumens 1104a, 1104b, 1104c, and 1104d are all connected by first manifold 1146, and optionally (as shown on FIGS. 16 to 19), connected to each other along all, or part of, their length. Likewise, back liquid lumens 1104e, 1104f, and 1104g, are all connected by second manifold 1148, and optionally, connected to each other along all, or part of, their length.

Though FIGS. 16 and 17 show top piece 1102 with four front liquid lumens (1102a, 1102b, 1102c, and 1102d) and three back liquid lumens (1102e, 1102f, and 1102g), top piece 1102 may also be formed with two, three, five, six, or even seven front or back liquid lumens. Likewise, bottom piece 1104 is shown with four front liquid lumens (1104a, 1104b, 1104c, and 1104d) and three back liquid lumens (1104e, 1104f, and 1104g), bottom piece 1104 may also be formed with two, three, five, six, or even seven front or back liquid lumens.

The liquid-contacting chamber ((LCC) 1154a, mentioned above, is located in top piece 1102, defined by front liquid lumens (1102a, 1102b, 1102c, and 1102d), back liquid lumens (1102e, 1102f, and 1102g), base membrane 1156, and back gum-sealing membrane 1158. Though not shown, bottom piece 1104 also has a LCC 1154b, defined by front liquid lumens (1104a, 1104b, 1104c, and 1104d), back liquid lumens (1104e, 1104f, and 1104g), base membrane 1156, and back gum-sealing membrane 1158.

The multi-lumen design provides bidirectional or dedicated lumens for flow and vacuum that are self-reinforcing and therefore do not collapse under vacuum or rupture under pressure while in use, maximizing the structural integrity, while minimizing the size of the overall application tray 1100 for user comfort during insertion, in-use, and upon removal. This decreased size also serves to provide an enhanced effective seal of the application tray in the oral cavity.

If the multiple lumens (1102a, 1102b, 1102c, 1102d, 1102e, 1102f, 1102g, 1104a, 1104b, 1104c, 1104d, 1104e, 1104f, and 1104g) are connected as described above, they form a lumen hinge sections (1103 on FIG. 17). This may result in the multi-lumen design providing conformance in the X, Y and Z directions, due to the flexibility of lumen hinge sections 1103 between each lumen. This design allows effective and feasible conformance to a variety of different users teeth and gum topography, providing the effective gum sealing without irritating the gums and allowing dynamic positioning of the liquid cleaning jets around each of the teeth to obtain proximal and interdental cleaning action. The multiple lumens are also attached to the first manifold 1146 and second manifold 1148. This creates a secondary flexible joint providing two additional degrees of motion for the adjusting to different bite architectures that may be encountered.

The back gum-sealing membrane 1158 proves a flexible and universal sealing mechanism to minimize leakage into the oral cavity while redirecting flow onto and around teeth, to maximize treatment/cleaning area to get to hard-to-reach-places (HTRP). The membrane can provide an elastic function across the lumen longitudinal axis to form around the teeth and gums.

Base membrane 1156 provides the flexibility required for effective fit or sealing within the oral cavity and allowing redirection and flow of jets back towards the teeth and/or gingival surfaces.

Optionally, application tray 1100 could also include gum-sealing component if required, which could be attached to the front liquid lumens 1102a, 1102b, 1104a, and 1104b, and back liquid lumens 1102e and 1104e (member furthest from teeth).

Optionally, frictional elements, such as filament tufts, could also be placed or secured through any of the lumen hinge sections 1103 without significantly increasing the size of application tray 1100, or impacting user comfort or liquid flow in the application tray 1100.

Inner front wall jet slots 1132 are located on inner front wall of top piece 1102 and bottom piece 1104, while inner back wall jet slots 1134 are located on inner back wall of top piece 1102 and bottom piece 1104. Though only one inner front wall jet slot 1132 and inner back wall jet slot 1134 are shown in FIGS. 13 to 16, the number, shape and size of inner front wall jet slots 1132 and inner back wall jet slots 1134 affect the cleaning of the teeth and gums, and can be designed to direct jets of cleaning liquid in a variety of spray patterns. The inner front wall jet slots 1132 and inner back wall jet slots 1134 shown in FIGS. 16 to 19 are only one embodiment of jet slot configuration.

FIGS. 16 and 17 depict an embodiment of an application tray 1100 in which surfaces of the users top and bottom teeth and/or gingival area are substantially simultaneously contacted by liquid to provide the desired beneficial effect. It should be understood that, in other embodiments, application tray 1100 may be designed to contact only the top or bottom teeth and/or gingival area of the user.

Figure 19:
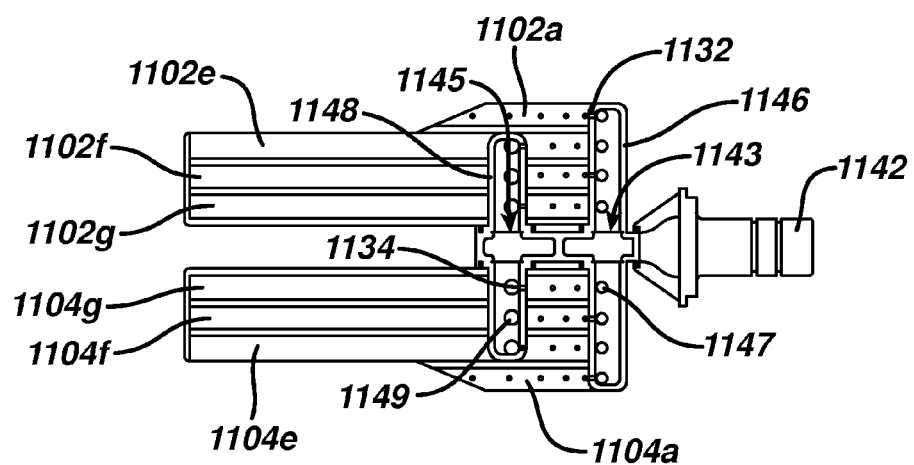
FIG. 19 is a cut-away view of the application tray of FIG. 16.

FIG. 19 is a cut-away view of the application tray 1100 of FIG. 16. The figure shows first manifold 1146 and second manifold 1148. In one embodiment of a cleaning operation, cleaning liquid is pumped through first port 1142, and enters first manifold 1146 through first flow diverter 1143. Liquid enters front liquid lumens 1102a, 1102b, 1102c, 1102d, 1104a, 1104b, 1104c and 1104d through front liquid lumen ports 1147. The cleaning liquid then enters LCCs 1154a and 1154b through inner front wall jet slots 1132. A vacuum is pulled on second manifold feeder 1144 to pull the cleaning liquid through inner back wall jet slots 1134, into back liquid lumens 1102e, 1102f, 1102g, 1104e, 1104f, and 1104g. The liquid enters second manifold 1148 through back liquid lumen ports 1149, then through second flow diverter 1145, and finally into second manifold feeder 1144.

In this embodiment, jets of cleaning liquid are first directed from first manifold 1146 to the front surfaces of the teeth and/or gingival area from one side of the LCC, directed through, between, and around the surfaces of the teeth and/or gingival area from the other side of the LCC into the second manifold 1148 to provide controlled interdental, gumline, surface and/or gingival area cleaning or treatment.

Next, the flow in the manifolds is reversed. Cleaning liquid is pumped through second port 1144, and enters second manifold 1148 through second flow diverter 1145. Liquid enters back liquid lumens 1102e, 1102f, 1102g, 1104e, 1104f, and 1104g through back liquid lumen ports 1149. The cleaning liquid then enters LCCs 1154a and 1154b through inner back wall jet slots 1134. A vacuum is pulled on first port 1142 to pull the cleaning liquid through inner front wall jet slots 1132, into front liquid lumens 1102a, 1102b, 1102c, 1102d, 1104a, 1104b, 1104c and 1104d. The liquid enters first manifold 1146 through front liquid lumen ports 1147, then through first flow diverter 1143, and finally into first port 1144.

In the second portion of this embodiment, jets of cleaning liquid are directed onto the back surfaces of the teeth and/or gingival area, and directed through, between, and around surfaces of the teeth and/or gingival area. The alternating of pressure/vacuum through a number of cycles creates a turbulent, repeatable and reversible flow to provide reciprocation of liquid about the plurality of surfaces of the oral cavity to substantially simultaneously contact the surfaces of the oral cavity with liquid, thereby providing the desired beneficial effect.

In another embodiment it may be preferable to deliver the liquid through one or both manifolds simultaneously, flooding LLCs 1154a and 1154b, submerging the teeth for a period of time and then evacuating the LCCs after a set period of time through one or both manifolds. Here, cleaning or treating liquid is simultaneously pumped through first port 1142 into first manifold 1146 via first flow diverter 1143, and through second port 1144 into second manifold 1148 via second flow diverter 1145. Liquid then simultaneously enters front liquid lumens 1102a, 1102b, 1102c, 1102d, 1104a, 1104b, 1104c and 1104d through front liquid lumen ports 1147, and back liquid lumens 1102e, 1102f, 1102g, 1104e, 1104f, and 1104g through back liquid lumen ports 1149. The cleaning liquid then enters LCCs 1154a and 1154b through inner front wall jet slots 1132 and inner back wall jet slots 1134. To evacuate the LCCs, a vacuum is simultaneously pulled on first manifold 1146 through first port 1142, and second manifold 1148 through second port 1144. Cleaning or treatment liquid is pulled through inner front wall jet slots 1132 and inner back wall jet slots 1134, into first manifold 146 and second manifold 148.

It is also possible to deliver different liquid compositions to first manifold 1146 and second manifold 1148. The different liquid compositions would then combine in the LCC for improved cleaning efficacy or treatment effects. In the dual manifold design it may be preferable to supply each manifold from a separate liquid supply reservoir, such as in a dual action piston pump configuration, where one supply line connects to supply first manifold 1146 and the other piston supply line provides and removes liquid from second manifold 1148, e.g. when one manifold is being supplied with liquid the second manifold is removing liquid, and vice versa.

In other embodiments, valves can be placed at front liquid lumen ports 1147 of front liquid lumens 1102a, 1102b, 1102c, 1102d, 1104a, 1104b, 1104c and 1104d, or at back liquid lumen ports 1149 of back liquid lumens 1102e, 1102f, 1102g, 1104e, 1104f, and 1104g to provide improved function by allowing lumens to engage at different times (at different points in the cleaning/treatment cycle), at pulsed intervals. As an example, in one embodiment, not all lumens engage in the liquid pumping/vacuum function. Here, front liquid lumens 1102a and 1104a, and back liquid lumens 1102e and 1104e, which primarily engage the gums, only engage in the liquid vacuum function. This would help prevent liquid from leaking into the oral cavity. Valving also allows for variable flow, allowing a decreased resistance to the liquid vacuum function, or allowing increased pumping, and therefore liquid velocity, during liquid delivery.

In still other embodiments, individual inner front wall jet slots 1132 or inner back wall jet slots 1134 may have integrated one-way valves, such as duckbill valves or umbrella valves, to allow flow only in one direction out of those particular jets. This may be effective to increase vacuum relative to pressure/delivery in the LCC.

In some embodiments, the motion of the frictional elements discussed above, relative to the teeth, could be applied by a single or combination of mechanisms including, by not limited to, the liquid (via the jet slots or via turbulence of flow); movement of the membrane via the pulsing of the flexible application tray 1100; an external vibrational mechanism to vibrate the frictional elements; linear and or rotational movement of the application tray 1100 around the teeth through user jaw motion or external driving means.

In other embodiments, a conformable substance, such as gel, may be disposed near the back gum-sealing membrane 1158, allowing application tray 1100 to comfortably fit against the back of the mouth. Alternatively, the end of application tray 1100 may have a mechanism or attachment to extend or decrease the length of the mouthpiece to the proper length for each individual user, providing a semi-custom fit.

Manufacturing of the multi-lumen design is feasible utilizing existing available manufacturing and assembly processes such as extrusion, injection, vacuum, blow, or compression molding. Other feasible techniques include rapid prototyping techniques such as 3D printing and other additive techniques, as well as subtractive techniques.

The application tray may be custom manufactured for each individual user, or customizable by the individual user prior to use. For custom manufacture of the application tray, vacuum form molds can be created directly or indirectly from user teeth and gingival impressions, which create a model of the teeth which can then be modified to create required clearances and flow channels. These vacuum form molds can be created at low cost utilizing CAD and rapid prototyping processes.

One manufacturing method is to create individual component shells through vacuum forming. Low cost methods allow vacuuming forming of very thin wall structures. The component geometry is designed to provide the interlocking features and structural geometry to allow minimization of the size of the application tray. When assembled, the manufactured components form the necessary manifolds and flow structure (bidirectional and/or dedicated manifolds) to provide the required performance characteristics for treating/cleaning the teeth.

Customized mouthpieces are based on the user's teeth geometry, therefore creating a consistent distance between the mouthpiece and teeth may provide a more consistent cleaning/treating experience. The materials for each of the two-piece shell may be different, therefore allowing for softer material (on the inside shell) where it contacts teeth/gums and harder material on the outside shell to maintain rigidity and the overall shape.

For customizable application trays, tray pre-forms (similar to sport mouth guards or teeth grinding appliances) containing pre-manufactured manifolds, nozzles and channels are mass manufactured. The tray pre-forms can be created through a variety of known manufacturing techniques including, but not limited to, blow molding, vacuum forming, injection and/or compression molding. The material used in the pre-form would be a low temperature deformable plastic material. The pre-form would be used in conjunction with required spacers to be applied over the teeth to provide required clearance, cleaning and/or treatment performance. Once the clearance components are applied to the teeth, the pre-form would be heated via microwave or by placing in boiling water so as to be pliable. The pliable pre-form would be applied onto the user's teeth and gingival area to create the customized application tray.

The application tray can be integrated with stressing features to allow elastic conformance to maximize positioning, comfort and performance during application and in use. For example, spring-like elements such as shins, clips and elastic bands may provide fitting over and against gums.

Materials for the MP lumen could range from lower durometer flexible materials (25 shore A) to harder materials more rigid materials (90 shore A), preferably being between 40 and 70 shore A.

Materials could be silicone, thermoplastic elastomer (TPE), polypropylene (PP), polyethylene (PE), polyethylene terephthalate (PET), ethylene vinyl acetate (EVA), polyurethane (PU), or multi-component (combination of materials and hardness) to achieve desired design and performance attributes.

The jet openings or slots could be made through a secondary operation such as drilling or punching, or formed during molding. Alternatively, the jet openings or slots could be inserted into the application tray to provide increased wear and or different jet performance characteristics, and could be combined with frictional cleaning elements or other components to enhance the cleaning and/or treatment affect.

FIGS. 20 to 23 depict an embodiment of an application tray 1200 in which only the user's top or bottom teeth and gingival area are contacted with liquid. It should be understood that in other embodiments, application tray 1200 may be designed to substantially simultaneously contact both the top and bottom teeth and gingival area of the user, as depicted elsewhere herein.

Figure 20:
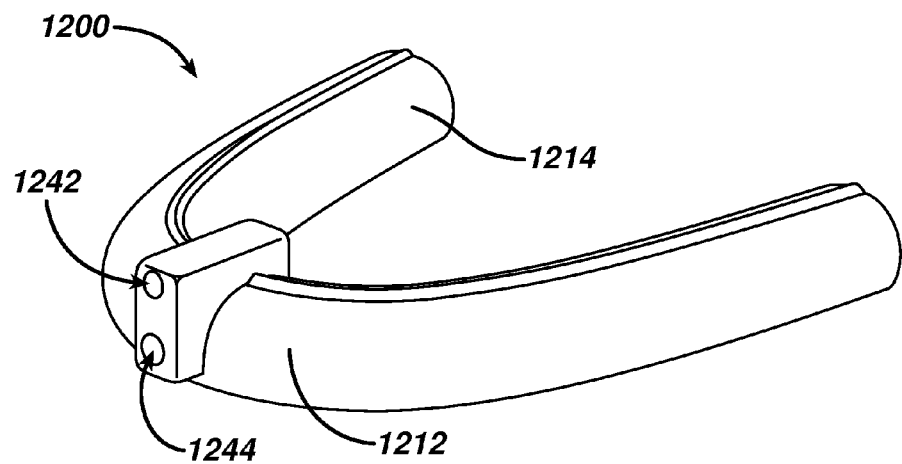
FIG. 20 is a top front perspective view of a third embodiment of an application tray for use with the present invention.
Figure 21:
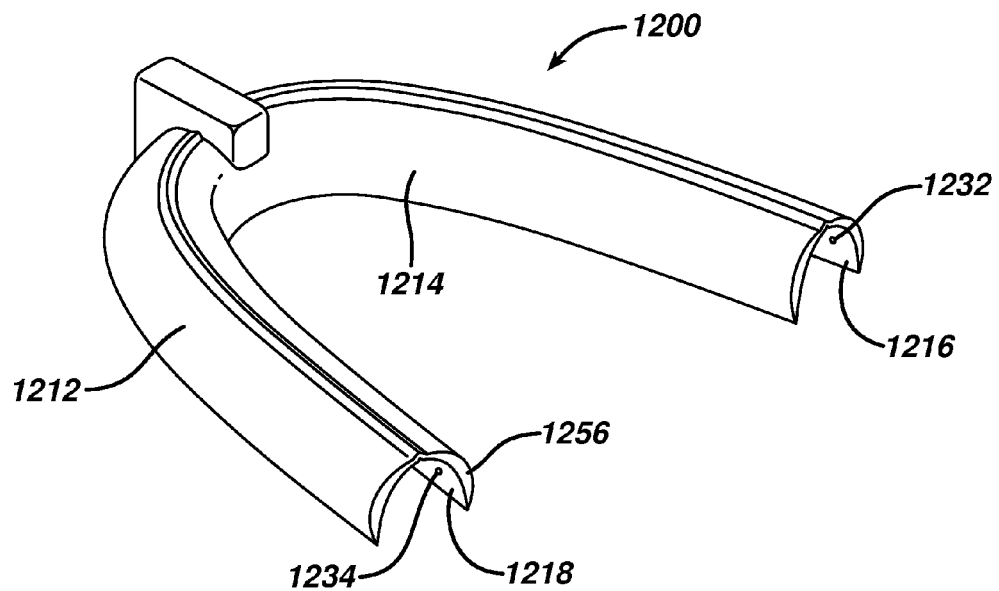
FIG. 21 is a top back view of the embodiment of the application tray of FIG. 20.
Figure 22:
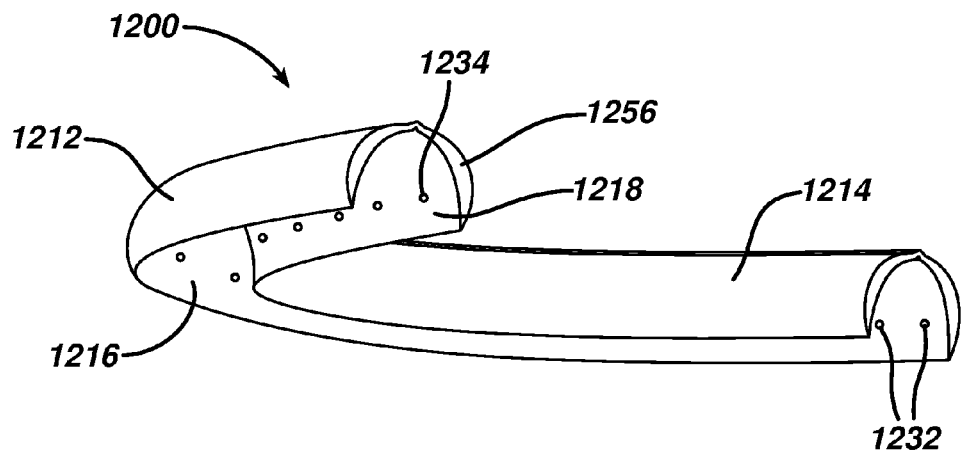
FIG. 22 is a bottom back view of the embodiment of the application tray of FIG. 20.

FIG. 20 is a top front perspective view of a third embodiment of an application tray 1200 according to the present invention. FIG. 21 is a top back view of the embodiment of the application tray 1200 of FIG. 20, while FIG. 22 is a bottom back view of the application tray 1200 of FIG. 20. The figures show application tray 1200 with outer front wall 1212, outer back wall 1214, inner front wall 1216, and inner back wall 1218. Inner front wall jet slots 1232 are located on inner front wall 1216, while inner back wall jet slots 1234 are located on inner back wall 1218. First port 1244 and second port 1242 enter application tray 1200 through outer front wall 1212.

The number and location of inner front wall jet slot 1232 and inner back wall jet slot 1234 as shown in FIGS. 20 to 23 is exemplary and is not intended to limit the scope of the application tray. The actual number, shape and size of inner front wall jet slots 1232 and inner back wall jet slots 1234 affect the cleaning of the teeth and gums, and can be selected or designed to direct jets of cleaning liquid in a variety of spray patterns. The inner front wall jet slots 1232 and inner back wall jet slots 1234 shown in FIGS. 20 to 22 are only one embodiment of jet slot configuration.

Figure 23:
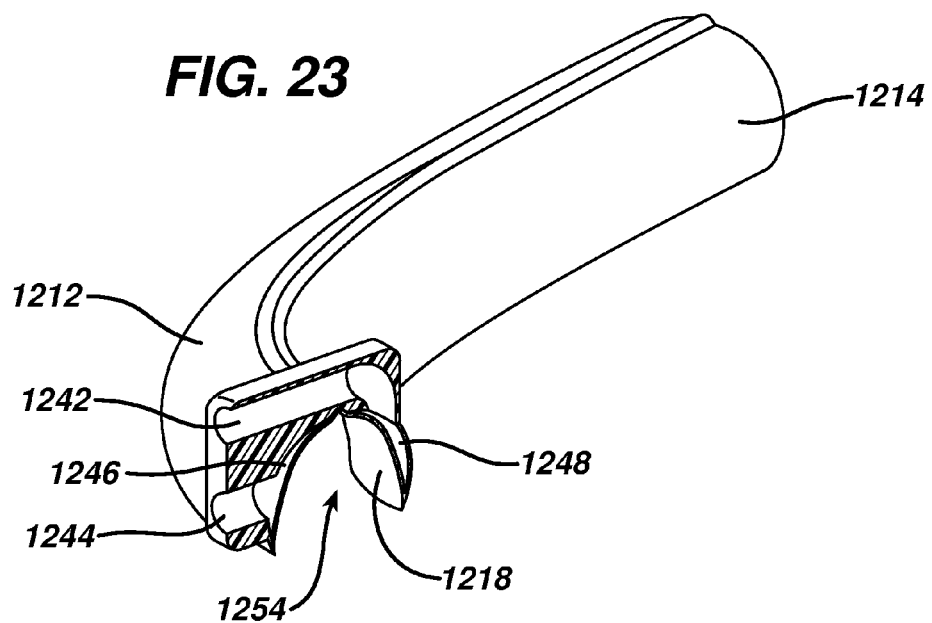
FIG. 23 is a cut-away view of the application tray of FIG. 20.

FIG. 23 is a vertical sectional view of the application tray 1200 of FIG. 20. The figures show first manifold 1246, defined as the space bordered by outer front wall 1212 and inner front wall 1216. Second manifold 1248 is defined as the space bordered by outer back wall 1214 and inner back wall 1218. The liquid contact chamber (LCC) 1254 is defined by inner front wall 1216, inner back wall 1218 and inner base wall 1250.

In one embodiment of a cleaning operation, cleaning liquid enters first manifold 1246 through first port 1244 by pressure and then enters LCC 1254 through inner front wall jet slots 1232. A vacuum is pulled on second port 1242 to pull the cleaning liquid through inner back wall jet slots 1234, into second manifold 1248 and finally into second port 1242. In this embodiment, jets of cleaning liquid are first directed onto the front side of the teeth from one side of the LCC, directed through, between, and around the teeth from the other side of the LCC into the second manifold to provide controlled interdental, gumline, surface and/or gingival area cleaning. Next, the flow in the manifolds is reversed. Cleaning liquid enters second manifold 1248 through second port 1242 by pressure and then enters LCC 1254 through inner back wall jet slots 1234. A vacuum is pulled on first port 1244 to pull the cleaning liquid through inner front wall jet slots 1232, into first manifold 1246 and finally into first port 1244. In the second portion of this embodiment, jets of cleaning liquid are directed onto the back side of the teeth, and directed through, between, and around the teeth and/or gingival area. The alternating of pressure/vacuum through a number of cycles creates a turbulent, repeatable and reversible flow, thereby providing reciprocation of liquid over and about the surfaces of the oral cavity.

It is also possible to deliver different liquid compositions to first manifold 1246 and second manifold 1248. The different liquid compositions would then combine in the LCC for improved cleaning efficacy. In the dual manifold design it may be preferable to supply each manifold from a separate chamber, such as in a dual action piston pump configuration, where one supply line connects and to supply first manifold 1246 and the other piston supply line provides and removes from second manifold 1248 (when one manifold is being supplied the second manifold is removing and vice versa).

Figure 24A:
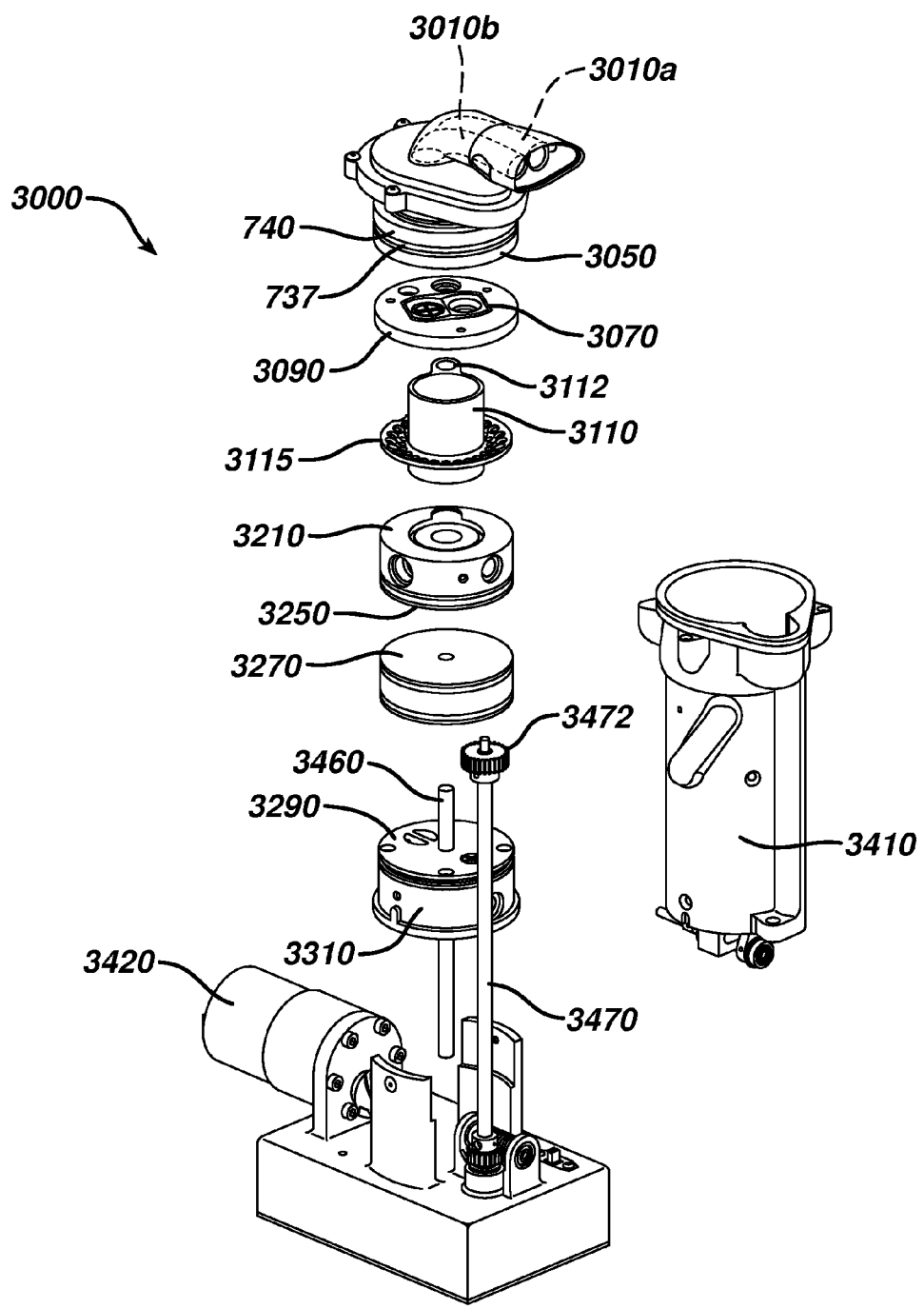
FIG. 24a is an exploded view of an embodiment of a hand piece according to the present invention.

An embodiment of a hand-held device according to the present invention is shown in FIGS. 24a to 24e. FIG. 24a is an exploded view of a hand piece 3000 that pumps liquid to, and pulls liquid from, the application tray, thus providing reciprocation of the liquid to and from the application tray. In this embodiment, device 3000 is designed in a modular fashion, with a pumping section, a vacuum section, a reciprocating section, and pumping and driving sections. Modular construction allows for easier design for manufacturing (DFM), with easy assembly and repair. The embodiment is also designed to minimize the size of the device as well as the amount of liquid used in operation.

Device 3000 includes outlet pipes 3010a and 3010b, reciprocating flow controller 710, inlet disk top section 3050, inlet disk bottom section 3090, delivery cylinder sleeve 3110 with bubble-break plate 3115 and delivery cylinder filling tube 3112, separator plates 3210, 3310, vacuum end disks 3250, 3290, vacuum piston 3270, vacuum cylinder sleeve 3410, piston rod 3460, indexing shaft 3470, and diverter drive gear 3472.

Figure 24B:
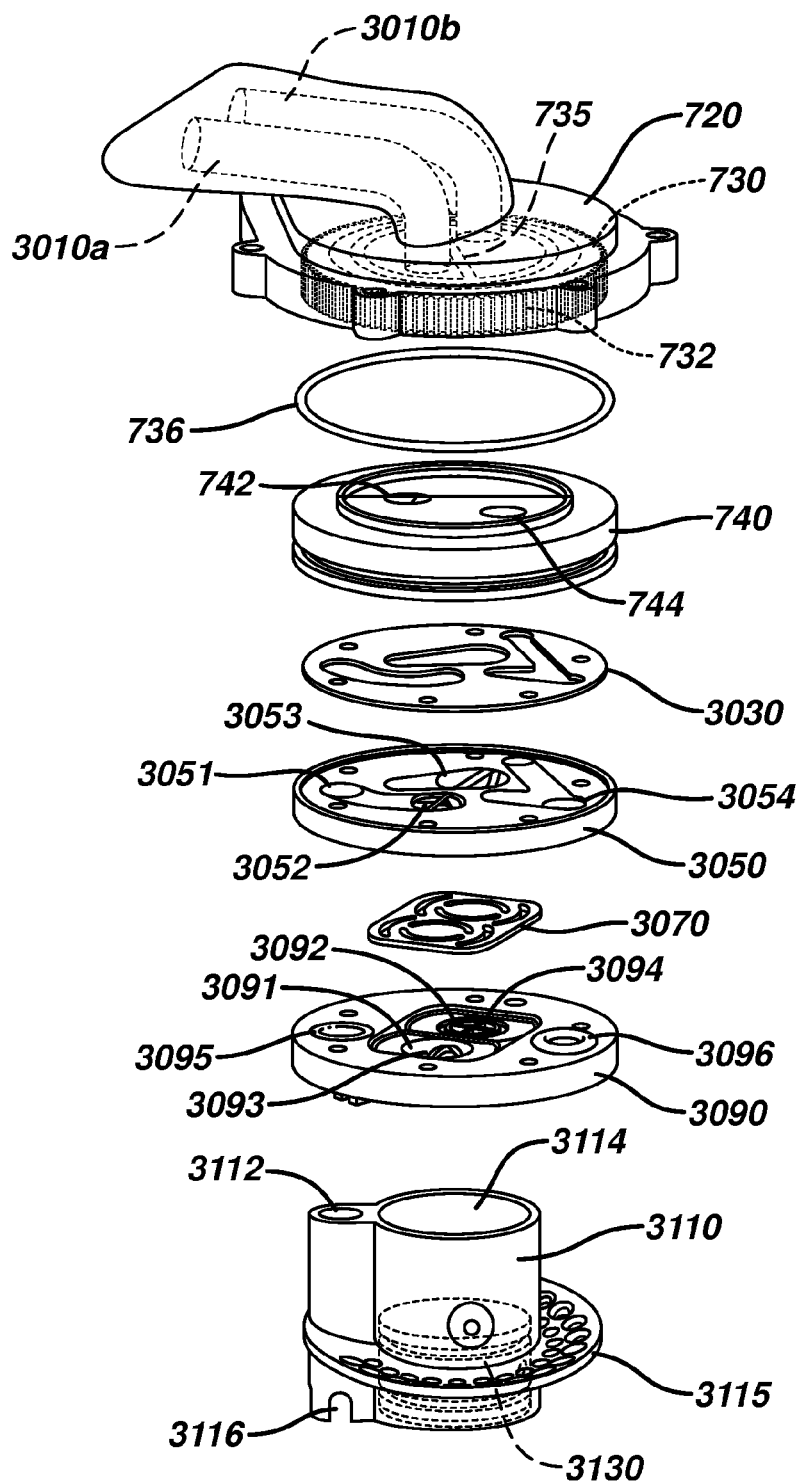

An exploded view of pumping section of device 3000 is shown on FIG. 24b. The figure shows outlet pipes 3010a, 3010b attached to cap 720 of reciprocating flow controller 710. Flow diverter disk 730, with position adjuster 732 in the form of a gear, is disposed in cap 720 and sits on base 740. O-ring 736 is between flow diverter disk 730 and base 740. Base ports 742 and 744 pass through base 740. Panel 735 for diverting liquid flow is disposed in flow diverter disk 730. Inlet disk top section 3050 has inlet disk top section ports 3051, 3052, 3053, and 3054, and is separated from base 740 by sealing gasket 3030. Inlet disk bottom section 3090 has inlet disk bottom section ports 3091, 3092, 3095, 3096. Dual flap valve 3070 is between inlet disk top section 3050 and inlet disk bottom section 3090, with the two flaps of dual flap valve 3070 above inlet disk bottom section ports 3091 and 3092 and below inlet disk top section ports 3052 and 3053. Inlet disk bottom section port 3091 includes a one-way valve 3093, allowing liquid to flow from inlet disk top section port 3052 to inlet disk bottom section port 3091 through dual flap valve 3070. Inlet disk bottom section port 3092 includes a one-way valve 3094, allowing liquid to flow from inlet disk bottom section port 3092 to inlet disk top section port 3053 through dual flap valve 3070. Inlet disk bottom section 3090 is disposed on top of delivery cylinder sleeve 3110. Delivery is disposed along delivery cylinder sleeve 3110, while delivery piston 3130 is disposed in the volume defined by delivery cylinder sleeve 3110. Bubble-break plate 3115 is disposed about cylinder sleeve 3110. Delivery volume 3114 is the volume defined by delivery cylinder sleeve 3110 minus the volume of delivery piston 3130.

Figure 24C:
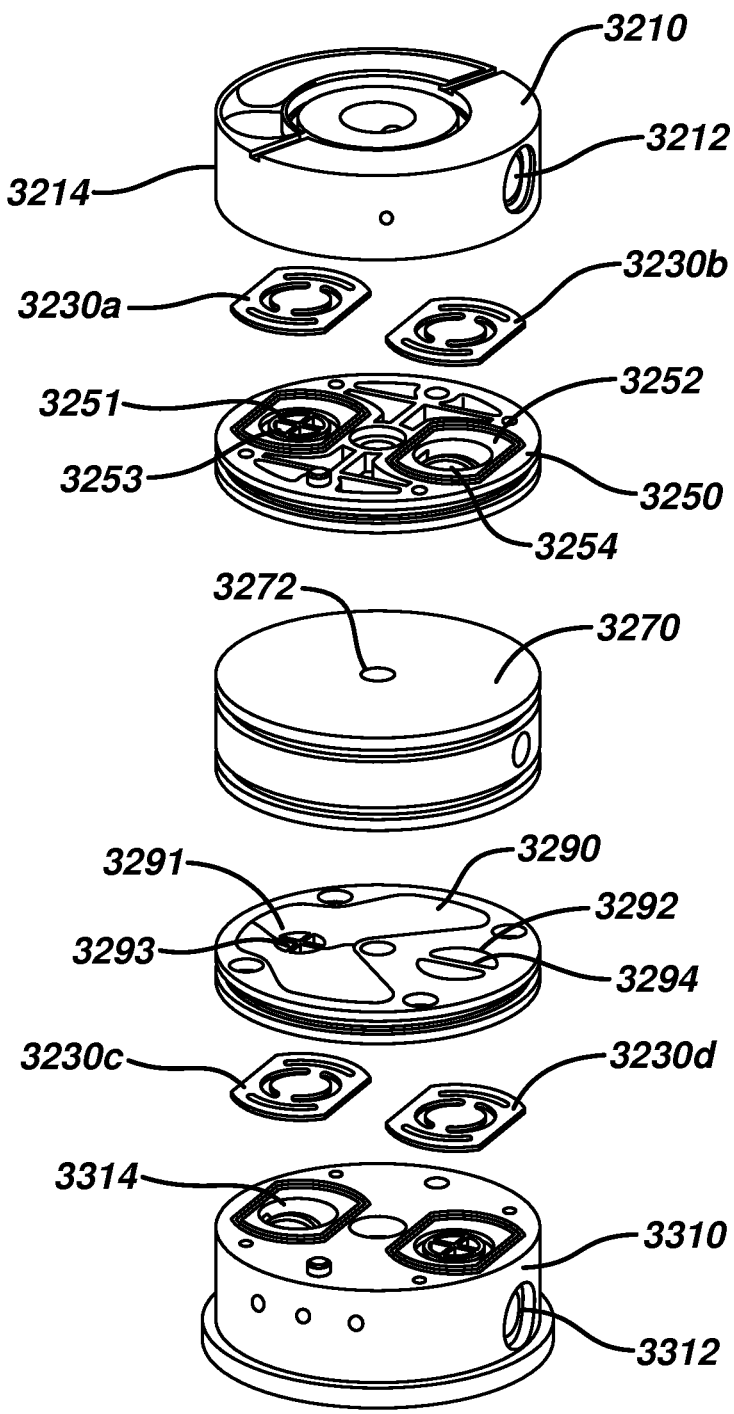

FIG. 24c is an exploded view of vacuum section of device 3000. The figure shows separator plate 3210, with separator plate ports 3212 and 3214, disposed on top of vacuum end disk 3250. Vacuum end disk 3250 has vacuum end disk ports 3251 and 3252. Flap valves 3230a and 3230b are between separator plate 3210 and vacuum end disks 3250. Flap valves 3230a and 3230b are above vacuum end disk ports 3251 and 3252 and below separator plate ports 3212 and 3214. Vacuum end disk port 3251 includes a one-way valve 3253, allowing liquid to flow from vacuum end disk port 3251 to separator plate port 3214 through flap valve 3230a. Vacuum end disk port 3252 includes a one-way valve 3254, allowing liquid to flow from separator plate port 3212 to vacuum end disk port 3252 through from flap valve 3230b. Vacuum piston 3270, disposed under vacuum end disks 3250, has piston rod hole 3272 through which piston rod 3460 passes. Beneath vacuum piston 3270 is vacuum end disk 3290, disposed on top of separator plate 3310. Vacuum end disk 3290 has vacuum end disk ports 3291 and 3292. Separator plate 3310 has separator plate ports 3312 and 3314. Flap valves 3230c and 3230d are between vacuum end disk 3290 and separator plate 3310, above vacuum end disk ports 3291 and 3292 and below separator plate ports 3312 and 3314. Vacuum end disk port 3291 includes a one-way valve 3293, allowing liquid to flow from vacuum end disk ports 3291 towards separator plate port 3314 through flap valve 3230c. Vacuum end disk port 3292 includes a one-way valve 3294, allowing liquid to flow from separator plate port 3312 to vacuum end disk port 3292 through flap valve 3230d.

Figure 24D:
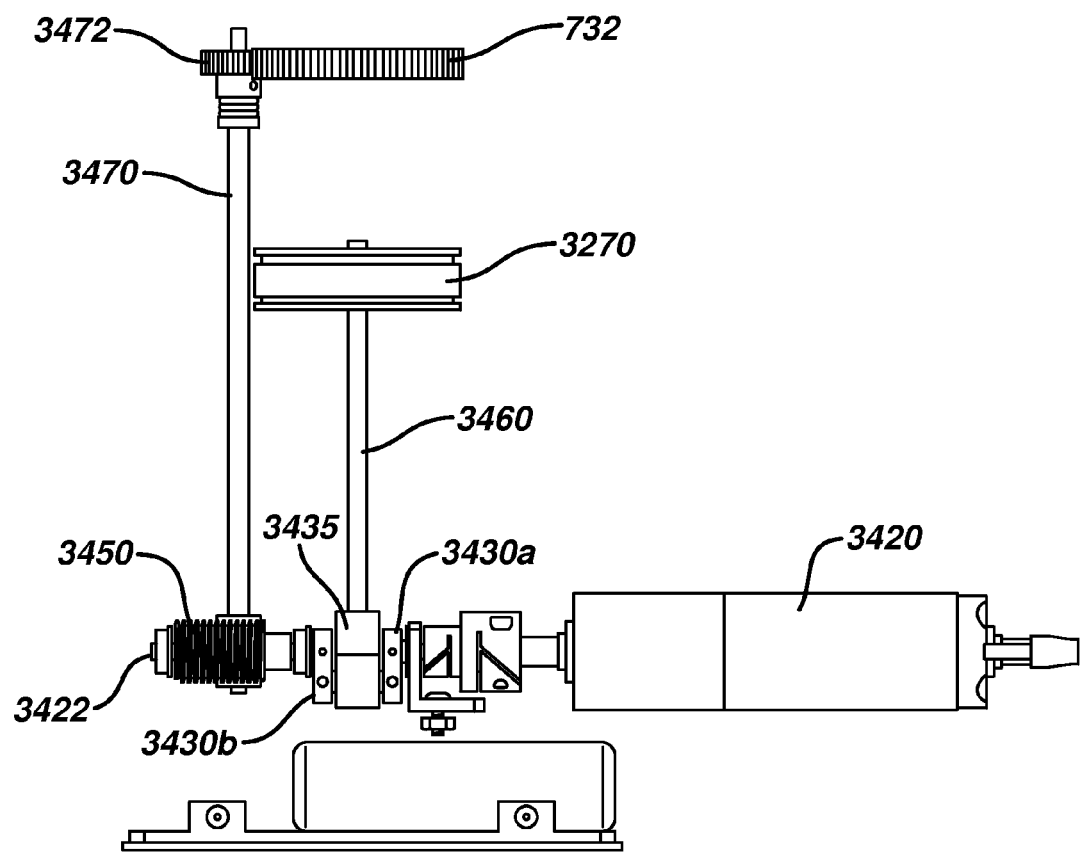

FIG. 24d is a side view of drive system of the pumping and driving sections of device 3000. Motor 3420 drives shaft 3422, which is linked to crankshaft arms 3430a and 3430b, and worm gear 3450. Crankshaft arms 3430a and 3430b are linked to crankshaft link arm 3435, which is linked to piston rod 3460. Piston rod 3460 is attached to vacuum piston 3270 and, though not shown, delivery piston 3130. Indexing shaft 3470 is in contact with worm gear 3450, which is linked to diverter drive gear 3472. When shaft 3412 spins, crankshaft arms 3430a, 3430b and crankshaft link arm 3435 convert the rotary motion of shaft 3422 to a linear, reciprocating motion on piston rod 3460, such that vacuum piston 3270 and delivery piston 3130 move up and down. Simultaneously, worm gear 3450 converts the rotary motion of shaft 3422 to a rotary motion of indexing shaft 3470. Indexing shaft 3470 rotates diverter drive gear 3472, which is linked to position adjuster 732 in reciprocating flow controller 710.

Figure 24E:
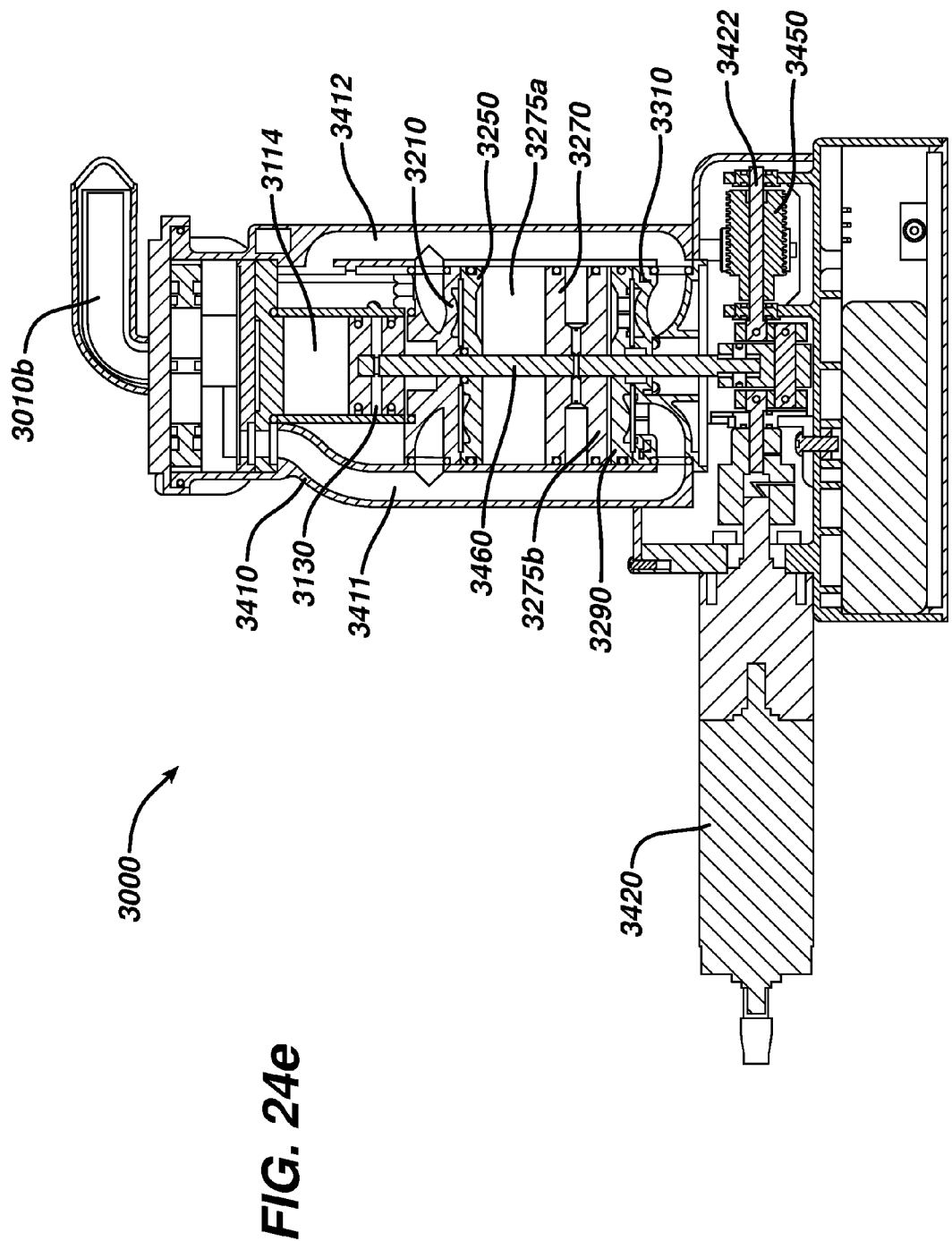
Figure 25A:
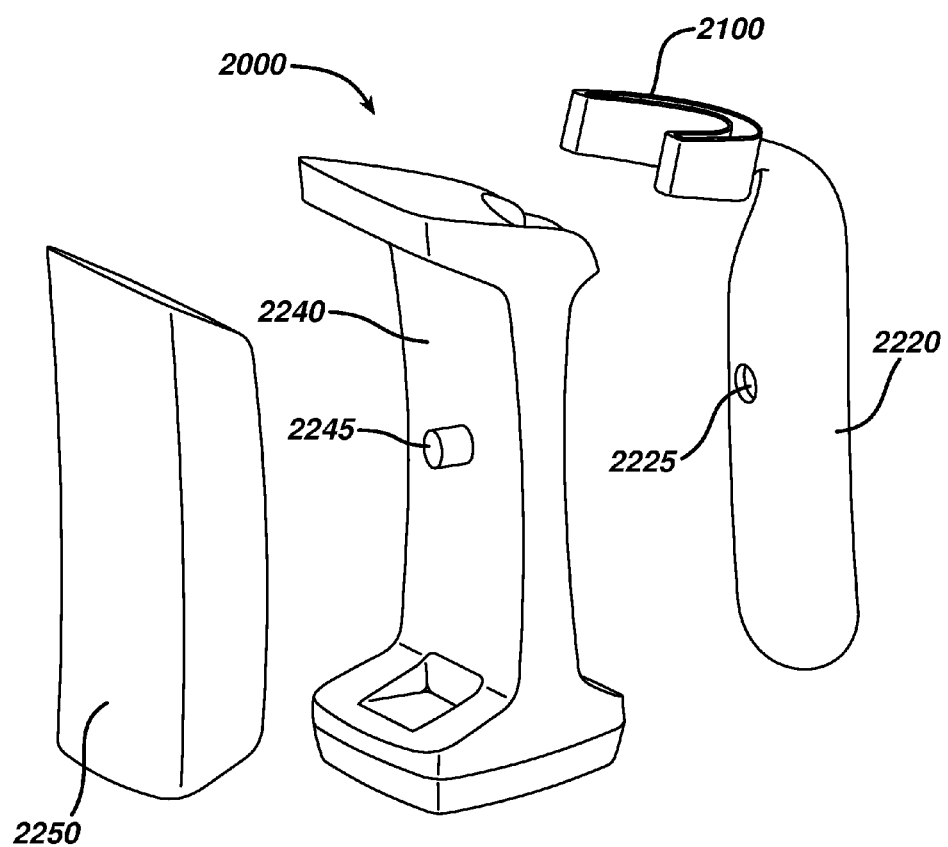
FIG. 25a is a back, top perspective view of an embodiment of a system according to the present invention.
Figure 25B:
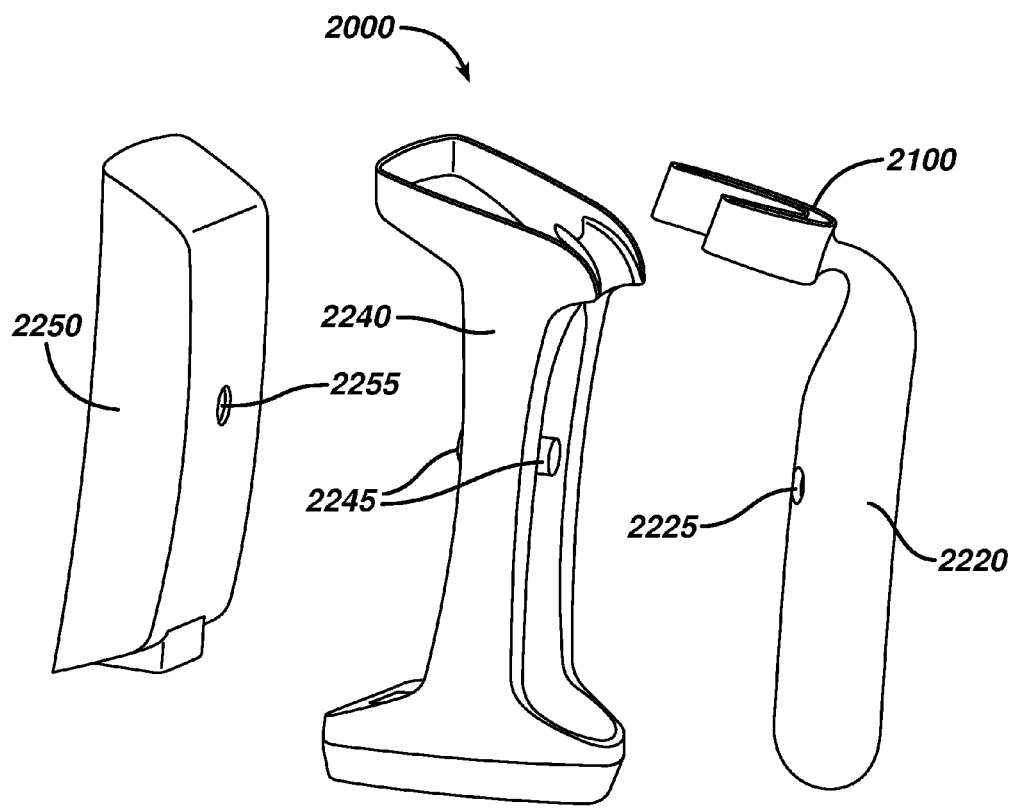
Figure 25C:
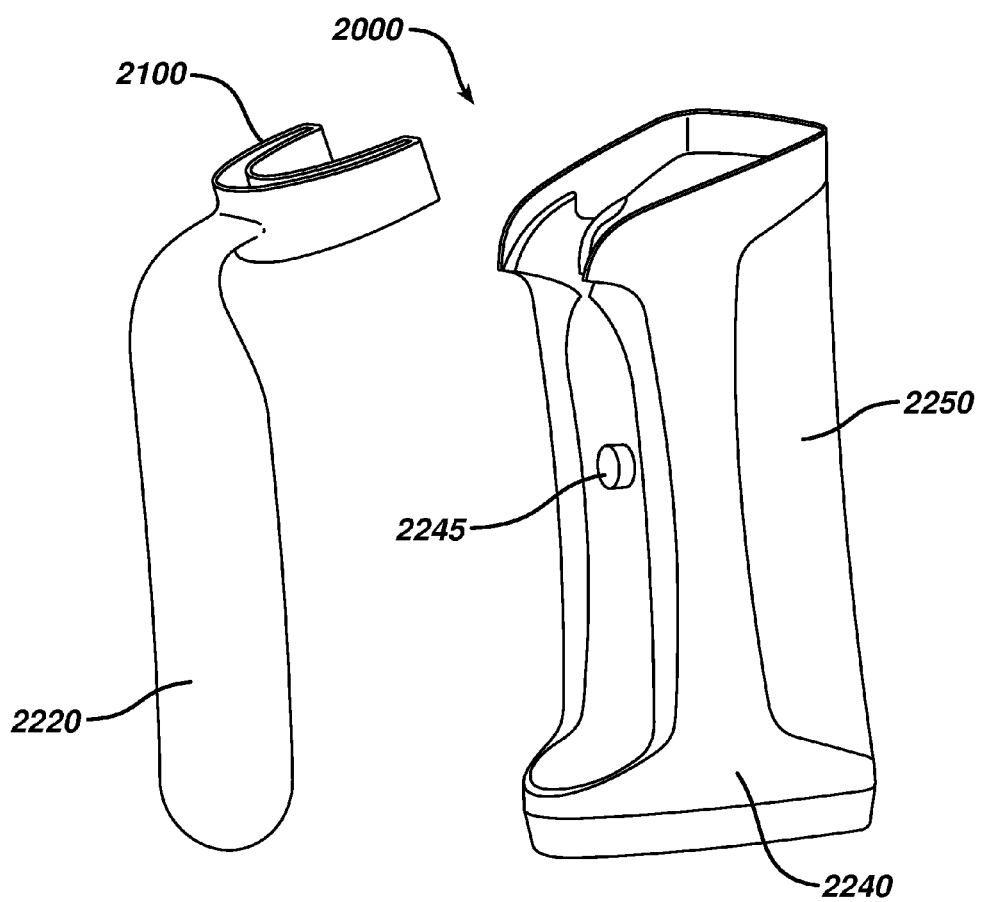
FIG. 25c is a back, top perspective view of the system of FIG. 25a, with the base station liquid reservoir attached to the base station.
Figure 25D:
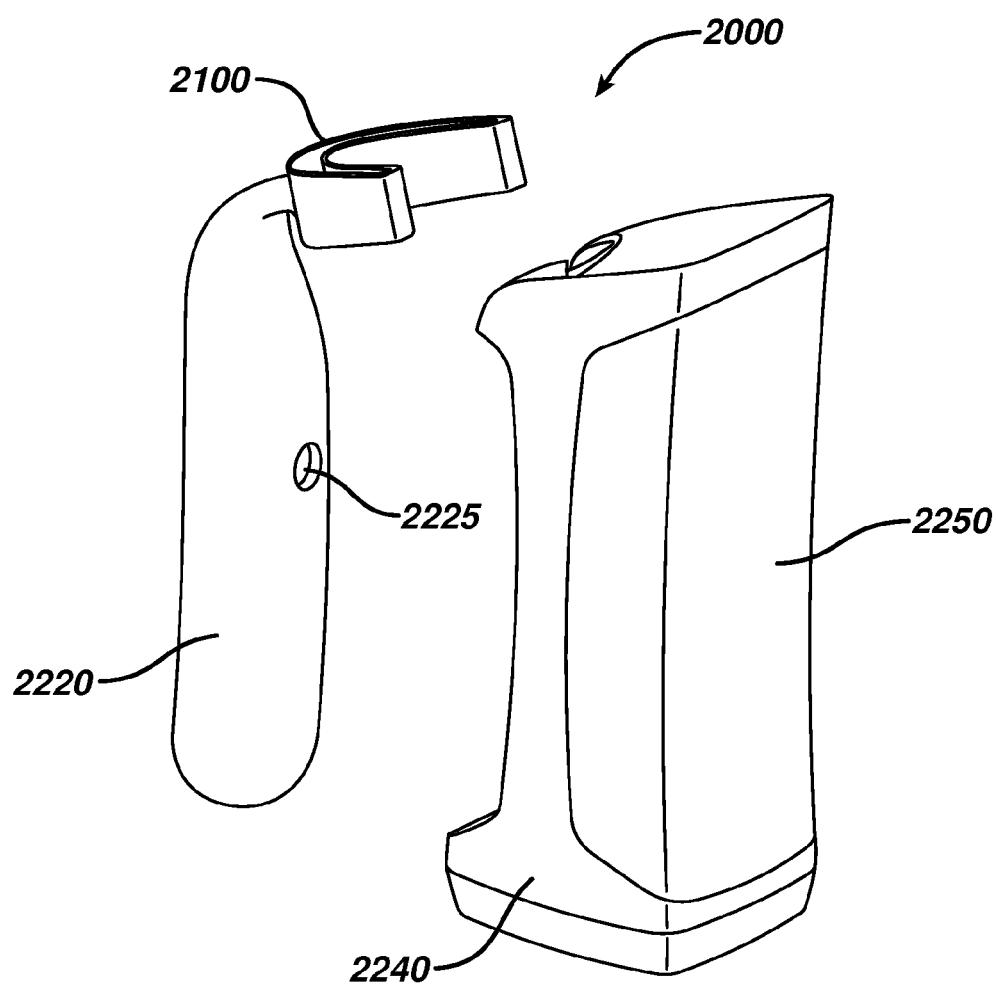
FIG. 25d is a front, top perspective view of the system of FIG. 25a, with the base station liquid reservoir attached to the base station.

FIG. 24e is a cut-away view of device 3000, showing the spatial relationships between the components in the pumping section, vacuum section, and pumping and driving sections. Cylinder volume 3412 is the volume of vacuum cylinder sleeve 3410 not occupied by the components of the pumping section, vacuum section, and pumping and driving sections, and serves as the liquid reservoir in the embodiment shown. The general operation of device 3000, is as follows:

1. Device 3000 is sufficiently filled with cleaning liquid. The liquid initially resides in cylinder volume 3412 of vacuum cylinder sleeve 3410.
2. The user inserts any embodiment of an application tray, for example application tray 100 or 1100, into their mouth. Device 3000 may be activated by a sensor (pressure sensor, proximity sensor, etc.) or the device may be activated by the user. The cleaning cycle is initiated.
3. On the "down stroke" of piston rod 3460, delivery piston 3130 pulls liquid from the bottom of cylinder volume 3412. The liquid flows through delivery cylinder filling tube 3112, inlet disk bottom section port 3095, inlet disk top section port 3051, inlet disk top section port 3052, dual flap valve 3070, and one-way valve 3093 in inlet disk bottom section port 3091, and into delivery volume 3114. It is preferred that the entry port 3116 on delivery cylinder filling tube 3112 is located at the bottom of the tube to minimize the total liquid required for cleaning/treatment and to avoid pulling air into delivery volume 3114.
4. On the "upstroke" of piston rod 3460, delivery piston 3130 forces the liquid though inlet disk bottom section port 3092 with one-way valve 3094. The liquid flows through dual flap valve 3070, through inlet disk top section port 3053, and finally through base port 742 of reciprocating flow controller 710.
5. Liquid flow through reciprocating flow controller 710 is described earlier using FIG. 9c and FIG. 9d. In brief, when reciprocating flow controller 710 is in its first position (FIG. 9c), incoming liquid from inlet disk top section port 3053 enters reciprocating flow controller 710 through base port 742. The liquid exits reciprocating flow controller 710 through cap port 722, flowing into outlet pipe 3010b. Returning liquid, flowing in through outlet pipe 3010a, reenters reciprocating flow controller 710 through cap port 724. The liquid exits reciprocating flow controller 710 through base port 744. When reciprocating flow controller 710 is in its second position (FIG. 9d), incoming liquid from inlet disk top section port 3053 enters reciprocating flow controller 710 through base port 742. The liquid exits reciprocating flow controller 710 through cap port 724, flowing into outlet pipe 3010a. Returning liquid, flowing in through outlet pipe 3010b, reenters reciprocating flow controller 710 through cap port 722. The liquid exits reciprocating flow controller 710 through base port 744. Reciprocation of cleaning liquid in application tray 100 of FIG. 1 is achieved by switching reciprocating flow controller 710 between its first and second positions. As shown in FIG. 24d, the switching of reciprocating flow controller 710 between its first and second positions is achieved by worm gear 3450, which converts the rotary motion of shaft 3422 to a rotary motion of indexing shaft 3470. Indexing shaft 3470 rotates diverter drive gear 3472, which is linked to position adjuster 732 in reciprocating flow controller 710. Though shown as continually rotating in this embodiment, it is to be understood that reciprocating flow controller 710 may be driven via separate means, such as another motor. Also, the time interval for switching reciprocating flow controller 710 between its first and second positions may, in some embodiments be between about 1 and about 100 seconds, or between about 2 and about 10 seconds, and may be varied over the course of the cleaning/treatment.
6. In the present embodiment, the vacuum section of device 3000 is effective during both the "upstroke" and "down stroke" of piston rod 3460. Vacuum piston 3270 is dual acting, and draws liquid from application tray 100 on both the upstroke and down stroke of vacuum piston 3270. The liquid flowing through base port 744 of reciprocating flow controller 710 flows through inlet disk top section port 3054 and continues through inlet disk bottom section port 3096, arriving in vacuum return tube 3411. The liquid in vacuum return tube 3411 is then drawn to vacuum volumes 3275a or 3275b. Vacuum volume 3275a is the volume between vacuum end disk 3250 and vacuum piston 3270. Vacuum volume 3275b is the volume between vacuum end disk 3290 and vacuum piston 3270. During the "upstroke" of piston rod 3460, the liquid in vacuum return tube 3411 is drawn through separator plate port 3312, and flows through flap valve 3230d, one-way valve 3294, and vacuum end disk port 3292, arriving in vacuum volume 3275b. During the "down stroke" of piston rod 3460, the liquid in vacuum return tube 3411 is drawn through separator plate port 3212, and flows through flap valve 3230b, one-way valve 3254, and vacuum end disk port 3222, arriving in vacuum volume 3275a. As noted, the vacuum piston 3270 in this embodiment is dual acting, drawing liquid from application tray 100 on both the upstroke and down stroke of vacuum piston 3270. So, while vacuum volume 3275b is drawing in liquid from vacuum return tube 3411, the liquid in vacuum volume 3275a is being pumped into cylinder volume 3412. In contrast, while vacuum volume 3275a is drawing in liquid from vacuum return tube 3411, the liquid in vacuum volume 3275b is being pumped into cylinder volume 3412. During the "upstroke" of piston rod 3460, the liquid in vacuum volume 3275a is pumped through vacuum end disk port 3251, and flows through one-way valve 3253, flap valve 3230a, and separator plate port 3214, arriving in cylinder volume 3412. During the "down stroke" of piston rod 3460, the liquid in vacuum volume 3275b is pumped through vacuum end disk port 3291, and flows through one-way valve 3293, flap valve 3230c, and separator plate port 3314, arriving in cylinder volume 3412.

7. The cycle continues with cycles comprising both "upstrokes" and "down strokes" of piston rod 3460, with liquid motion through device 3000 as described in steps 3 through 6 above.

The ratio of the total volume of vacuum volumes 3275a and 3275b to delivery volume 3114 may be any range, such as 1:1, optionally about 3:1 or greater, or about 4:1 or greater. Since delivery piston 3130 only delivers liquid on one "half" of the pumping/vacuuming cycle, while vacuum piston 3270 works on both halves of the cycle, the ratio of the volume of liquid delivered to application tray 100 to the volume of liquid drawn from application tray 100 is 8:1 per cycle. The dual acting vacuum piston 3270 also provides vacuum during the half of the stroke where delivery piston 3130 is not delivering liquid, increasing the opportunity to retrieve liquid from application tray 100, as well as clear additional liquid which leaked from application tray 100 into the oral cavity. Testing has shown a minimum 3:1 volumetric ratio of liquid vacuum to liquid delivery per stroke provided the necessary vacuum to minimize leakage into the oral cavity from application tray 100 when the tray has a marginal gingival seal, which may occur in embodiments of a universal (designed to fit a range of people) application tray 100 design.

In some embodiments vacuum piston 3270 is single acting. However, a dual acting vacuum piston 3270 may show some advantages.

In some embodiments, cylinder volume 3412 may have an air separator to reduce the foaming. Also, a breather vent may be required so that the pumping/vacuum system does not over pressurize and lock/fail. The breather vent may be on the opposite side of the cylinder volume 3412 from the outlets of separator plate ports 3214 and 3314 to avoid liquid splashing out of the breather vent. In addition there may be a wall to split the cylinder volume 3412 into two halves, to further reduce the chance of liquid splashing out of the breather vent.

In general, cylinder volume 3412 is vented since more liquid is being delivered to cylinder volume 3412 from the vacuum system than is being drawn from the delivery system. The excess (air) is exhausted from a vent in cylinder volume 3412. The vent could use a valve, such as an umbrella valve, so air can escape but cannot enter the reservoir from the same opening, or a 2-way valve or vent hole. To further reduce loss of liquid through the vent, a wall may be used to divide cylinder volume 3412 in two parts. One side contains the supply line, and the other side contains the vent. To optimize the separation of air from liquid in cylinder volume 3412, an air separator may be placed in the reservoir, below the supply line. As the liquid drops from supply line into cylinder volume 3412, it passes through an air separator, which may be a solid plate with holes. This allows the liquid to pass, while removing entrained air and helping to separate the two liquid states (liquid vs. gas). The air separator may have various designs, such as an angled solid shelf with holes, a spiraling ramp, a spiraling ramp with holes, two or more levels of angled shelves with holes, multiple spiraling ramps, similar to a multiple starting points for threads, (bottle caps, etc), sporadically located bosses that the liquid hits as it drops, assisting in separation.

In one embodiment, the hand-held device will be a self-contained, portable unit with a rechargeable battery, have a motor-driven piston pump for liquid delivery, have a mechanism to control the liquid flow, keep the temperature within a specified range, be modular in design, and have ergonomics well-suited to the user's hand. When the hand piece is in the base station, it will recharge the battery, refill the liquid reservoirs in the hand piece from those in the base station, and exchange samples and/or diagnostic information with the base station. It may also go through a cleaning process.

FIGS. 25a-25d show a representation example of an embodiment of a dental cleaning system 2000 according to the present invention. The figures show dental cleaning system 2000, showing hand-held device 2220, base station 2240, and base station liquid reservoir 2250. Base station liquid reservoir 2250 is used to refill the liquid reservoirs in device 2220. Application tray 2100 is shown attached to device 2220.

In this embodiment, base station liquid port 2245 is the conduit through which cleaning or treatment liquid passes from base station liquid reservoir 2250 to the liquid reservoirs in device 2220. Liquid leaves base station liquid reservoir 2250 through base station liquid reservoir port 2255, and enters the liquid reservoirs in device 2220 through port 2225.

When in base station 2240, the internal battery of device 2220 will recharge, and the liquid reservoirs in device 2220 will refill from those in base station 2240. Any diagnostic information in device 2220 will be exchanged with base station 2240. Device 2220 may also go through a cleaning process.

In other embodiments, a piston pump with check-valves will be used for liquid delivery.

In yet other embodiments, a rotary piston pump will be used for liquid delivery. This pump is known by those in the art, and the piston rotates as it reciprocates, therefore not needing any valves to operate. Reversing the rotation direction of the drive motor will reverse the liquid flow direction.

In still other embodiments diaphragm pumps, gear pumps, or double-action piston pumps will be used for liquid delivery. In the case of double-action piston pumps, when the liquid system is charged, this pump type has the benefit of reciprocating the direction of the liquid flow to the mouthpiece. Charged pneumatic cylinders, hand pump, or rotary pumps may be used to drive the system.

Example

A test was performed in which 4 subjects used systems according to the present invention to assess efficacy of the systems and methods of the invention from a germ reduction/kill perspective. One of the endpoint analytical methods used included bacterial viability determination via adenosine triphosphate (ATP) luminescence and total plate counts. In baseline samples, appropriate dilutions were made in 0.1% peptone water. For neutralizing both the rinsate and post-rinse samples, appropriate dilutions were made in $PO_4$ neutralizer. Mouthpieces substantially similar to those depicted in FIGS. 16-19 (universal mouthpiece) and FIGS. 20-23 (custom-fit) were used in the test, one each of which was tested using water and the other with Cool Mint Listerine® mouth rinse (CML).

Total Cell Counts, including total viable bacterial cells and total viable bad breath organisms, were enumerated from TSA blood plates and OOPS plates, respectively, following incubation of samples taken from the subjects for 5 days at 35-37° C. under anaerobic conditions. The Relative Light Units (RLU) is a measure of the amount of ATP in a sample. The higher the RLU value, the more ATP is present, and the more live bacteria there are. Total cell counts and RLU were determined for each sample taken from the subjects both before (baseline) and post rinsing, as well as on rinsates collected after rinsing.

The subjects rinsed the oral cavity with 5 mL water for 10 seconds. The baseline example was collected by having the subject expectorate the rinse water into a conical tube, and then expectorating an additional 1 ml of saliva into that tube. Each subject then rinsed the oral cavity, 2 with water using the respective mouthpiece designs, and 2 with the Cool Mint Listerine using the respective mouthpiece designs. The rinsate was then collected for each subject and 20 mL was placed in a conical tube. Each subject then repeated the rinse with 5 mL of water and as before the rinse and the post-rinse sample collected in a conical tube. The samples were incubated for 5 days and the cell counts and ATP measured. Results are presented in Tables 1-3. Subject 1 BL used water as the liquid and the universal mouthpiece. Subject 2 BL used water as the liquid and the custom-fit mouthpiece. Subject 3 BL used CML as the liquid and the universal mouthpiece. Subject 4 BL used CML as the liquid and the custom-fit mouthpiece.

TABLE 1

| Total Organisms | Average Counts | % Reduction from baseline | log reduction |
| --- | --- | --- | --- |
| Subject 1 BL | 1.88E+07 | | |
| Subject 2 BL | 2.07E+07 | | |
| Subject 3 BL | 1.13E+08 | | |
| Subject 4 BL | 1.93E+08 | | |
| Subject 1 Rinsate | 7.40E+04 | 99.6% | 2.40 |
| Subject 2 Rinsate | 1.90E+04 | 99.9% | 3.04 |

TABLE 1-continued

| Total Organisms | Average Counts | % Reduction from baseline | log reduction |
| --- | --- | --- | --- |
| Subject 3 Rinsate | 2.00E+03 | 100.0% | 4.75 |
| Subject 4 Rinsate | 3.00E+03 | 100.0% | 4.81 |
| Subject 1 Post | 7.50E+05 | 96.0% | 1.40 |
| Subject 2 Post | 3.02E+06 | 85.4% | 0.84 |
| Subject 3 Post | 8.70E+06 | 92.3% | 1.11 |
| Subject 4 Post | 7.20E+06 | 96.3% | 1.43 |

TABLE 2

| Bad Breath Organisms | Average Counts | % Reduction from baseline | log reduction |
| --- | --- | --- | --- |
| Subject 1 BL | 5.30E+06 | | |
| Subject 2 BL | 2.70E+06 | | |
| Subject 3 BL | 2.10E+07 | | |
| Subject 4 BL | 3.50E+07 | | |
| Subject 1 Rinsate | 3.10E+04 | 99.4% | 2.23 |
| Subject 2 Rinsate | 1.00E+03 | 100.0% | 3.43 |
| Subject 3 Rinsate | 1.50E+03 | 100.0% | 4.15 |
| Subject 4 Rinsate | 1.00E+03 | 100.0% | 4.54 |
| Subject 1 Post | 6.50E+05 | 87.7% | 0.91 |
| Subject 2 Post | 4.40E+05 | 83.7% | 0.79 |
| Subject 3 Post | 2.80E+06 | 86.7% | 0.88 |
| Subject 4 Post | 2.10E+06 | 94.0% | 1.22 |

TABLE 3

| ATP | RLU | % Reduction from baseline | log reduction |
| --- | --- | --- | --- |
| Subject 1 BL | 7.44E+04 | | |
| Subject 2 BL | 3.93E+04 | | |
| Subject 3 BL | 2.18E+05 | | |
| Subject 4 BL | 3.12E+05 | | |
| Subject 1 Rinsate | 3.14E+04 | 57.7% | 0.37 |
| Subject 2 Rinsate | 2.85E+04 | 27.4% | 0.14 |
| Subject 3 Rinsate | 2.81E+04 | 87.1% | 0.89 |
| Subject 4 Rinsate | 2.61E+04 | 91.6% | 1.08 |
| Subject 1 Post | 3.01E+04 | 59.5% | 0.39 |
| Subject 2 Post | 2.90E+04 | 26.1% | 0.13 |
| Subject 3 Post | 7.04E+04 | 67.7% | 0.49 |
| Subject 4 Post | 3.40E+04 | 89.1% | 0.96 |

CONCLUSIONS

Post-rinse plate count data demonstrates approximate significant reduction for both water rinse and CML rinse. Analysis of the rinsate plate count data also demonstrates a significant reduction from the baseline in the water rinse, and even more significant reduction from the baseline in the CML rinse. The log reductions present in the water rinsate suggests mechanical bacterial removal during treatment in the absence of antimicrobials. The higher log reductions present in the CML rinsate suggests a combination of mechanical and antimicrobial activity during treatment.

Though several embodiments have been described, it should be understood that the scope of the present invention embraces other possible variations, being limited only by the contents of the accompanying claims, which includes the possible equivalents.

What is claimed is:

1. An oral care system suitable for use in providing a beneficial effect to an oral cavity of a mammal, said system comprising,
   a. an application tray or mouthpiece for directing a liquid effective for providing said beneficial effect to said oral cavity onto a plurality of surfaces of said oral cavity, said application tray or mouthpiece comprising:
- a chamber for contacting said liquid with said plurality of surfaces, said chamber defined by front and rear inner walls and a base inner wall of said means for directing, said base wall extending between said front and rear inner walls, said front and rear inner walls comprising a plurality of openings,
- a first manifold for containing a first portion of said liquid and providing said first portion to and from said chamber through said openings of said front inner wall,
- a second manifold for containing a second portion of said liquid and providing said second portion to and from said chamber through said openings of said rear inner wall,
- a first port for conveying said first portion of liquid to and from said first manifold,
- a second port for conveying said second portion of liquid to and from said second manifold;

b. means for providing reciprocation of said liquid over said plurality of surfaces under conditions effective to provide said beneficial effect, said means of providing reciprocation of said liquid comprising at least one pump for alternately: (i) directing fluid into said chamber through said first manifold and out of said chamber through said second manifold, and (ii) directing fluid into said chamber through said second manifold and out of said chamber through said first manifold; and c. means for providing said liquid to and from said application tray or mouthpiece and said means for providing reciprocation.

2. The system of claim 1 wherein said application tray or mouthpiece comprises a plurality of front lumens connected by said first manifold and a plurality of rear lumens connected by said second manifold.

3. The system of claim 1 wherein said application tray or mouthpiece comprises a top piece and a bottom piece for providing substantially simultaneous contact of a plurality of surfaces of both top and bottom sections of said oral cavity.

4. The system of claim 1 wherein said pump is a dual action piston pump.

5. The system of claim 1 wherein said at least one pump comprises a first pump to direct fluid from said means for providing reciprocation into said chamber and a second pump for providing vacuum to pull fluid out of said chamber.

6. The system of claim 1 further comprising a reservoir for containing said fluid.

7. The system of claim 1 wherein said means for providing reciprocation comprises a hand held device.

8. The system of claim 7 further comprising a base station into which the hand held means for providing reciprocation is inserted to dock.

9. An oral care system suitable for use in providing a beneficial effect to an oral cavity of a mammal, said system comprising:
   a. a mouthpiece or application tray for directing a liquid effective for providing said beneficial effect to said oral cavity onto a plurality of surfaces of said oral cavity, said mouthpiece or application tray comprising:
   - a chamber for contacting said liquid with said plurality of surfaces, said chamber defined by front and rear inner walls and a base inner wall of said means for directing, said base wall extending between said front and rear inner walls, said front and rear inner walls comprising a plurality of openings,
   - a first manifold for containing a first portion of said liquid and providing said first portion to and from said chamber through said openings of said front inner wall,
   - a second manifold for containing a second portion of said liquid and providing said second portion to and from said chamber through said openings of said rear inner wall,
   - a first port for conveying said first portion of liquid to and from said first manifold, and
   - a second port for conveying said second portion of liquid to and from said second manifold;

b. a reservoir for containing said fluid;
   c. at least one pump to simultaneously direct fluid from said reservoir to said mouthpiece or application tray and pull fluid from said mouthpiece or application tray to said reservoir;
   d. means for providing said liquid to and from said reservoir and said mouthpiece or application tray;

wherein said fluid is alternately: (i) directed into said chamber through said first manifold and out of said chamber through said second manifold, and (ii) directed into said chamber through said second manifold and out of said chamber through said first manifold.

* * * * *